(12) United States Patent
Nagaraju et al.

(10) Patent No.: US 10,358,661 B2
(45) Date of Patent: Jul. 23, 2019

(54) MICROORGANISM WITH MODIFIED HYDROGENASE ACTIVITY

(71) Applicant: LanzaTech New Zealand Limited, Skokie, IL (US)

(72) Inventors: Shilpa Nagaraju, Skokie, IL (US); Michael Koepke, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 15/387,047

(22) Filed: Dec. 21, 2016

(65) Prior Publication Data

US 2017/0183690 A1 Jun. 29, 2017

Related U.S. Application Data

(60) Provisional application No. 62/271,466, filed on Dec. 28, 2015.

(51) Int. Cl.
| | |
|---|---|
| *C12N 1/21* | (2006.01) |
| *C12N 9/02* | (2006.01) |
| *C12P 7/06* | (2006.01) |
| *C12P 7/16* | (2006.01) |
| *C12P 7/54* | (2006.01) |
| *C12P 7/18* | (2006.01) |
| *C12P 7/04* | (2006.01) |

(52) U.S. Cl.
CPC .......... *C12P 7/065* (2013.01); *C12N 9/0067* (2013.01); *C12P 7/04* (2013.01); *C12P 7/18* (2013.01); *C12P 7/54* (2013.01); *C12Y 112/07002* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 9,834,795 B2* | 12/2017 | Koepke | ............... | C12N 9/0006 |
| 2009/0081257 A1 | 3/2009 | Maier et al. | | |
| 2014/0212976 A1* | 7/2014 | Mueller | ............... | C12N 9/0036 |
| | | | | 435/440 |

OTHER PUBLICATIONS

Huang, J Bacteriol, 194: 3689-3699, 2012.
International Search Report for International Patent Application PCT/US2016/069044, Korean Intellectual Property Office, dated Apr. 13, 2017.
Ahmed, Biomass Bioenerg, 30: 665-672, 2006.
Biswas, Biotechnol Biofuels, 8: 20, 2015.
Calusinska, Microbiol, 156: 1575-1588, 2010.
He, Biochem Biophys Res Commun, 16: 127-133, 1989.
Marcellin, Low carbon fuels and commodity chemicals from waste gases—systematic approach to understand energy metabolism in a model acetogen, Green Chem, 2016.
Mock, J Bacteriol, 197: 2965-2980, 2015.
Shima, FEBS Lett, 585: 353-356, 2011.
Sun, Biochem, 31: 3158-3165, 1992.
Vignais, FEMS Microbiol Rev, 25: 455-501, 2001.
Wang, J Bacteriol, 195: 4373-4386, 2013.
Xu, Biomass Bioenerg, 45: 303-310, 2012.
Liew et al., "Gas Fermentation—A Flexible Platform for commercial Scale Production of Low-Carbon-Fuels and Chemicals from Waste and Renewable Feedstocks," Frontiers in Microbiology 7: article 694 (2016).

* cited by examiner

*Primary Examiner* — Robert B Mondesi
*Assistant Examiner* — Todd M Epstein
(74) *Attorney, Agent, or Firm* — Christine Falaschetti

(57) ABSTRACT

The invention provides genetically engineered microorganisms with modified hydrogenase activity and methods related thereto. Typically, the microorganisms are C1-fixing microorganisms with one or more disruptive mutations in a hydrogenase enzyme or a hydrogenase accessory enzyme. The microorganisms may have improved tolerance to toxins, such as acetylene, isocyanide, ammonium, or nitric oxide, improved production of products, such as ethanol, 2,3-butanediol, and isopropanol, and/or improved fixation of carbon, such as carbon derived from CO or $CO_2$.

11 Claims, 6 Drawing Sheets

Specification includes a Sequence Listing.

US 10,358,661 B2

MICROORGANISM WITH MODIFIED HYDROGENASE ACTIVITY

CROSS REFERENCE TO RELATED APPLICATIONS

This application claims the benefit of U.S. Provisional Patent Application No. 62/271,466 filed Dec. 28, 2015, the entirety of which is incorporated herein by reference.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The majority of $CO_2$ comes from the burning fossil fuels to produce energy, although industrial and forestry practices also emit $CO_2$ into the atmosphere. Reduction of greenhouse gas emissions, particularly $CO_2$ emissions, is critical to halt the progression of global warming and the accompanying shifts in climate and weather.

It has long been recognized that catalytic processes may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol. Efficient production of such products may be limited, for example, by slow microbial growth, limited gas uptake, sensitivity to toxins, or diversion of carbon substrates into undesired byproducts. Accordingly, there remains a need for genetically engineered microorganisms having improved characteristics, especially improved carbon fixation, product production, and toxin resistance.

SUMMARY OF THE INVENTION

The invention provides genetically engineered microorganisms with modified hydrogenase activity and methods related thereto. In particular, the invention provides a genetically engineered C1-fixing microorganism comprising a disruptive mutation in a hydrogenase enzyme or a hydrogenase accessory enzyme.

For example, the hydrogenase enzyme may be an electron-bifurcating, NADP- and ferredoxin dependent [FeFe]-hydrogenase (e.g., CAETHG_2794-99 (HytABCDE1E2)); a multi-subunit [FeFe]-hydrogenase (e.g., CAETHG_1576-78 or CAETHG_3569-71); a mono-subunit [FeFe]-hydrogenase (e.g., CAETHG_0110 or CAETHG_3841); and/or a [NiFe]-hydrogenase (e.g., CAETHG_0861-62). In a preferred embodiment, the hydrogenase enzyme is CAETHG_2794-99 (HytABCDE1E2) comprising a disruptive mutation in one or more of subunits HytA, HytB, HytC, HytD, HytE1, and HytE2. In another example, the hydrogenase accessory enzyme may be a [NiFe]-hydrogen maturation protease (e.g., CAETHG_0860).

The microorganism of the invention may be derived from a parental microorganism such as Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, or Thermoanaerobacter kiuvi. In preferred embodiments, the microorganism of the invention may be derived from Clostridium autoethanogenum, Clostridium ljungdahlii, or Clostridium ragsdalei.

The microorganism of the invention may have a different product profile than the parental microorganism. For instance, the microorganism of the invention may produce more ethanol than a parental microorganism without the disruptive mutation.

The microorganism of the invention may be capable of fixing carbon. For example, the microorganism of the invention may consume a gaseous substrate comprising a C1-carbon source comprising $CO_2$ and/or CO. In a preferred embodiment, the microorganism of the invention is capable of net carbon capture.

The microorganism of the invention may also have different tolerances to toxins than the parental microorganism. For instance, the microorganism of the invention may be more tolerant of a toxin, e.g., acetylene, isocyanide, ammonium, or nitric oxide, than a parental microorganism without the disruptive mutation.

The invention also provides a method of producing a product comprising culturing the microorganism of the invention in the presence of a gaseous substrate. Typically, the gaseous substrate comprises a C1-carbon source, e.g., $CO_2$ or CO. A wide variety of products may be produced, including native products, such as ethanol or 2,3-butanediol, or non-native products, such as isopropanol. In certain embodiments, microbial biomass may also be considered a product.

The invention further provides a method of fixing carbon comprising culturing the microorganism of the invention in the presence of a gaseous substrate comprising a C1-carbon source, whereby the microorganism consumes more C1-carbon than it produces. Typically, the gaseous substrate comprises a C1-carbon source, e.g., $CO_2$ or CO.

DETAILED DESCRIPTION OF THE INVENTION

Figure 1A:
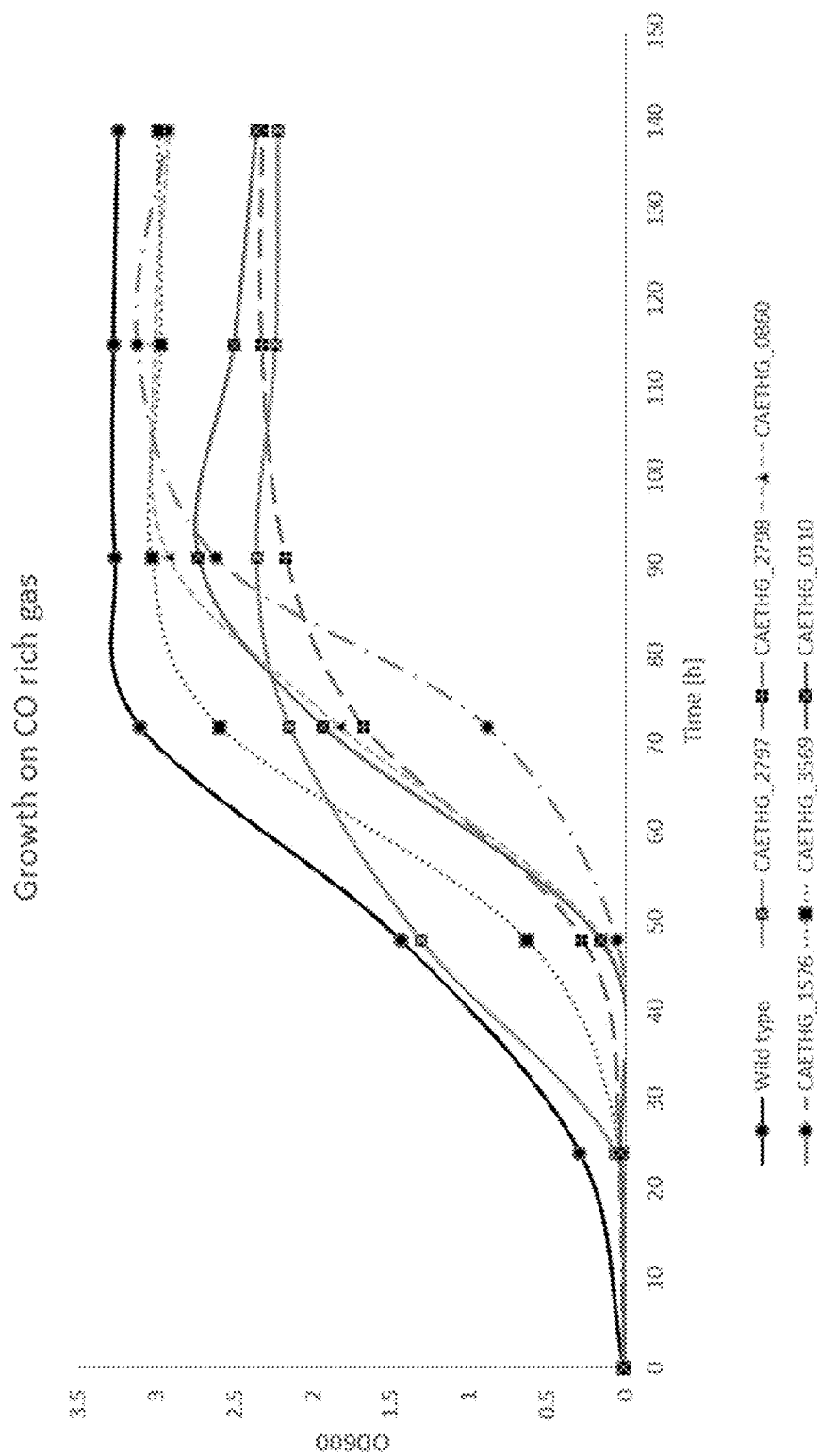
FIGS. 1A-1C are graphs showing the results of growing C. autoethanogenum LZ1561 (control) and C. autoethanogenum mutants CAETHG_1576, CAETHG_2797, CAETHG_3569, CAETHG_2798, CAETHG_0110, and CAETHG_0860 on CO-rich gas, specifically the production of microbial biomass (FIG. 1A), acetate (FIG. 1B), and ethanol (FIG. 1C).

Hydrogenases play a central role in microbial energy metabolism. In particular, a "hydrogenase" is an enzyme that catalyzes the reversible oxidation of molecular hydrogen ($2H^+ + 2e^- \leftrightarrow H_2$). Hydrogenases can be distributed into three classes: the [Fe]-hydrogenases, the [NiFe]-hydrogenases, and the metal-free hydrogenases. The vast majority of known hydrogenases belong to the first two classes, and over 100 of these enzymes have been characterized genetically and/or biochemically. Compelling evidence from sequences and structures indicates that the [NiFe]- and [Fe]-hydrogenases are phylogenetically distinct classes of proteins. The same catalytic core of the [NiFe]-hydrogenases is a heterodimeric protein, although additional subunits are present in many of these enzymes. Functional classes of [NiFe]-hydrogenases have been defined and they are consistent with categories defined by sequence similarity of the catalytic subunits. The catalytic core of the [Fe]-hydrogenases is a ca. 350-residue domain that accommodates the active site (H-cluster). A few monomeric [Fe]-hydrogenases are barely larger than the H-cluster domain. Many others are monomeric as well, but possess additional domains that contain redox centers, mostly iron-sulfur. Some [Fe]-hydrogenases are oligomeric. The modular structure of hydrogenases is strikingly illustrated in recently unveiled sequences and structures. Microbial genome sequences are bringing forth a significant body of additional hydrogenase sequence data and contribute to the understanding of hydrogenase distribution and evolution (Vignais, *FEMS Microbiol Rev*, 25: 455-501, 2001).

A "hydrogenase accessory enzyme" is an enzyme that affects the activity or expression of a hydrogenase enzyme, but is not itself a hydrogenase enzyme. For example, [NiFe]-hydrogen maturation protease (CAETHG_0860) catalyzes a proteolytic cleavage important to the maturation of [NiFe]-hydrogenase (CAETHG_0861-62) in *C. autoethanogenum*. Accordingly, [NiFe]-hydrogen maturation protease (CAETHG_0860) is a hydrogenase accessory enzyme that affects the activity of the hydrogenase enzyme [NiFe]-hydrogenase (CAETHG_0861-62). Herein, reference to hydrogenases enzymes (or disruption thereof) should be interpreted to also encompass hydrogenase accessory enzymes (or disruption thereof).

Typically, *Clostridia* hydrogenases are capable of interacting with a wide variety of electron acceptors or donors, which gives *Clostridia* an evolutionary survival advantage across a variety of habitats (Calusinska, *Microbiol*, 156: 1575-1588, 2010). In particular, *C. autoethanogenum* has genes for six putative hydrogenases: (1) electron-bifurcating, NADP- and ferredoxin dependent [FeFe]-hydrogenase (CAETHG_2794-99) (Wang, *J Bacteriol*, 195: 4373-4386, 2013), (2) multi-subunit [FeFe]-hydrogenase (CAETHG_1576-78), (3) multi-subunit [FeFe]-hydrogenase (CAETHG_3569-71), (4) mono-subunit [FeFe]-hydrogenase (CAETHG_0110), (5) mono-subunit [FeFe]-hydrogenase (CAETHG_3841), and (6) [NiFe]-hydrogenase (CAETHG_0861-62).

The electron-bifurcating, NADP- and ferredoxin dependent [FeFe]-hydrogenase is composed of the subunits HytABCDE1E2 and catalyzes the reversible reduction of $NADP^+$ and $Fd_{ox}$ with 2 $H_2$.

$$2H_2 + NADP^+ + Fd_{ox} \leftrightarrows NADPH + Fd_{red}^{2-} + 3H^+$$

HytA is the H-cluster harboring the [FeFe]-hydrogenase subunit, HytB is an iron-sulfur flavoprotein harboring the NADP binding site, and the other subunits are iron-sulfur proteins. The hydrogenase forms a tight complex with the selenium- and tungsten-dependent formate dehydrogenase FdhA. The hydrogenase (HytABCDE1E2) is encoded by the genes CAETHG_2794-99 (hytABCDE1E2), which form a transcription unit. Besides the structural genes, genes required for [FeFe]-hydrogenase maturation, hydE (CAETHG_1691; 47 FPKM), hydF (CAETHG_2063; 21 FPKM) and hydG (CAETHG_0339; 148 FPKM) are present in *C. autoethanogenum* as well as in *C. ljungdahlii* (Mock, *J Bacteriol*, 197: 2965-2980, 2015). FIG. 2 of Mock, *J Bacteriol*, 197: 2965-2980, 2015 shows expression of the *C. autoethanogenum* hyt-fdh gene cluster and surrounding genes during growth in continuous culture. When grown in a CO (E0'=−520 mV) rich atmosphere, the same HytABCDE1E2 NADP-specific hydrogenase is predicted to catalyze in vivo the formation of $H_2$ rather than the uptake of $H_2$ in order to re-oxidize reduced ferredoxin. It would be useful if these electrons could be used to fix carbon into more reduced products such as ethanol, isopropanol, and others.

The genome of *C. autoethanogenum* harbors genes for two other multi-subunit [FeFe]-hydrogenases (CAETHG_1576-78; CAETHG_3569-71), which have a subunit structure and composition very similar to those of the electron-bifurcating and NAD- and ferredoxin-dependent [FeFe]-hydrogenases from *T. maritima, A. woodii, M. thermoacetica*, and *R. albus*. While CAETHG_3569-71 is hardly expressed (2 FPKM), CAETHG_1576-78 is the second highest expressed hydrogenase in *C. autoethanogenum*, but at significantly lower level (35 FPKM) than the characterized electron-bifurcating and NADP-dependent [FeFe]-hydrogenase. CAETHG_1576-78 is absent in *C. ljungdahlii* (Mock, *J Bacteriol*, 197: 2965-2980, 2015).

The genome of *C. autoethanogenum* harbors genes for two mono-subunit [FeFe]-hydrogenases, CAETHG_0110 and CAETHG_3841. These generally use ferredoxin as electron acceptor/donor, are not electron bifurcating, and all show only very low expression (5-9 FPKM). There is also a third gene, CAETHG_0119, annotated as [FeFe]-hydrogenase but it lacks the sequence segments involved in H-cluster iron binding and can therefore not encode for a functional [FeFe]-hydrogenase (Mock, *J Bacteriol*, 197: 2965-2980, 2015).

Genes for a [NiFe]-hydrogenase (CAETHG_0861-62) are also present and form a putative transcription unit with a [NiFe]-hydrogen maturation protease (CAETHG_0860). No expression for these three genes has been found (<0.1 FPKM). This has also been reported in transcriptomic datasets for *C. ljungdahlii* growing on either $H_2/CO_2$ or fructose. Consistently, not all the genes required for [NiFe]-hydrogenase maturation are present. Only the genes hypECDF (CAETHG_0372-0369) were found whereas the genes hypAB appear to be absent. Nevertheless, the hypECDF genes are expressed at a reasonable level (35 FPKM) (Mock, *J Bacteriol*, 197: 2965-2980, 2015).

Additionally, (i) the reduction of $NAD^+$ with reduced ferredoxin via membrane-associated energy coupling reaction is catalyzed by Rnf A-B (CAETHG_3227-32), (ii) the reduction of NADP with reduced ferredoxin and NADH is catalyzed by Nfn (CAETHG_1580), (iii) the reduction of acetic acid to acetaldehyde by reduced ferredoxin is catalyzed by acetaldehyde:ferredoxin oxidoreductase (AOR) (CAETHG_0092, CAETHG_0102), and (iv) the reduction of acetyl-CoA plus $CO_2$ to pyruvate is catalyzed by pyruvate:ferredoxin oxidoreductase PFOR (CAETHG_0928, CAETHG_3029).

*C. ljungdahlii* has homologues of five of the six hydrogenases found in *C. autoethanogenum*. The five hydrogenases of *C. ljungdahlii* are CLJU_c07030-07080 (homologue of CAETHG_2794-99), CLJU_c14700-20 (homologue of CAETHG_3569-71), CLJU_c20290 (homologue of CAETHG_0110), CLJU_c17280 (homologue of CAETHG_3841), and CLJU_c28650-60 (homologue of CAETHG_0861-62). The homologues of CAETHG_1576-78 are absent in *C. ljungdahlii* but a predicted iron-dependent hydrogenase (CLJU_c37220) is annotated in its place.

One of the genes encoding the Rnf complex in *C. ljungdahlii* has been knocked out resulting in reduced growth under heterotrophic growth and no growth under autotrophic conditions on $H_2/CO_2$ or CO. The energy for minimal growth in the former case could be derived from substrate level phosphorylation by glycolysis.

Similarly, *C. ragsdalei* has homologues of five of the six hydrogenases found in *C. autoethanogenum*. The homologue of CAETHG_1576-78 and CLJU_c37220 is not present in *C. ragsdalei*.

Other C1-fixing microorganisms, including *Acetobacterium woodii, Alkalibaculum bacchii, Blautia producta, Butyribacterium methylotrophicum, Clostridium aceticum, Clostridium carboxidivorans, Clostridium coskatii, Clostridium drakei, Clostridium formicoaceticum, Clostridium magnum, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi* have similar hydrogenases, the sequences of which are generally publically available.

The inventors have surprisingly discovered that disruption of hydrogenases in C1-fixing microorganisms results in a variety of improved characteristics.

Certain microorganisms are known to consume $CO_2$ or CO, rendering gas fermentation a potential route to both removing C1-carbon from the atmosphere and sustainably producing useful fermentation products, such as fuels and chemicals. However, many of these microorganisms also produce some amount of $CO_2$, making it difficult to determine whether or not gas fermentation actually results in net carbon capture. The inventors have discovered that disruption of one or more hydrogenases in a microorganism causes the microorganism to consume more gaseous C1-carbon (e.g., in the form of $CO_2$ or CO) than it produces (e.g., in the form of $CO_2$), resulting in net carbon capture in organic fermentation products, such as ethanol. This can be illustrated by equations below. In particular, the more $H_2$ can be utilized, the less CO is required and the less $CO_2$ is produced per molecule of produced ethanol. At a certain point, $CO_2$ and $H_2$ can be utilized alone, in the absence of CO.

When no $H_2$ is utilized, 6 molecules of CO are required per 1 molecule of ethanol and 4 molecules of $CO_2$ produced (Equation 1). When 3 molecules of $H_2$ are utilized, 3 molecules of CO are required per 1 molecule of ethanol and 1 molecule of $CO_2$ produced (Equation 2). When 4 molecules of $H_2$ are utilized, 2 molecules of CO are required per 1 molecule of ethanol produced (Equation 3); $CO_2$ may also be produced as a byproduct. When 6 molecules of $H_2$ are utilized, no CO is required per 1 molecule of ethanol produced (Equation 4). Additionally, 2 molecules of $CO_2$ are utilized and no $CO_2$ is produced.

$$6CO + 3H_2O \rightarrow CH_3CH_2OH + 4CO_2 \quad \text{(Equation 1)}$$

$$3CO + 3H_2 \rightarrow CH_3CH_2OH + CO_2 \quad \text{(Equation 2)}$$

$$2CO + 4H_2 \rightarrow CH_3CH_2OH + H_2O \quad \text{(Equation 3)}$$

$$2CO_2 + 6H_2 \rightarrow CH_3CH_2OH + 3H_2O \quad \text{(Equation 4)}$$

Moreover, the inventors have found that some hydrogenases are redundant, such that a microorganism, e.g., *C. autoethanogenum*, can compensate for disruption of any one hydrogenase, e.g., HytABCDE1E2, by expressing other hydrogenase(s). In fact, the inventors have discovered that all six hydrogenases of *C. autoethanogenum* are redundant. Without wishing to be bound by any particular theory, the inventors believe disrupting certain hydrogenases leads to expression of other hydrogenase(s) with different uptake/production rates and/or cofactor dependencies, such that an overall shift in cofactor dependence is observed, e.g., from ferredoxin plus NADP to ferredoxin plus NAD or to ferredoxin only or direct reduction of $CO_2$ to formate with hydrogen. This results in a microorganism with a different gas uptake and/or carbon fixation profile. Additionally, this may result in a microorganism that grows better on $H_2$-containing gases than the parental microorganism from which it was derived.

Furthermore, the inventors have discovered that disruption of microbial hydrogenases causes the microorganism to produce greater amounts of other reduced fermentation products, such as ethanol, 2,3-butanediol, and/or isopropanol. Hydrogenase knockouts have been developed in non-C1-fixing microorganisms for the purpose of reducing hydrogen production. For example, hydrogen production in cellulolytic *C. thermocellum* was inhibited by knocking out the gene responsible for maturation of apoform hydrogenases (Biswas, *Biotechnol Biofuels*, 8: 20, 2015). However, results obtained in *C. thermocellum* are only applicable to the production of fuels and chemicals from carbohydrate feedstocks, such as lignocellulosic biomass. Such results cannot be extended to C1-fixing microorganisms, such as acetogenic bacteria, given the extensive differences in the metabolisms of carbohydrate-consuming microorganisms and C1-fixing microorganisms. Moreover, carbohydrate-consuming microorganisms (e.g., *C. thermocellum*) produce hydrogen, but typically do not utilize hydrogen, while C1-fixing microorganisms (e.g., *C. autoethanogenum*) are capable of utilizing hydrogen, such that hydrogenases play fundamentally different roles in these different types of microorganisms.

Additionally, the inventors believe that disruption of microbial hydrogenases causes the microorganism to have improved resistance to toxins which would ordinarily inhibit hydrogenases. For example, acetylene inhibits the nickel-containing hydrogenases (NiFe and NiFeSe) of anaerobic sulfate reducing bacteria (He, *Biochem Biophys Res Commun*, 16: 127-133, 1989) and the Ni- and Fe-containing hydrogenase of *A. vinelandii* (Sun, *Biochem*, 31: 3158-3165, 1992). Isocyanides inhibit [Fe]-hydrogenases (Shima, *FEBS Lett*, 585: 353-356, 2011). Ammonium inhibits *C. ragsdalei* hydrogenases (Xu, *Biomass Bioenerg*, 45: 303-310, 2012). Nitric oxide inhibits *C. carboxidivorans* P7 uptake hydrogenase at 150 ppm (Ahmed, *Biomass Bioenerg*, 30: 665-672, 2006). Thus, the microorganism of the invention may have improved resistance to acetylene, isocyanide, ammonium, nitric oxide, or other toxins known to inhibit hydrogenases.

Definitions and Background

The term "genetic modification" or "genetic engineering" broadly refers to manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation or a knock-down mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art. In the present invention, the disruptive mutation may be a disruptive mutation of a hydrogenase enzyme or a subunit thereof (or a gene encoding a hydrogenase enzyme or a subunit thereof) and/or a disruptive mutation of a hydrogenase accessory enzyme or a subunit thereof (or a gene encoding a hydrogenase accessory enzyme or a subunit thereof).

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum*, *Clostridium ljungdahlii*, or *Clostridium ragsdalei*. In a further preferred embodiment, the genes of the invention are codon optimized for expression in *Clostridium autoethanogenum* LZ1561, which is deposited under DSMZ accession number DSM23693.

"Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at Inhoffenstraß 7B, D-38124 Braunschwieg, Germany on Jun. 7, 2010 under the terms of the Budapest Treaty and accorded accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/− [1] | − | − | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/− [2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | − [3] | + | + | − |
| *Oxobacter pfennigii* | + | + | + | − | + | + | − |
| *Sporomusa ovata* | + | + | + | − | + | +/− [4] | − |
| *Sporomusa silvacetica* | + | + | + | − | + | +/− [5] | − |
| *Sporomusa sphaeroides* | + | + | + | − | + | +/− [6] | − |
| *Thermoanaerobacter kiuvi* | + | + | + | − | + | − | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3$^{rd}$ edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of *Clostridia* comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate may comprise at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$. The $H_2$ may be derived from or produced by any suitable process, including the formation of $H_2$ using electrodes.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

"Toxin," as used herein, refers to any chemical that inhibits or otherwise adversely affects a hydrogenase enzyme of a microorganism. The toxin may be, for example, acetylene, isocyanide, ammonium, or nitric oxide. The microorganism of the invention is generally more resistant to (i.e., tolerant of) toxins than the parental microorganism from which the microorganism of the invention is derived, such that the microorganism of the invention is able to grow better and/or produce more products than the parental microorganism when exposed to the same amount of a toxin. Similarly, the microorganism of the invention may be able to grow and/or produce products in the presence of an amount of a toxin that would typically kill the parental microorganism.

Herein, "carbon fixation" or "carbon capture" or "carbon assimilation" refers to the conversion process of inorganic carbon (e.g., CO and/or $CO_2$) to organic compounds (e.g., ethanol, 2,3-butanediol, acetic acid, and/or isopropanol) by living organisms. In preferred embodiments, the microorganism of the invention is capable of net carbon capture, consuming more gaseous C1-carbon than it produces. In particular, the microorganism of the invention may consume more gaseous C1-carbon in the form of CO and/or $CO_2$ than it produces in the form of $CO_2$. In certain embodiments, the microorganism of the invention is capable of net $CO_2$ capture, where the microorganism consumes more $CO_2$ than it produces.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In certain embodiments, microbial biomass itself may be considered a product.

A "native product" is a product produced by a genetically unmodified microorganism. For example, ethanol, acetate, and 2,3-butanediol are native products of *Clostridium autoethanogenum, Clostridium ljungdahlii*, and *Clostridium ragsdalei*. A "non-native product" is a product that is produced by a genetically modified microorganism, but is not produced by a genetically unmodified microorganism from which the genetically modified microorganism is derived. For example, isopropanol is a non-native product of *Clostridium autoethanogenum, Clostridium ljungdahlii*, and *Clostridium ragsdalei*.

"Selectivity" refers to the ratio of the production of a target product to the production of all fermentation products produced by a microorganism. The microorganism of the invention may be engineered to produce products at a certain selectivity or at a minimum selectivity. In one embodiment, a target product account for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the invention is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example describes the construction of *C. autoethanogenum* hydrogenase mutants.

Microorganisms

*C. autoethanogenum* LZ1561, i.e., DSM23693 (a derivate of DSM10061), was obtained from DSMZ. Growth was carried out at 37° C. using strictly anaerobic conditions and techniques (Hungate, Meth Microbiol, 3B: 117-132, 1969; Wolfe, Adv Microb Physiol, 6: 107-146, 1971). Chemically defined PETC medium without yeast extract was used. A 30 psi CO-containing gas mix (44% CO, 32% Na, 22% $CO_2$, 2% $H_2$) served as a sole source of carbon and energy.

| PETC medium | Per 1.0 L of medium |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent solution | 0.006-0.008% (v/v) |
| Distilled water | Up to 1.0 L |
| | pH 5.5 (adjusted with HCl) |

| Wolfe's vitamin solution | Per 1.0 L of solution |
|---|---|
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |

-continued

| Wolfe's vitamin solution | Per 1.0 L of solution |
|---|---|
| Vitamin B12 | 0.1 mg |
| p-Aminobenzoic acid | 5 mg |
| Lipoic acid | 5 mg |
| Thiamine | 5 mg |
| Distilled water | To 1.0 L |

| Trace metal solution | Per 1.0 L of solution |
|---|---|
| Nitrilotriacetic acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1.0 L |

| Reducing agent solution | Per 100 mL of solution |
|---|---|
| NaOH | 0.9 g |
| Cysteine·HCl | 4 g |
| $Na_2S$ | 4 g |
| Distilled water | To 100 mL |

Analysis of Metabolites

To remove proteins and other cell residues, 400 µl samples were mixed with 100 µl of a 2% (w/v) 5-sulfosalicylic acid and centrifuged at 14,000×g for 3 min to separate precipitated residues. 10 µl of the supernatant was then injected into the HPLC for analyses. HPLC analysis of 2,3-butanediol, 2-butanol, and other metabolites was performed using an Agilent 1100 Series HPLC system equipped with a RID operated at 35° C. (Refractive Index Detector) and an Aminex HPX-87H column (300×7.8 mm, particle size 9 µm) kept at 35° C. Slightly acidified water was used (0.005 M $H_2SO_4$) as mobile phase with a flow rate of 0.6 ml/min. For distinction of 2,3-butanediol sterioisomers, HPLC analysis was performed using an Agilent 1100 Series HPLC system equipped with a RID operated at 35° C. (Refractive Index Detector) and an Alltech IOA-2000 Organic acid column (150×6.5 mm, particle size 8 µm) kept at 60° C. Slightly acidified water was used (0.005 M $H_2SO_4$) as mobile phase with a flow rate of 0.25 ml/min.

Group II Intron Based Insertional Inactivation of Hydrogenase Genes in *C. autoethanogenum* LZ1561

The hydrogenases in *C. autoethanogenum* LZ1561 were inactivated using ClosTron group II intron mediated gene disruption tool (Heap, *J Microbiol Meth*, 80: 49-55, 2010). The Perutka algorithm hosted on the ClosTron website was used to identify group II intron target sites and to design the intron targeting regions which were synthesized delivered in pMTL007C-E5 vector by DNA2.0. The resulting vectors contain a Retro-tranposition-Activated ermB Marker (RAM) which confers resistance to antibiotic clarithromycin upon insertion of group-II into the target site. The insertion of group II intron at the target site will most likely affect the expression of other genes in the same complex.

Inactivation of hydrogenase genes CAETHG_0860, CAETHG_1576, CAETHG_3569, and CAETHG_0110 has already been reported earlier by Mock, *J Bacteriol*, 197: 2965-2980, 2015. However, the HytABCDE1E2 complex and another hydrogenase CAETHG_3841 could not be inactivated and were therefore concluded to be essential for growth on syngas. These hydrogenase genes, specifically CAETHG_2797 and CAETHG_2798 from the HytABCDE1E2 cluster and CAETHG_3841, were targeted again, but with group-II intron insertion sites of a lower score than that reported by Mock, *J Bacteriol*, 197: 2965-2980, 2015. Surprisingly, despite the lower predicted score by the Perutka algorithm these hydrogenase genes could be disrupted using the new group-II intron insertion sites, demonstrating that these are not essential and that any hydrogenase in *C. autoethanogenum* is redundant.

| Target gene | Group II insertion site | Sequence of intron targeting region | Primers used for screening | |
|---|---|---|---|---|
| | | | Forward primer | Reverse primer |
| CAETHG_1576 | 1038\|1039s | SEQ ID NO: 51 | Og119f SEQ ID NO: 52 | Og120r SEQ ID NO: 53 |
| CAETHG_0110 | 123\|124s | SEQ ID NO: 54 | Og121f SEQ ID NO: 55 | Og122r SEQ ID NO: 56 |
| CAETHG_0860 | 807\|808a | SEQ ID NO: 57 | Og117f SEQ ID NO: 58 | Og118r SEQ ID NO: 59 |
| CAETHG_3569 | 931\|932a | SEQ ID NO: 60 | Og125f SEQ ID NO: 61 | Og126r SEQ ID NO: 62 |
| CAETHG_3841 | 73\|74s | SEQ ID NO: 63 | Og123f SEQ ID NO: 64 | Og124r SEQ ID NO: 65 |
| CAETHG_2797 | 190\|191a | SEQ ID NO: 66 | FS001for SEQ ID NO: 67 | FS001rev SEQ ID NO: 68 |
| CAETHG_2798 | 543\|544s | SEQ ID NO: 69 | FS003for SEQ ID NO: 70 | FS003rev SEQ ID NO: 71 |

To generate the mutants, the plasmids were introduced into *C. autoethanogenum* LZ1561 as described above. Streaks of single colonies were made sequentially first on PETC-MES media containing 15 µg/ml thiamphenicol followed by on agar plates with PETC-MES media containing 5 µg/ml clarithromycin. Colonies were randomly screened for group II intron insertion by PCR using primers listed above. Amplification of PCR products of 300-500 bp with primers indicated the unmodified *C. autoethanogenum* LZ1561 locus. Amplification of PCR products of ~2.2 kb using the same set of primers indicated insertion of ClosTron group II intron in the target gene. These results confirm the disruption of hydrogenases in *C. autoethanogenum* LZ1561. The following positive clones were selected for further studies: ΔCAETHG_1576-Clone1, ΔCAETHG_0110-

Clone5, ΔCAETHG_0860-Clone5, ΔCAETHG_3569-Clone8, ΔCAETHG_2797-Clone1, and ΔCAETHG_2798-Clone1.

Example 2

This example profiles the growth of *C. autoethanogenum* hydrogenase mutants on a CO-rich gas mix containing 50% CO, 4% $H_2$, 25% $CO_2$, and 21% $N_2$.

*C. autoethanogenum* LZ1561 was used as a control. ΔCAETHG_2797-Clone1 and ΔCAETHG_2798-Clone1 mutants essentially represent the knockout of one functional hydrogenase, HytABCDE1E2, which is most highly expressed under CO-rich gas conditions. All strains were grown in PETC-MES medium in 250 ml serum bottles and gassed to 30 psig with the CO-rich gas mix. The growth experiment was initiated by inoculating the media to a starting OD of 0.01. Growth and metabolite formation was followed for 139 hours.

Figure 1B:
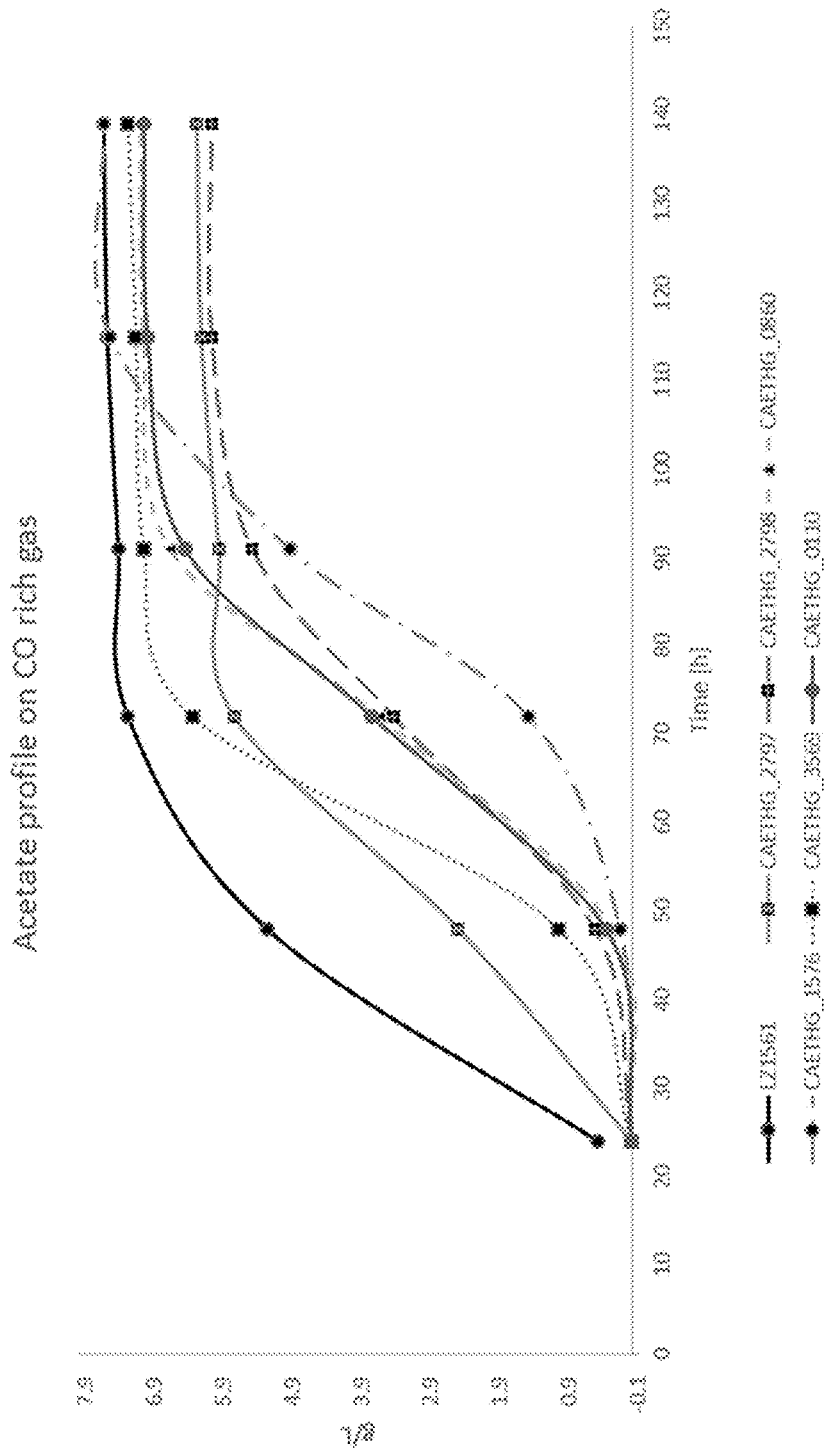
Figure 1C:
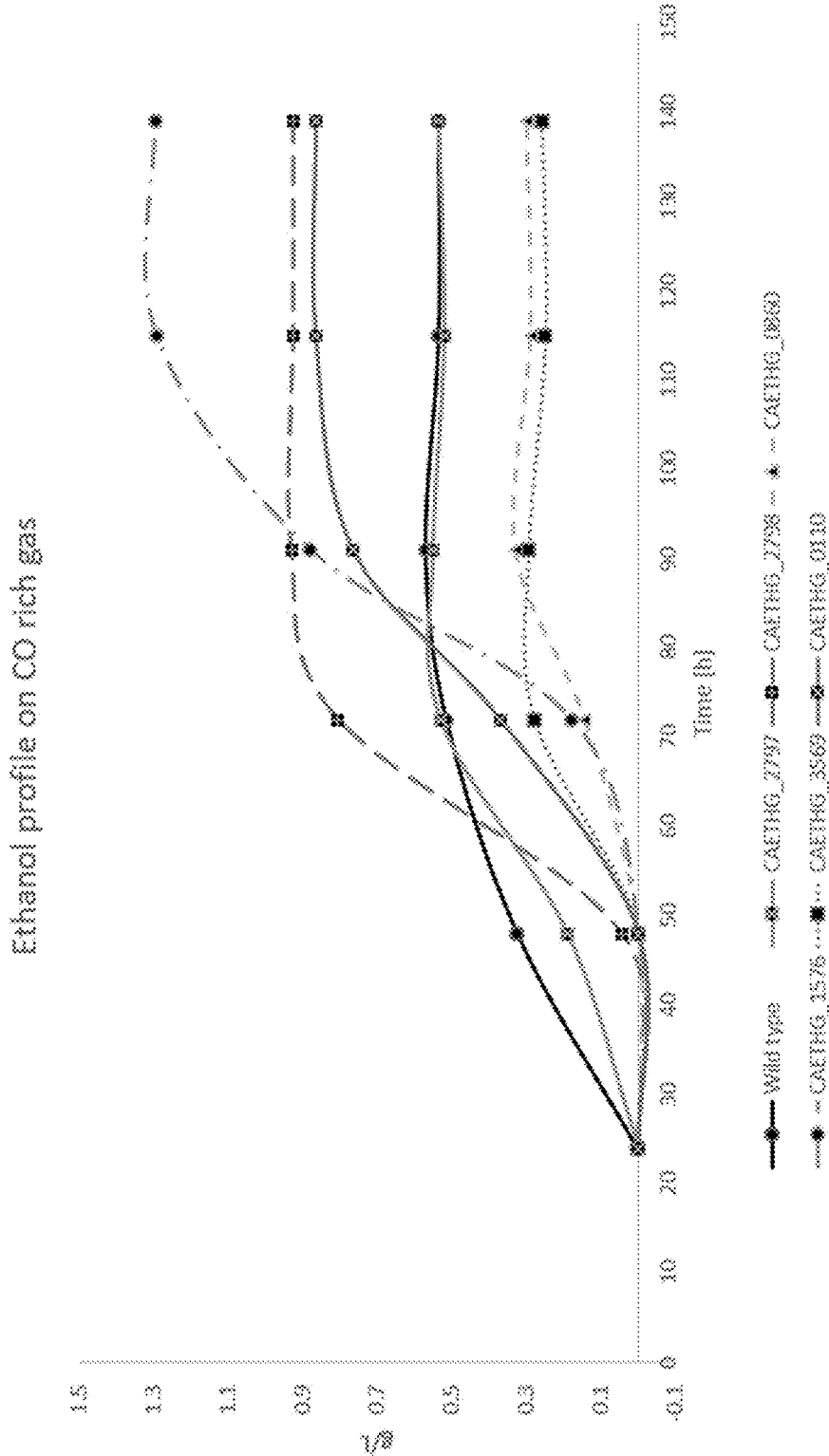

All hydrogenase mutants appear to grow in CO-rich gas, but at different growth rates (FIG. 1A) indicating that all five hydrogenase genes are redundant. The growth of ΔCAETHG_2797-Clone1 and ΔCAETHG_2798-Clone1 mutants is drastically impaired followed by ΔCAETHG_1576-Clone1 and ΔCAETHG_0110-Clone5. This is in accordance with the expression of these hydrogenases in *C. autoethanogenum* LZ1561 where the transcript abundance is CAETHG_2794-99>CAETHG_1576-79>CAETHG_0110 (Mock, *J Bacteriol*, 197: 2965-2980, 2015). A similar trend is observed with acetate production in *C. autoethanogenum* LZ1561 and hydrogenase mutant strains (FIG. 1B). Interestingly, ΔCAETHG_1576-Clone1 surprisingly produces double the ethanol, making up to 1.2 g/L whereas *C. autoethanogenum* LZ1561 only makes only 0.6 g/L (FIG. 1C) under the same conditions.

Example 3

This example profiles growth of *C. autoethanogenum* hydrogenase mutants on a $H_2$-rich gas mix containing 65% $H_2$, 9.2% $N_2$, and 23% $CO_2$.

Figure 2A:
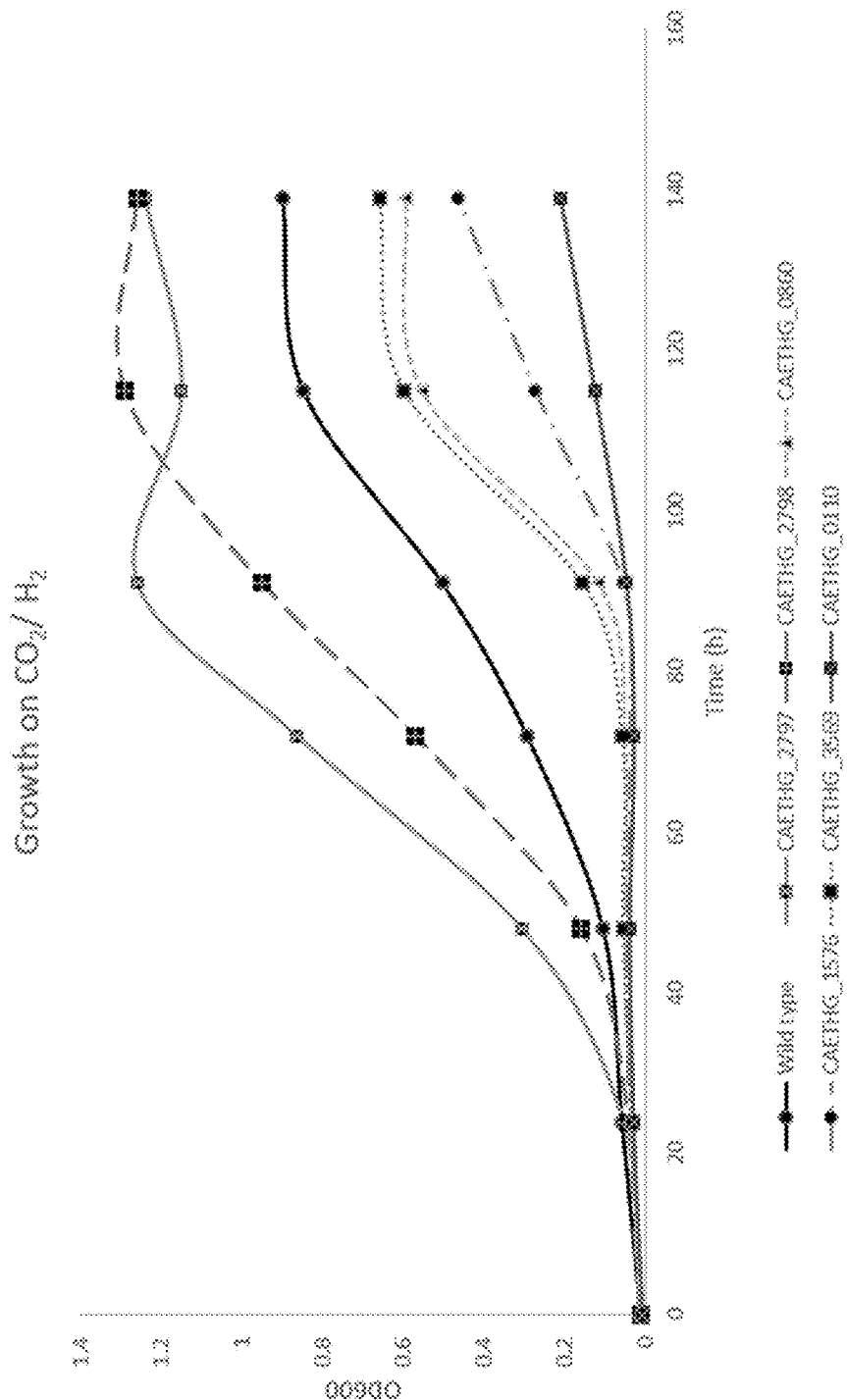
FIGS. 2A-2C are graphs showing the results of growing C. autoethanogenum LZ1561 (control) and C. autoethanogenum mutants CAETHG_1576, CAETHG_2797, CAETHG_3569, CAETHG_2798, CAETHG_0110, and CAETHG_0860 on $H_2$-rich gas, specifically the production of microbial biomass (FIG. 2A), acetate (FIG. 2B), and ethanol (FIG. 2C).
Figure 2B:
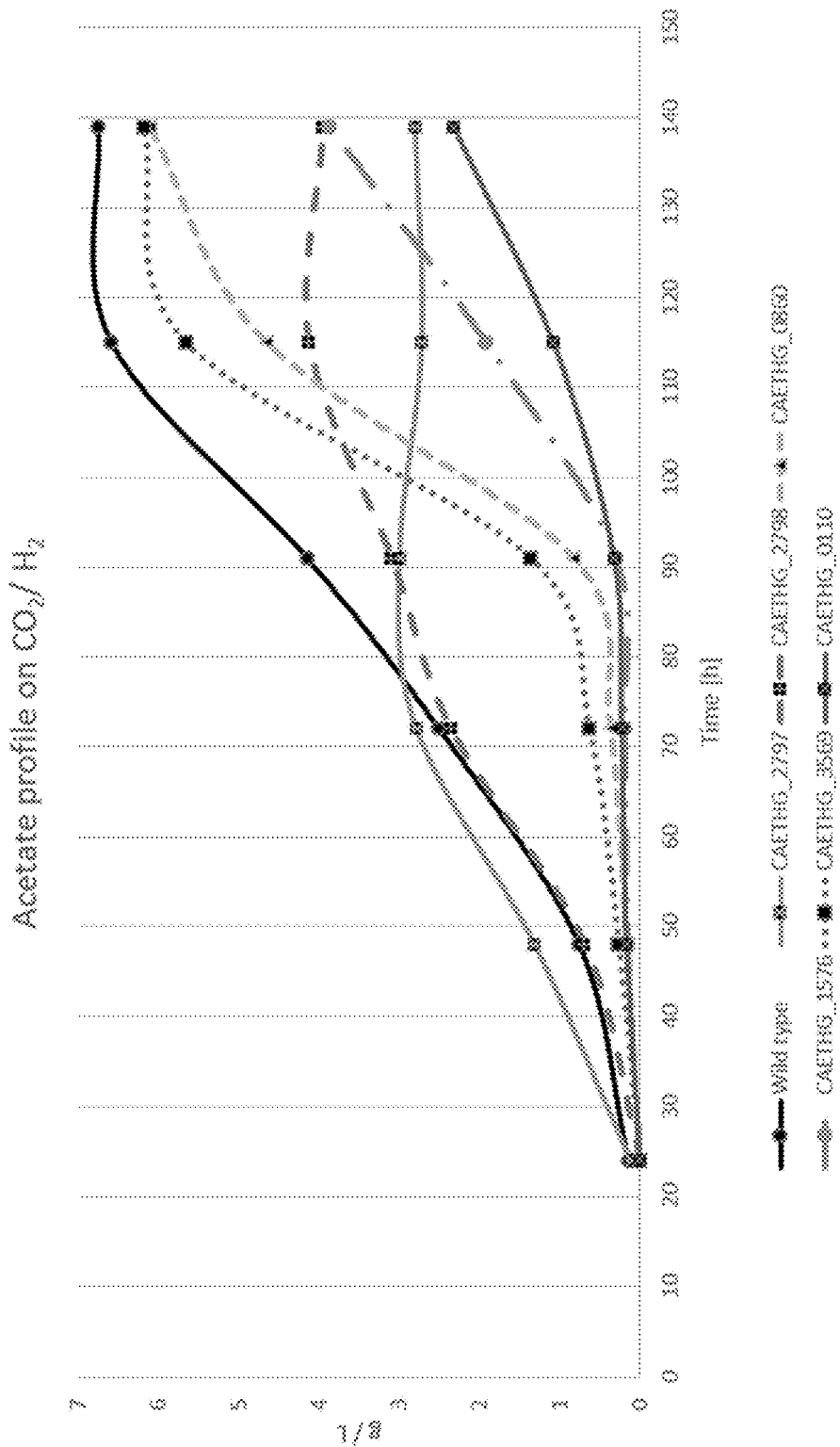
Figure 2C:
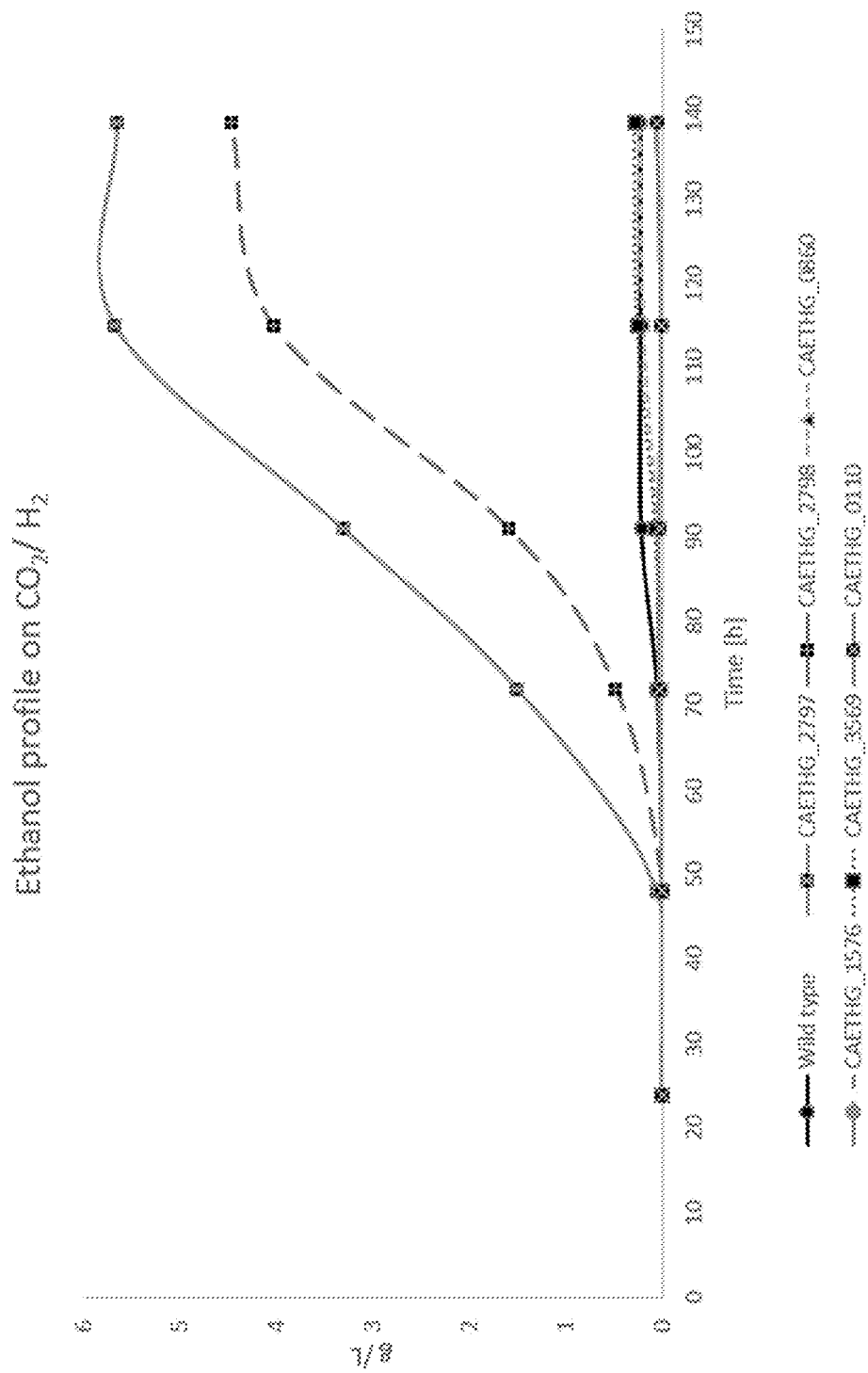

Aside from the gas composition, the experimental setup was similar to that described in Example 2. The growth and metabolite profile of hydrogenase mutants on $H_2$-rich gas is interestingly different from that seen on the CO-rich gas of Example 2. ΔCAETHG_2797-Clone1 and ΔCAETHG_2798-Clone1 mutants grew to an OD600 of 1.2 while *C. autoethanogenum* LZ1561 and other mutants reached an OD600 of 0.8 (FIG. 2A). This implies that, in the absence of functional CAETHG_2794-99 cluster, other hydrogenases that rescue growth of the mutant help the mutant perform better in the $H_2$-rich gas. ΔCAETHG_1576-Clone1 and ΔCAETHG_0110-Clone5 grew poorly under the same conditions (FIG. 2A) indicating that these hydrogenases, CAETHG_1576-79 and CAETHG_0110, may be essential for survival on $H_2$ rich gas. Interestingly, the ΔCAETHG_2797-Clone1 and ΔCAETHG_2798-Clone1 mutants that had better growth, made 20-40% less acetate (3-4 g/L) compared to *C. autoethanogenum* LZ1561 (6.5 g/L) (FIG. 2B) and surprisingly over 20 times (2174%) more ethanol (up to 5 g/L) compared to *C. autoethanogenum* LZ1561 (0.23 g/L) (FIG. 2C) under same conditions.

Example 4

This example describes transcriptomics of *C. autoethanogenum* LZ1561 grown on a $H_2$-rich gas mix.

*C. autoethanogenum* LZ1561 was grown in a bioreactor on a gas mix containing 65% $H_2$, 25% $CO_2$, 6% $N_2$, and 4% according to the methods described in Mock, *J Bacteriol*, 197: 2965-2980, 2015. The cell pellets were harvested at steady state to investigate the expression of heptameric Hyt hydrogenase (HytABCDE1E2; CATHEG 2794-99) and trimeric Hyd hydrogenase over the course of 23 days using RNA transcriptomics (RNASeq) according to Marcellin, Low carbon fuels and commodity chemicals from waste gases—systematic approach to understand energy metabolism in a model acetogen, *Green Chem*, 2016.

From the RNASeq data, it was evident that expression of the heptameric Hyt remained relatively stable from days 0-23. Hyt was the most highly expressed hydrogenase until day 10. However the expression of trimeric Hyd cluster, which was the second most highly expressed hydrogenase until about day 10, increased by approximately 5 fold between days 7 and 10 to reach similar levels of expression as Hyt. In contrast, the expression of Hyd did not change over time in cells growth on a CO-rich gas mix rather than a $H_2$-rich gas mix (Mock, *J Bacteriol*, 197: 2965-2980, 2015 and Marcellin, Low carbon fuels and commodity chemicals from waste gases—systematic approach to understand energy metabolism in a model acetogen, *Green Chem*, 2016).

The increase in expression of Hyd on a $H_2$-rich gas mix implies that Hyd plays a role in $H_2$ uptake.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A genetically engineered C1-fixing microorganism comprising a disruptive mutation in an electron-bifurcating, NADP- and ferredoxin dependent [FeFe]-hydrogenase; wherein the electron-bifurcating, NADP- and ferredoxin dependent [FeFe]-hydrogenase is CAETHG_2794-99 (HytABCDE1E2) or a homologue thereof, wherein the microorganism is derived from *Clostridium autoethanogenum*, *Clostridium ljungdahlii*, or *Clostridium ragsdalei*.

2. The microorganism of claim 1, wherein the CAETHG_2794-99 (HytABCDE1E2) comprises a disruptive mutation in one or more of subunits HytA, HytB, HytC, HytD, HytE1, and HytE2.

3. The microorganism of claim 1, wherein the microorganism consumes a gaseous substrate comprising a C1-carbon source comprising $CO_2$.

4. The microorganism of claim 1, wherein the microorganism consumes a gaseous substrate comprising a C1-carbon source comprising CO.

5. The microorganism of claim 1, wherein the microorganism is capable of net carbon capture.

6. A method of producing a product comprising culturing the microorganism of claim 1 in the presence of a gaseous substrate, whereby the microorganism produces the product, wherein the product is one or more of acetate, ethanol, and 2,3-butanediol.

7. The method of claim 6, wherein the gaseous substrate comprises a C1-carbon source comprising $CO_2$ and/or CO.

8. A method of fixing carbon comprising culturing the microorganism of claim 1 in the presence of a gaseous substrate comprising a C1-carbon source, whereby the microorganism consumes more C1-carbon than it produces.

9. The method of claim 8, wherein the gaseous substrate comprising the C1-carbon source comprises $CO_2$ and/or CO.

10. The method of claim 6, wherein the microorganism produces more ethanol than a parental microorganism without the disruptive mutation.

11. The method of claim 7 or claim 9, wherein the gaseous substrate further comprises $H_2$.

* * * * *

SEQUENCE LISTING

<160> NUMBER OF SEQ ID NOS: 71

<210> SEQ ID NO 1
<211> LENGTH: 161
<212> TYPE: PRT
<213> ORGANISM: Clostridium autoethanogenum
<220> FEATURE:
<221> NAME/KEY: MISC_FEATURE
<223> OTHER INFORMATION: CAETHG_2794, NADH-quinone oxidoreductase, E
      subunit (EC:1.6.99.5)

<400> SEQUENCE: 1

Met Leu Thr Lys Gln Gln Asn Glu Asp Leu Ser Gly Gln Asp Val Ile
1               5                   10                  15

Glu Lys Tyr Pro Lys Glu Gln Arg Phe Thr Leu Ala Ile Leu Gln Asp
            20                  25                  30

Ile Gln Arg Lys Tyr Lys Tyr Ile Pro Arg Glu Ala Leu Glu Asn Leu
        35                  40                  45

Ala Lys Tyr Leu Asp Thr Pro Val Ser Arg Leu Tyr Gly Met Ala Thr
    50                  55                  60

Phe Tyr Lys Ala Leu Ser Leu Thr Pro Lys Gly Glu Asn Ile Ile Thr
65                  70                  75                  80

Val Cys Asp Gly Thr Ala Cys His Val Ala Gly Ser Met Val Met
                85                  90                  95

Asp Glu Leu Glu Lys Ala Ile Gly Ile Lys Pro Gly Glu Thr Thr Glu
            100                 105                 110

Asp Leu Lys Phe Ser Ile Asn Thr Val Asn Cys Ile Gly Cys Cys Ala
        115                 120                 125

Ile Ala Pro Val Met Met Ile Asn Asp Lys Tyr Tyr Gly Asn Leu Thr
    130                 135                 140

Pro Lys Leu Val Glu Glu Ile Leu Ser Glu Tyr Arg Ser Glu Ser Asp
145                 150                 155                 160

Glu

<210> SEQ ID NO 2
<211> LENGTH: 486
<212> TYPE: DNA
<213> ORGANISM: Clostridium autoethanogenum
<220> FEATURE:
<221> NAME/KEY: misc_feature
<223> OTHER INFORMATION: CAETHG_2794, NADH-quinone oxidoreductase, E
      subunit (EC:1.6.99.5)

<400> SEQUENCE: 2
atgttaacta acagcaaaa tgaagacctg tctggacaag atgtaattga aaaatatcct        60
aaagagcaga gatttactct tgctatacta caggatatac agagaaagta caatatata       120 ccaagagaag cactggagaa tttagctaag tatttggaca cgcctgtaag tagactgtat      180
ggtatggcta cttttttataa ggcattgagc cttactccaa aggggaaaaa cataataact    240
gtatgtgatg gaaccgcttg ccatgttgct ggttctatgg ttgtaatgga tgaacttgaa     300
aaggcaatag gaattaaacc aggtgaaact acagaggatc tcaaattttc aataaataca    360
gttaactgta taggatgctg tgcaatagct cctgtcatga tgataaatga caaatattat   420
ggaaatttaa cacctaaact ggttgaagaa attcttagtg agtataggag tgagagtgat   480
gagtga                                                                486

<210> SEQ ID NO 3
<211> LENGTH: 599

```
<212> TYPE: PRT
<213> ORGANISM: Clostridium autoethanogenum
<220> FEATURE:
<221> NAME/KEY: MISC_FEATURE
<223> OTHER INFORMATION: CAETHG_2795, NADH dehydrogenase (quinone)
      (EC:1.6.99.5)

<400> SEQUENCE: 3

Met Ser Asp Lys Lys Thr Val Asn Ile Cys Cys Gly Thr Gly Cys Leu
1               5                   10                  15

Ala Lys Gly Ser Met Glu Val Tyr Glu Met Lys Ala Gln Ile Ala
            20                  25                  30

Lys Leu Gly Ala Asn Ala Glu Val Asn Val Lys Leu Lys Ala Thr Gly
            35                  40                  45

Cys Asp Gly Leu Cys Glu Lys Gly Pro Val Leu Lys Ile Tyr Pro Asp
        50                  55                  60

Asp Ile Ala Tyr Phe Lys Val Lys Val Glu Asp Val Glu Asp Val Val
65                  70                  75                  80

Lys Lys Thr Leu Met Asn Gly Glu Ile Ile Glu Lys Leu Leu Tyr Phe
                85                  90                  95

Glu Thr Ala Thr Lys Gln Arg Leu Arg Asn His Lys Glu Ser Glu Phe
            100                 105                 110

Cys Lys Arg Gln Tyr Lys Ile Ala Leu Arg Asn Val Gly Glu Ile Asp
        115                 120                 125

Pro Ile Ser Leu Glu Asp Tyr Val Glu Arg Gly Gly Tyr Lys Ala Leu
    130                 135                 140

Lys Lys Ala Ile Ser Ser Met Lys Pro Glu Asp Val Leu Glu Glu Ile
145                 150                 155                 160

Thr Lys Ser Gly Leu Arg Gly Arg Gly Gly Ala Gly Phe Pro Thr Gly
                165                 170                 175

Arg Lys Trp Lys Thr Ala Ala Asp Ile Asp Thr Ser Pro Ile Tyr Val
            180                 185                 190

Val Cys Asn Gly Asp Glu Gly Asp Pro Gly Ala Phe Met Asp Arg Ser
        195                 200                 205

Ile Met Glu Gly Asp Pro Asn Ser Val Ile Glu Gly Met Thr Leu Cys
    210                 215                 220

Ala Tyr Ala Val Gly Gly Thr Asn Gly Phe Ala Tyr Ile Arg Asp Glu
225                 230                 235                 240

Tyr Gly Leu Ala Val Glu Asn Met Gln Lys Ala Ile Asn Lys Ala Lys
                245                 250                 255

Asp Glu Asn Leu Leu Gly Asn Asn Ile Leu Gly Thr Asp Phe Ser Phe
            260                 265                 270

Asp Ile Gln Ile Val Arg Gly Gly Ala Phe Val Cys Gly Glu Ser
        275                 280                 285

Thr Ala Leu Met Ser Ser Ile Glu Gly Met Val Gly Glu Pro Arg Ala
    290                 295                 300

Lys Tyr Ile His Thr Thr Glu Lys Gly Leu Trp Gly Gln Pro Thr Val
305                 310                 315                 320

Leu Asn Asn Val Glu Thr Trp Ala Asn Val Pro Ile Ile Glu Lys
                325                 330                 335

Gly Gly Asp Trp Tyr His Ala Ile Gly Thr Met Glu Lys Ser Lys Gly
            340                 345                 350

Thr Lys Val Phe Ser Leu Val Gly Lys Val Lys Asn Thr Gly Leu Val
        355                 360                 365

Glu Val Pro Met Gly Thr Thr Leu Arg Glu Ile Ile Tyr Asp Ile Gly
```

```
    370                 375                 380

Gly Gly Val Leu Asn Asp Arg Lys Phe Lys Ala Val Gln Ile Gly Gly
385                 390                 395                 400

Pro Ser Gly Gly Cys Leu Pro Ala Glu Tyr Leu Asp Leu Pro Val Asp
                405                 410                 415

Tyr Asp Thr Leu Val Lys Ala Asp Ser Met Met Gly Ser Gly Gly Met
            420                 425                 430

Ile Val Met Asp Asp Arg Thr Cys Met Val Asp Val Thr Arg Tyr Tyr
        435                 440                 445

Leu Ser Phe Leu Ala Glu Glu Ser Cys Gly Lys Cys Val Pro Cys Arg
    450                 455                 460

Glu Gly Val Lys Arg Met Leu Glu Ile Leu Thr Asp Ile Cys Asn Gly
465                 470                 475                 480

Asp Gly Lys Glu Gly Asp Ile Glu Glu Leu Leu Glu Ile Cys Ser Met
                485                 490                 495

Thr Ser Lys Ala Ser Leu Cys Ser Leu Gly Lys Ser Ala Pro Asn Pro
            500                 505                 510

Val Ile Ala Ser Ile Arg Tyr Phe Arg Asp Glu Phe Glu Glu His Ile
        515                 520                 525

Lys Asn Lys Arg Cys Arg Ala Gly Val Cys Lys Lys Leu Thr Thr Phe
    530                 535                 540

Gly Ile Asp Glu Asp Lys Cys Lys Gly Cys Asp Met Cys Lys Lys Asn
545                 550                 555                 560

Cys Pro Ala Asp Cys Ile Thr Gly Glu Ile Lys Lys Pro His Thr Ile
                565                 570                 575

Asp Ala Asp Lys Cys Leu Arg Cys Gly Asn Cys Met Asn Ile Cys Lys
            580                 585                 590

Phe Asp Ala Val Lys Val Leu
        595

<210> SEQ ID NO 4
<211> LENGTH: 1800
<212> TYPE: DNA
<213> ORGANISM: Clostridium autoethanogenum
<220> FEATURE:
<221> NAME/KEY: misc_feature
<223> OTHER INFORMATION: CAETHG_2795, NADH dehydrogenase (quinone)
      (EC:1.6.99.5)

<400> SEQUENCE: 4
atgagtgata aaaaaactgt caatatatgt tgtgggacag gttgtttagc taaaggcagt      60
atggaagtat atgaagaaat gaaggcacaa atagctaaat taggggcaaa tgcagaagta     120
aatgttaaat taaaagcaac aggttgcgat ggattgtgtg agaaaggtcc tgtactgaaa     180
atatatccag atgacattgc atattttaaa gttaaagtag aagatgtaga agacgtagta     240
aaaaagacat tgatgaatgg ggaaataatt gaaaaattat tatattttga gactgctaca     300
aaacagagat taagaaatca taaagaaagt gaattttgta aaagacaata caaaattgct     360
ctcagaaatg ttggtgaaat agatccaata agtttggaag attatgttga aagaggcgga     420
tacaaagctc ttaaaaaagc aataagcagc atgaaacctg aagatgtgct tgaagaaata     480
acaaaatcag gtcttagagg aagaggtgga gcaggattcc caacaggacg taaatggaaa     540
actgctgcag atattgatac atcacctata tatgtagtat gtaatggtga tgaaggagat     600
cctggagcat ttatggatag aagtataatg gagggagatc ctaacagtgt tatagaaggt     660
atgacattat gtgcttatgc agtaggaggt acaaatggat ttgcttatat aagagatgaa     720
```

```
tatggacttg ctgtagaaaa tatgcagaaa gctattaata aagcaaaaga tgaaaattta      780
ttaggtaata atatattagg aactgatttt tccttcgata tacagatagt aagaggtgga      840
ggagcttttg tatgtggtga atctactgca cttatgtcgt ctatagaagg tatggtaggt      900
gaacctagag ctaaatatat acacactaca gaaaaaggat tgtggggaca acctacagtt      960
ttaaataatg tagaaacttg ggccaatgta cctataataa ttgaaaaagg cggagattgg     1020
tatcatgcta taggaactat ggagaagagt aagggaacaa aggtattctc attagttgga     1080
aaagttaaga atactggact tgtagaagta cctatgggaa ctactcttag agaaataata     1140
tatgatattg gcggtggagt attaaatgat agaaagttta aggcagttca aataggtgga     1200
ccttcaggtg gatgtttacc agctgaatat ttagatttgc cagtagatta tgatactttg     1260
gttaaagcag attccatgat gggttcaggc ggaatgatcg taatggatga tagaacctgt     1320
atggtagatg taactagata ttacctgagc ttcttggctg aagaatcttg tggaaagtgt     1380
gtaccttgta gagaaggcgt aaagaggatg cttgaaatac tcactgacat atgcaatggt     1440
gatggaaaag aaggagacat agaagagctt ctcgaaatat gttccatgac aagcaaggca     1500
tctctgtgca gtcttggtaa gagtgctcca aatccagtaa ttgcttctat aagatatttt     1560
agagatgaat ttgaagagca tataaagaat aagagatgta gagcaggagt ttgtaagaaa     1620
cttactacat ttggtataga cgaggataaa tgtaagggat gcgatatgtg taaaaagaat     1680
tgtccagctg attgtataac aggggaaatt aagaaaccac atacaataga tgctgataag     1740
tgcttgagat gcggtaactg catgaacatc tgtaagtttg atgctgttaa ggttctatag     1800
```

<210> SEQ ID NO 5
<211> LENGTH: 251
<212> TYPE: PRT
<213> ORGANISM: Clostridium autoethanogenum
<220> FEATURE:
<221> NAME/KEY: MISC_FEATURE
<223> OTHER INFORMATION: CAETHG_2796, 4Fe-4S ferredoxin, iron-sulfur
      binding domain-containing protein

<400> SEQUENCE: 5

```
Met Lys Ile Thr Ile Asp Gly Lys Ala Cys Glu Ala Glu Lys Gly Glu
1               5                   10                  15

Phe Ile Leu Gln Ile Ala Arg Arg Asn Asn Ile Tyr Ile Pro Thr Leu
                20                  25                  30

Cys His Ser Asp Ala Leu Pro Gly Leu Ala Ser Cys Arg Leu Cys Ile
            35                  40                  45

Val Lys Val Val Asp Arg Gly Arg Ala Lys Ile Val Thr Ser Cys Ile
        50                  55                  60

Phe Pro Val Ser Lys Glu Val Glu Val Ile Thr Asn Asp Asp Glu Ile
65                  70                  75                  80

Lys Arg Met Arg Lys Asn Ile Val Met Leu Leu Lys Val Arg Cys Pro
                85                  90                  95

Glu Asn Lys Glu Val Asn Glu Leu Ala Lys Ala Phe Gly Val Glu Glu
                100                 105                 110

Lys Arg Val Lys Arg Phe Lys Leu Asp Pro Glu Gln Asn Cys Val Leu
            115                 120                 125

Cys Gly Leu Cys Ala Lys Ala Cys Lys Glu Leu Gly Thr Gly Ala Ile
        130                 135                 140

Ser Thr Val Asn Arg Gly Met Tyr Lys Glu Val Ala Thr Pro Tyr His
145                 150                 155                 160
```

```
Glu Ser Ser Pro Glu Cys Ile Gly Cys Ala Ser Cys Ala Asn Val Cys
                165                 170                 175

Pro Thr Asn Ala Ile Lys Val Val Asp Lys Asp Gly Glu Arg Glu Ile
            180                 185                 190

Trp Gly Lys Lys Phe Lys Met Val Lys Cys Asp Leu Cys Gly Glu Tyr
        195                 200                 205

Phe Ala Thr Glu Glu His Val Lys Tyr Ala Tyr Asn Arg Leu Gly Lys
    210                 215                 220

Glu Gln Pro Glu Lys Leu Met Cys Ser Ser Cys Lys Lys Val Thr
225                 230                 235                 240

Ala Lys Asp Val Lys Asn Ile Phe Glu Asn Val
            245                 250

<210> SEQ ID NO 6
<211> LENGTH: 756
<212> TYPE: DNA
<213> ORGANISM: Clostridium autoethanogenum
<220> FEATURE:
<221> NAME/KEY: misc_feature
<223> OTHER INFORMATION: CAETHG_2796, 4Fe-4S ferredoxin, iron-sulpur
      binding domain-containing protein

<400> SEQUENCE: 6
atgaaaatta caatagatgg aaaagcttgt gaagctgaaa aaggagaatt catattacaa      60
atagcaagaa gaaataacat atatatacct acattatgtc acagcgatgc attgcctggg     120
cttgctagct gtagactatg tatagttaaa gtagtagata ggggacgtgc aaagatagta     180
acttcctgta tattccctgt aagtaaggaa gtagaagtta taactaatga cgatgaaata     240
aagagaatga gaaaaaacat agttatgctt ttaaaagtaa gatgccctga aaataaagag     300
gtaaatgaat tagctaaagc ctttggagta gaggaaaaga gagtaaagag gttcaaattg     360
gatccagaac aaaattgtgt tttgtgcgga ctttgtgcaa aagcttgcaa ggaattaggt     420
actggagcaa tttcaacagt taataggggt atgtataaag aagtagcaac tccatatcac     480
gaatcttcac cggaatgtat aggatgtgct cctgtgcaa atgtttgtcc aactaatgca     540
ataaaagttg tggataaaga tggagaaaga gaaatatggg gcaaaaaatt caagatggtt     600
aagtgtgatt tgtgcggaga atattttgct acagaagaac atgtaaaata tgcttacaat     660
aggcttggaa aagagcagcc agaaaaactt atgtgtagca gctgcaagaa gaaagttaca     720
gccaaagatg tcaaaaatat ttttgagaac gtgtga                               756

<210> SEQ ID NO 7
<211> LENGTH: 184
<212> TYPE: PRT
<213> ORGANISM: Clostridium autoethanogenum
<220> FEATURE:
<221> NAME/KEY: MISC_FEATURE
<223> OTHER INFORMATION: CAETHG_2797, 4Fe-4S ferredoxin, iron-sulpur
      binding domain-containing protein, WP_013237376.1

<400> SEQUENCE: 7

Met Lys Pro Glu Phe Asn Ser Phe Val Ile Ala Asp Pro Asp Lys Cys
1               5                   10                  15

Ile Gly Cys Arg Ser Cys Glu Ile Ala Cys Ala Ala Lys His Arg Glu
            20                  25                  30

Asp Thr Gln Gly Lys Thr Ile Gly Thr Met Asn Asn Lys Val Thr Pro
        35                  40                  45

Arg Leu Phe Phe Val Lys Asn Lys Gly Asn Val Met Pro Val Gln Cys
    50                  55                  60
```

Arg His Cys Glu Asp Ala Pro Cys Leu Asn Ala Cys Pro Val Asn Ala
65                  70                  75                  80

Ile Val Glu Lys Asp Gly Ser Ile Ile Ile Asn Glu Ser Ala Cys Ile
            85                  90                  95

Gly Cys Gln Thr Cys Thr Ile Val Cys Pro Val Gly Ala Val Ser Leu
            100                 105                 110

Leu Pro Arg Thr Gln Gly Lys Val Val Thr Gly Gly Ile Gln Val Lys
        115                 120                 125

Val Arg Ala Ala Ala Tyr Lys Cys Asp Leu Cys Lys Glu Glu Gly Gly
130                 135                 140

Glu Pro Ala Cys Val Lys Glu Cys Pro Lys Glu Ala Leu Arg Leu Val
145                 150                 155                 160

Asp Pro Arg Glu Asp Lys Lys Asp Arg Ser Val Lys Ala Ala Met Glu
                165                 170                 175

Leu Leu Asn Ile Asn Ala Asn Leu
            180

<210> SEQ ID NO 8
<211> LENGTH: 555
<212> TYPE: DNA
<213> ORGANISM: Clostridium autoethanogenum
<220> FEATURE:
<221> NAME/KEY: misc_feature
<223> OTHER INFORMATION: CAETHG_2797, 4Fe-4S ferredoxin, iron-sulpur
      binding domain-containing protein

<400> SEQUENCE: 8
atgaaaccag agtttaattc ttttgtaata gccgatcctg acaagtgcat aggctgtaga      60
tcttgtgaga ttgcctgtgc tgcaaaacat agagaagata ctcaaggaaa accattgga     120 actatgaata ataaagttac tccaaggtta ttctttgtta aaaataaagg aaatgtaatg    180
ccagtacaat gcagacattg tgaggatgca ccatgtctaa atgcctgccc agttaatgct    240
atagttgaaa aagatggaag tatcattata aatgaaagtg catgtatagg atgtcagacc    300
tgtacaatag tatgtccggt aggtgctgta agtttactgc ctagaactca aggtaaagta    360
gttacaggag gaattcaggt taaagtaaga gcagcagctt ataaatgtga tttatgtaag    420
gaagagggag agaacctgc ttgcgtcaaa gaatgtccaa agaggccctt gaggttagta     480
gatcctagag aagataaaaa agatcgtagt gtgaaagctg ctatggaact gttaaatata    540
aacgcaaatc tctaa                                                     555

<210> SEQ ID NO 9
<211> LENGTH: 462
<212> TYPE: PRT
<213> ORGANISM: Clostridium autoethanogenum
<220> FEATURE:
<221> NAME/KEY: MISC_FEATURE
<223> OTHER INFORMATION: CAETHG_2798, hydrogenase, Fe-only
      (EC:1.12.7.2), WP_035788218.1

<400> SEQUENCE: 9

Met Pro Thr Ser Thr Ser Met Ile Asn Ile Asp Glu Glu Leu Cys Thr
1               5                   10                  15

Gly Cys Arg Arg Cys Ala Asp Val Cys Pro Val Asp Ala Ile Glu Gly
            20                  25                  30

Glu Gln Gly Lys Pro Gln Lys Ile Asn Thr Glu Lys Cys Val Met Cys
        35                  40                  45

Gly Gln Cys Ile Gln Val Cys Lys Gly Tyr Gln Ser Val Tyr Asp Asp

```
            50                  55                  60
Val Pro Thr Pro Val Ser Lys Arg Leu Phe Asp Arg Gly Leu Leu Lys
 65                  70                  75                  80

Glu Val Asp Glu Pro Leu Phe Ala Ala Tyr Asn Lys Gly Gln Val Lys
                 85                  90                  95

Ser Val Lys Glu Ile Leu Gln Asn Lys Asp Val Phe Lys Ile Val Gln
            100                 105                 110

Cys Ala Pro Ala Val Arg Val Ala Ile Gly Glu Asp Phe Gly Met Pro
            115                 120                 125

Leu Gly Thr Leu Ser Glu Gly Lys Met Ala Ala Leu Arg Lys Leu
        130                 135                 140

Gly Phe Asp Lys Val Tyr Asp Thr Asn Phe Gly Ala Asp Leu Thr Ile
145                 150                 155                 160

Met Glu Glu Gly Ser Glu Leu Leu Lys Arg Val Ala Glu Gly Gly Val
                165                 170                 175

Leu Pro Met Phe Thr Ser Cys Cys Pro Ala Trp Val Lys Tyr Ala Glu
            180                 185                 190

Gln Thr Tyr Pro Glu Leu Leu Pro His Leu Ser Ser Cys Lys Ser Pro
        195                 200                 205

Asn Gln Met Ala Gly Ala Ile Phe Lys Thr Tyr Gly Ala Glu Ile Asn
    210                 215                 220

Lys Val Asn Pro Ala Lys Ile Tyr Asn Val Ser Val Met Pro Cys Thr
225                 230                 235                 240

Cys Lys Glu Phe Glu Ser Glu Arg Glu Met His Asp Ser Gly His
                245                 250                 255

Arg Asp Val Asp Ala Val Ile Thr Thr Arg Glu Leu Ala Gln Leu Phe
                260                 265                 270

Lys Asp Ala Asp Ile Asp Phe Asn Thr Ile Glu Glu Gln Phe Asp
                275                 280                 285

Thr Pro Leu Gly Met Tyr Thr Gly Ala Gly Thr Ile Phe Gly Ala Thr
        290                 295                 300

Gly Gly Val Met Glu Ala Ala Leu Arg Thr Gly Tyr Glu Leu Tyr Thr
305                 310                 315                 320

Lys Lys Thr Ile Pro Ser Ile Asp Leu Thr Met Val Arg Gly Gly Glu
            325                 330                 335

Gly Phe Arg Thr Ala Glu Val Asp Leu Gly Asp Ile Arg Leu Lys Val
            340                 345                 350

Gly Val Val Ser Gly Leu Lys Asn Val Lys Asp Val Met Glu Ser Val
            355                 360                 365

Lys Ala Gly Lys Cys Asp Leu His Phe Ile Glu Val Met Thr Cys Pro
    370                 375                 380

Gln Gly Cys Ile Ser Gly Gly Gln Pro Lys Val Ile Leu Asp Ser
385                 390                 395                 400

Asp Lys Glu Glu Ala Tyr Asn Asn Arg Lys Lys Gly Leu Tyr Asn His
                405                 410                 415

Asp Ala Asn Leu Thr Tyr Arg Lys Ser His Glu Asn Pro Glu Ile Lys
                420                 425                 430

Lys Ile Tyr Asp Glu Phe Leu Asp Lys Pro Leu Gly Ala Lys Ser His
            435                 440                 445

Glu Leu Leu His Thr Lys Tyr Ile Ser Arg Lys Lys Glu Ser
    450                 455                 460

<210> SEQ ID NO 10
```

-continued

```
<211> LENGTH: 1389
<212> TYPE: DNA
<213> ORGANISM: Clostridium autoethanogenum
<220> FEATURE:
<221> NAME/KEY: misc_feature
<223> OTHER INFORMATION: CAETHG_2798, hydrogenase, Fe-only (EC:1.12.7.2)

<400> SEQUENCE: 10
atgccaacta gtacttctat gataaatata gatgaagaat tatgtacagg ctgcagacga      60
tgtgcggatg tctgccctgt agatgctata gaaggtgaac agggtaaacc tcagaagata     120
aatactgaaa agtgtgttat gtgcggacaa tgcattcaag tttgtaaagg ctatcaatct     180
gtatacgacg atgttcctac tccagttagc aaaaggttat ttgatagagg attgttaaag     240
gaagtagatg aaccattatt tgcagcatat aataaaggtc aggtaaagag tgttaaagaa     300
attttacaaa acaagatgtg attttaaaatt gtgcaatgtg cacctgctgt aagagttgct     360
ataggagagg attttggaat gcctcttgga actttaagtg aaggaaaaat ggcagctgca     420
ctcagaaaat taggatttga caaagtatat gatacaaact tggtgcaga tcttactata      480
atggaagaag gtagtgagtt actaaaaaga gtagctgaag gcggagtttt gccaatgttt     540
acttcttgtt gtccagcatg ggtaaaatat gcagaacaaa catatccaga acttttacct     600
catctttcaa gttgtaagtc tccaaatcag atggctggag ctatatttaa aacttatgga     660
gcagagataa ataaggttaa tccggctaaa atttataatg tatctgttat gccatgtaca     720
tgcaaggaat ttgaaagtga aagagaagaa atgcatgaca gtggacacag ggatgtagat     780
gcagttataa ctacaaggga attagcacaa ctgttcaaag atgctgatat agattttaat     840
actattgaag aagaacagtt tgatactcct cttggtatgt ataccggtgc aggaactata     900
tttggtgcta caggtggagt tatggaagca gcacttagaa ctggatatga actttatact     960
aaaaaaacta ttccaagtat agatcttact atggtaagag gtggagaagg ttttagaact    1020
gctgaagtag atttagggga tattagacta aagtaggag tagtttccgg cttaaaaaat    1080
gtaaagacg ttatggaatc agtaaaggca ggcaaatgtg atttgcactt tatagaggtt    1140
atgacctgtc ctcaaggatg tataagtggt ggaggacaac ctaaagttat acttgattca    1200
gataaagagg aagcttataa taataggaaa aagggactat ataatcatga cgctaatctt    1260
acttatagaa aatcacatga aaatccagaa ataagaaaaa tatatgatga gttcttagac    1320
aaaccattag gagctaagtc tcatgaatta ttgcacacta atatatctc aagaaaaaag     1380
gagagttaa                                                            1389

<210> SEQ ID NO 11
<211> LENGTH: 205
<212> TYPE: PRT
<213> ORGANISM: Clostridium autoethanogenum
<220> FEATURE:
<221> NAME/KEY: MISC_FEATURE
<223> OTHER INFORMATION: CAETHG_2799, 4Fe-4S ferredoxin, iron-sulpur
      binding domain-containing protein

<400> SEQUENCE: 11

Met Asn Tyr Cys Thr Leu Asn Ile Ser Gln Glu Lys Arg Arg Val Asn
1               5                   10                  15

Lys Met Lys Asn Cys Leu Val Val Ala Asp Pro Asn Lys Cys Ile Gly
            20                  25                  30

Cys Arg Thr Cys Glu Ala Ala Cys Gly Ile Ala His Ser Gly Gly Asp
        35                  40                  45

Phe Phe Asn Thr Asn Val Ser Lys Ile Asn Phe Asn Pro Arg Leu Asn
```

```
                50                  55                  60
Val Ile Lys Thr Ala Lys Val Ser Ala Pro Val Gln Cys Arg Gln Cys
 65                  70                  75                  80

Glu Asp Ala Pro Cys Gly Lys Ala Cys Pro Val Asn Ala Ile Ser Asn
                 85                  90                  95

Glu Asn Gly Tyr Val Ser Val Asn Lys Asp Val Cys Val Gly Cys Lys
            100                 105                 110

Ile Cys Met Leu Ala Cys Pro Phe Gly Ala Ile Glu Leu Ala Ser Gln
        115                 120                 125

Tyr Arg Asp Gly Glu Val Val Asp Gln Lys Gly Leu Lys Met Ser Glu
    130                 135                 140

Glu Gly Asn Pro Thr Val Asn Gly Lys Gly Arg Val Val Ala Asn Lys
145                 150                 155                 160

Cys Asp Leu Cys Gln Asp Arg Asp Gly Gly Pro Ala Cys Ile Glu Val
                165                 170                 175

Cys Pro Thr Lys Ser Leu Lys Leu Val Thr Tyr Asp Asp Asn Asn Asn
            180                 185                 190

Ile Val Glu Lys Lys Asp Asp Asp Glu Arg Glu Val Ser
        195                 200                 205

<210> SEQ ID NO 12
<211> LENGTH: 618
<212> TYPE: DNA
<213> ORGANISM: Clostridium autoethanogenum
<220> FEATURE:
<221> NAME/KEY: misc_feature
<223> OTHER INFORMATION: CAETHG_2799, 4Fe-4S ferredoxin, iron-sulpur
      binding domain-containing protein

<400> SEQUENCE: 12
atgaattatt gcacactaaa tatatctcaa gaaaaaagga gagttaataa aatgaagaat        60
tgcctcgtag tagcagatcc taataaatgc ataggatgta ggacttgtga agcagcttgt       120
ggtattgcac attcaggagg ggacttttt aacacaaatg tatccaagat taatttttaat      180 cctcgcttaa atgtgataaa aactgctaaa gtaagtgctc ctgttcaatg cagacaatgc       240
gaagatgcac cttgtggtaa agcttgtcca gttaacgcta tttcaaatga aaatggttat       300
gttagtgtaa ataaagatgt atgtgttgga tgtaaaatct gcatgttagc ttgtcctttt       360
ggagctattg aattagcttc tcaatatagg gatggagaag ttgtagacca aaagggactt       420
aagatgagtg aggaaggtaa tcctactgtg aatggaaaag gaagagtggt agcaaataag       480
tgtgatctct gccaggatag ggatggaggg cctgcttgta tagaagtttg tcctacaaaa       540
tctctcaaac tagttactta tgatgacaat aataatatag ttgaaaaaaa agatgacgac       600
gaacgtgaag taagctaa                                                    618

<210> SEQ ID NO 13
<211> LENGTH: 346
<212> TYPE: PRT
<213> ORGANISM: Clostridium autoethanogenum
<220> FEATURE:
<221> NAME/KEY: MISC_FEATURE
<223> OTHER INFORMATION: CAETHG_1691, (FeFe)-hydrogenase maturation
      HydE, radical SAM

<400> SEQUENCE: 13

Met Gly Asp Lys Leu Leu Glu Ser Ile Glu Lys Ala Glu Leu Asn His
  1               5                  10                  15

Thr Leu Asp Lys Ser Glu Ile Val Glu Leu Phe Asn Ser Asn Glu His
```

```
            20                  25                  30
Asn Glu Glu Leu Phe Lys Ala Ala Asp Arg Val Arg Lys Lys Tyr Val
            35                  40                  45
Gly Asp Glu Val His Leu Arg Gly Leu Ile Glu Phe Ser Asn Ile Cys
        50                  55                  60
Lys Arg Asn Cys Met Tyr Cys Gly Leu Arg Arg Asp Asn Lys Asn Ile
 65                  70                  75                  80
Lys Arg Tyr Arg Ile Glu Pro Asp Lys Ile Ile Glu Leu Ala Lys Lys
                85                  90                  95
Ala Val Gly Tyr Gly Tyr Lys Thr Val Val Leu Gln Ser Gly Glu Asp
            100                 105                 110
Asp Tyr Tyr Thr Val Asp Lys Leu Lys Tyr Ile Ile Ser Asn Met Lys
            115                 120                 125
Lys Met Asp Ile Ala Val Thr Leu Ser Ile Gly Glu Lys Thr Phe Glu
    130                 135                 140
Glu Tyr Lys Ala Phe Lys Glu Ala Gly Ala Asp Arg Tyr Leu Ile Arg
145                 150                 155                 160
Ile Glu Thr Thr Asp Pro Glu Leu Tyr Ala Lys Met Asp Pro Gly Met
                165                 170                 175
Ser Tyr Glu Asn Arg Lys Arg Cys Leu Lys Asp Leu Gly Lys Leu Gly
            180                 185                 190
Tyr Glu Val Gly Thr Gly Cys Leu Ile Gly Leu Pro Gly Gln Thr Phe
        195                 200                 205
Glu Ser Leu Ala Glu Asp Ile Leu Phe Phe Lys Glu Ile Asp Ala Asp
    210                 215                 220
Met Val Gly Val Gly Pro Phe Ile Pro Asn Ala Asp Thr Pro Leu Arg
225                 230                 235                 240
Asp Glu Lys Gly Gly Thr Phe Ile Asn Ala Leu Lys Val Met Ala Ile
                245                 250                 255
Ser Arg Leu Ile Met Pro Asp Ile Asn Leu Pro Gly Thr Thr Ala Met
            260                 265                 270
Glu Thr Leu Asn Pro Arg Gly Arg Thr Ile Ala Leu Gln Ser Gly Ala
        275                 280                 285
Asn Val Val Met Pro Asn Val Thr Glu Gly Val Tyr Arg Lys Leu Tyr
    290                 295                 300
Ala Leu Tyr Pro Gly Lys Ile Cys Thr Gly Asp Thr Pro Ala Gln Cys
305                 310                 315                 320
Arg Asp Cys Ile Thr Gly Lys Ile Ile Thr Ile Gly Arg Val Ile Ser
                325                 330                 335
Gly Ser Lys Gly Phe Arg Val Lys Asn Ser
            340                 345
```

<210> SEQ ID NO 14
<211> LENGTH: 1041
<212> TYPE: DNA
<213> ORGANISM: Clostridium autoethanogenum
<220> FEATURE:
<221> NAME/KEY: misc_feature
<223> OTHER INFORMATION: CAETHG_1691, (FeFe)-hydrogenase maturation
    HydE, radical SAM

<400> SEQUENCE: 14
atgggggata aattactaga atcaattgaa aaagctgaat tgaatcatac acttgataaa    60
agtgaaatag ttgaattatt taacagtaac gaacataatg aagaactttt taaagcggca   120
gacagagtaa gaaaaaaata tgtaggggat gaagtacatt taagaggact gatagaattt   180

```
tctaatatat gcaaaagaaa ttgcatgtac tgtggactta gacgtgataa taaaaatatc    240
aaaagatata gaatagagcc ggataaaata attgaattag caaaaaaagc agtaggatac    300
ggctataaaa cagttgtttt gcagtctgga gaagacgatt actatactgt agataagcta    360
aaatacataa tatcaaatat gaagaaaatg gacatagctg taactctcag cataggtgaa    420 aaaactttg aggagtataa agcttttaaa gaagctggag cagatagata tttaataaga     480
atagaaacta cggatccgga actgtatgca aaaatggacc ctgggatgag ttatgaaaat    540
agaaaacgct gcttgaaaga tcttggaaag ttaggatatg aagttggtac aggatgtctt    600
ataggtcttc ctggccaaac ttttgagtcg cttgcagagg atatattatt ttttaaagaa    660
atagatgcag atatggtagg agtagggcct tttattccaa atgcagatac gcctttaaga    720
gatgaaaaag gtggaacgtt tataaatgct cttaaagtta tggctataag cagactaatt    780
atgccagata ttaatcttcc tggtacaaca gctatggaaa ctttaaatcc aagaggcagg    840
actatagctc ttcagagtgg agctaatgta gttatgccaa atgtaacgga aggtgtatat    900
aggaagcttt atgcactata tccaggtaaa atttgcacag gggatactcc tgcccaatgc    960
agagattgta taaccggtaa aataattact ataggaaggg tcatatctgg ttctaaagga   1020
tttagagtaa aaaatagttg a                                             1041
```

<210> SEQ ID NO 15
<211> LENGTH: 411
<212> TYPE: PRT
<213> ORGANISM: Clostridium autoethanogenum
<220> FEATURE:
<221> NAME/KEY: MISC_FEATURE
<223> OTHER INFORMATION: CAETHG_2063, (FeFe)-hydrogenase H-cluster maturation GTPase HydF

<400> SEQUENCE: 15

```
Met Ser Leu Asn Glu Thr Pro Arg Ser Val Arg Thr His Ile Ala Leu
1               5                   10                  15

Phe Gly Lys Arg Asn Ala Gly Lys Ser Ser Ile Ile Asn Ala Leu Thr
            20                  25                  30

Gly Gln Asp Ile Ala Ile Val Ser Asp Val Arg Gly Thr Thr Thr Asp
        35                  40                  45

Pro Val Tyr Lys Ser Met Glu Ile Leu Pro Ile Gly Pro Cys Val Ile
    50                  55                  60

Ile Asp Thr Ala Gly Leu Asp Asp Glu Gly Glu Leu Gly Glu Leu Arg
65                  70                  75                  80

Lys Glu Lys Thr Leu Ser Val Leu Asn Lys Thr Asp Ile Ser Ile Ile
                85                  90                  95

Val Ile Asp Ser Thr Val Gly Ile Thr Asp Tyr Asp Glu Ser Ile Ile
            100                 105                 110

Asn Gln Ile Lys Asn Lys Lys Ile Pro Leu Ile Gly Val Leu Asn Lys
        115                 120                 125

Ile Asp Ala Ala Asp Ile Lys Asp Leu Asp Val Glu His Met Lys Lys
    130                 135                 140

Glu Leu Lys Ile Pro Ile Val Lys Val Ser Ala Leu Lys Arg Lys Gly
145                 150                 155                 160

Ile Leu Glu Leu Lys Asn Gln Ile Ile Ala Ala Gln Pro Gln Ser Glu
                165                 170                 175

Asp Lys Phe Lys Val Ile Gly Asp Leu Ile Asn Pro Gly Asp Phe Val
            180                 185                 190
```

```
Val Leu Val Thr Pro Ile Asp Lys Ala Ala Pro Lys Gly Arg Leu Ile
            195                 200                 205

Leu Pro Gln Gln Gln Thr Ile Arg Asp Ile Leu Glu Ser Asp Ala Thr
    210                 215                 220

Ala Val Val Thr Lys Glu Phe Glu Leu Arg Glu Thr Leu Gln Asn Leu
225                 230                 235                 240

Gly Lys Lys Pro Lys Ile Val Val Thr Asp Ser Gln Ala Phe Leu Lys
                245                 250                 255

Val Ala Ala Asp Thr Pro Lys Asp Ile Leu Met Thr Ser Phe Ser Ile
            260                 265                 270

Leu Phe Ala Arg Cys Lys Gly Asp Leu Val Glu Leu Ile Lys Gly Val
    275                 280                 285

Lys Ala Val Lys Lys Leu Glu Asp Gly Asp Lys Val Leu Ile Ala Glu
290                 295                 300

Gly Cys Thr His His Arg Gln Ser Asp Asp Ile Gly Lys Val Lys Ile
305                 310                 315                 320

Pro Arg Trp Ile Arg Gln Ile Thr Gly Lys Lys Ile Asp Phe Glu Phe
                325                 330                 335

Ser Ser Gly Val Ser Phe Thr Glu Glu Ile Lys Lys Tyr Ala Leu Val
            340                 345                 350

Val His Cys Gly Ala Cys Met Leu Asn Arg Ala Ala Met Leu Tyr Arg
    355                 360                 365

Ile Asn Thr Ala Lys Glu Leu Asn Val Pro Ile Val Asn Tyr Gly Ile
370                 375                 380

Leu Ile Ala Tyr Val Gln Gly Ile Leu Asp Arg Ala Leu Lys Pro Phe
385                 390                 395                 400

Pro Leu Ala Lys Met Ala Trp Asp Asp Glu Asn
                405                 410
```

<210> SEQ ID NO 16
<211> LENGTH: 1236
<212> TYPE: DNA
<213> ORGANISM: Clostridium autoethanogenum
<220> FEATURE:
<221> NAME/KEY: misc_feature
<223> OTHER INFORMATION: CAETHG_2063, (FeFe)-hydrogenase H-cluster
    maturation GTPase HydF

<400> SEQUENCE: 16

```
atgagtttaa atgaaacacc tcgctcagta agaacacata tagcactctt tggcaaaagg    60
aatgcaggca atcaagtat  tataaacgcc ttaacaggac aagatatagc cattgtatca   120
gatgtaaggg gtactactac agatccagtc tataaatcta tggagatact tcccataggc   180
ccctgtgtaa taatagatac cgcaggtctt gatgatgagg gcgagctcgg cgaacttaga   240
aaagaaaaaa cattaagtgt tttaaataaa actgacatat caataattgt aatagattca   300
actgttggaa ttacagatta tgacgagtct ataataaatc aaataaaaaa taaaaaaatt   360
cccattatag gagtcttaaa caaaatcgat gctgctgata taaagatttt agatgtagaa   420
catatgaaaa aagaactcaa ataccaattg taaaagtat ctgcacttaa agaaaaggt     480 atacttgagt taaaaatca  aataatagct gcgcaacctc aaagtgaaga taaatttaaa   540
gtaattggtg atttaataaa ccctggagac tttgtggttc ttgtaactcc aatagataaa   600
gcagctccta aggaagact  tattctccct cagcagcaaa ccataagaga tatactggaa   660
agtgatgcta ctgcagtggt aactaaagaa ttcgaactta gagaaccctt acaaaaccta   720
gggaaaaaac ctaaaatagt agttacagat tctcaggcat ttttaaaagt agcagcagat   780
```

```
accccaaaag atatattgat gacttccttc tccatcctat ttgcaagatg caaaggagac    840
ctagtagaac ttataaaagg agtaaaagct gtaaaaaaat tagaagatgg agacaaagta    900
cttattgcag aaggctgcac tcaccataga caatctgatg atataggtaa agtaaaaatt    960
cctagatgga tacgacaaat taccggtaaa aaaatagatt tcgaatttte atctggcgtt    1020 tcttttacag aagaaataaa gaaatatgcc ttagtagttc actgcggtgc ttgcatgtta    1080
aatagagccg caatgcttta tagaataaat actgcaaaag agcttaatgt ccctattgta    1140
aactatggca tacttattgc atatgtccaa ggtatactag atagagcttt aaaaccattt    1200
ccactagcta aaatggcatg ggatgatgaa aattga                              1236
```

<210> SEQ ID NO 17
<211> LENGTH: 324
<212> TYPE: PRT
<213> ORGANISM: Clostridium autoethanogenum
<220> FEATURE:
<221> NAME/KEY: MISC_FEATURE
<223> OTHER INFORMATION: CAETHG_0339, Elongator protein 3/MiaB/NifB

<400> SEQUENCE: 17

```
Met Thr Ile Asp Lys Ile Leu Asn Asp Ala Lys Ser Glu Lys Leu Leu
1               5                   10                  15

Asn Lys Glu Glu Ala Ile Ala Leu Leu Asn Val Lys Asn Asn Ser Ser
            20                  25                  30

Asp Phe Tyr Lys Ile Ile Ser Leu Ala Asn Glu Met Thr Arg Ser Glu
        35                  40                  45

Phe Asn Asn Lys Ala Phe Phe Ala Gln Ile Gly Leu Asn Ala Glu
    50                  55                  60

Pro Cys Pro Val Asn Cys Lys Phe Cys Ser Met Gly Lys Asn His Tyr
65                  70                  75                  80

Thr Met Glu Ser Thr Trp Arg Lys Asp Ile Asn Ser Ile Leu Ser Glu
                85                  90                  95

Thr Lys Ala Ile Val Asn Glu Gly Ile Asn Asp Leu Phe Leu Met Thr
            100                 105                 110

Thr Ala Asp Tyr Pro Ile Asn Asp Phe Leu Asn Ile Ala Arg Asn Val
        115                 120                 125

Arg Ser Ile Leu Pro Asp Asn Ile Arg Leu Val Ala Asn Ile Gly Asp
    130                 135                 140

Phe Asp Tyr Val Thr Ala Leu Lys Leu Lys Glu Val Gly Phe Thr Gly
145                 150                 155                 160

Ala Tyr His Ile Lys Arg Leu Arg Glu Gly Ile Asp Thr Thr Ile Lys
                165                 170                 175

Pro Glu Thr Arg Ile Glu Thr Leu Asn Ser Ile Lys Lys Ala Gly Leu
            180                 185                 190

Glu Leu Tyr Tyr Cys Val Glu Pro Ile Gly Pro Glu His Ser Tyr Glu
        195                 200                 205

Glu Ile Val Asp Glu Met Leu Arg Ala Arg Asp Tyr Asn Val Gly Val
    210                 215                 220

Met Ala Ala Met Arg Arg Ile Pro Val Lys Gly Thr Pro Leu Tyr Glu
225                 230                 235                 240

Lys Gly Gln Ile Ser Ser Val Glu Leu Ser Lys Ile Ala Ala Val Thr
                245                 250                 255

Arg Ile Val Thr Arg Pro His Arg Ala Met Asn Ala His Glu Thr Ile
            260                 265                 270
```

-continued

```
Gln Met Ser Leu Ile Cys Gly Val Asn Gln Leu Tyr Ala Glu Ala Gly
        275                 280                 285

Ala Asn Pro Arg Asp Ser Ile Ser Asn Thr Glu Lys Ser Arg Gly Leu
    290                 295                 300

Ser Val Lys Asn Ile Lys Lys Leu Phe Glu Asp Ala Glu Tyr Glu Ile
305                 310                 315                 320

Ser Arg Asp Tyr

<210> SEQ ID NO 18
<211> LENGTH: 975
<212> TYPE: DNA
<213> ORGANISM: Clostridium autoethanogenum
<220> FEATURE:
<221> NAME/KEY: misc_feature
<223> OTHER INFORMATION: CAETHG_0339, Elongator protein

<400> SEQUENCE: 18
atgactatag ataaaatcct taatgatgct aaaagtgaaa aattacttaa taaagaagag      60
gcaatagcat tgttaaatgt aaaaaacaat tccagtgact tttataaaat tatatcactt    120
gcaaacgaaa tgacacgttc tgaatttaat aacaaggctt ttatatttgc ccaaatagga    180
ttaaacgcag aaccgtgtcc tgtaaactgt aaattttgtt ccatgggtaa aaaccattat    240
actatggaaa gtacatggag aaaggatata aactccatac tatctgaaac taaagctatt    300
gttaatgaag gtattaatga cttattccta atgacaactg ctgactatcc aataaatgat    360
ttcttgaata tagcaagaaa tgtaagaagc attttgccag ataatataag gctggtagct    420
aatattgggg actttgacta cgttacagca cttaaattaa agaggtggg ctttactgga    480 gcataccaca ttaaacgttt aagggaagga atagatacaa ctattaaacc tgaaactaga    540
attgaaactc tcaattcaat aaaaaaagca ggattggaat tatactattg tgtagaacct    600
attggcccag agcacagtta tgaggaaata gttgatgaaa tgttgagagc tagagattat    660
aatgtaggag ttatggctgc aatgagaaga ataccggtta aaggcactcc tttgtatgaa    720
aagggtcaaa tttcatcggt tgagctttct aaaattgcgg cagttacaag aatagttaca    780
cgacctcata gggctatgaa tgcacatgag accattcaga tgagtttaat ttgtggagta    840
aatcagttgt atgctgaagc aggtgctaat ccccgagata gtatatccaa tactgaaaaa    900
agccgtggat tatcggtaaa aaatataaaa aaatttttg aagatgcaga atatgaaata    960
tcaagagatt attag                                                     975

<210> SEQ ID NO 19
<211> LENGTH: 559
<212> TYPE: PRT
<213> ORGANISM: Clostridium autoethanogenum
<220> FEATURE:
<221> NAME/KEY: MISC_FEATURE
<223> OTHER INFORMATION: CAETHG_1576, hydrogenase, Fe-only
      (EC:1.12.7.2), WP_023162310

<400> SEQUENCE: 19

Met Ser Gly Gln Phe Met Ile Ile Asp Asn Ile Pro Val Glu Ile Asn
1               5                   10                  15

Gly Glu Lys Asn Ile Leu Glu Leu Ile Arg Lys Ala Gly Ile Asp Leu
            20                  25                  30

Pro Thr Phe Cys Tyr His Ser Glu Leu Ser Val Tyr Gly Ala Cys Arg
        35                  40                  45

Met Cys Met Val Glu Asp Lys Arg Gly Arg Met Gln Ala Ala Cys Ser
    50                  55                  60
```

```
Thr Pro Pro Gln Ala Gly Ile Glu Ile Tyr Thr Asn Thr Pro Arg Leu
 65                  70                  75                  80

Arg Lys Tyr Arg Lys Asn Ile Leu Glu Leu Leu Ala Asn His Cys
             85                  90                  95

Arg Asp Cys Thr Thr Cys Glu Lys Asn Glu His Cys Lys Leu Gln Asp
            100                 105                 110

Leu Ala Lys Arg Phe Lys Ile Lys Lys Val Arg Phe Lys Asn Thr Ser
            115                 120                 125

Ile Asn Lys Lys Ile Asp Asn Ser Ser Val Cys Ile Val Arg Asn Arg
            130                 135                 140

Ser Lys Cys Ile Leu Cys Gly Asp Cys Val Arg Val Cys Glu Glu Val
145                 150                 155                 160

Gln Asn Val Gly Ala Ile Asp Phe Val Lys Arg Gly Ser Asn Met Thr
                165                 170                 175

Val Thr Thr Ala Phe Asp Glu Pro Ile Ala Asn Ser Asn Cys Val Gly
                180                 185                 190

Cys Gly Gln Cys Ala Ala Val Cys Pro Thr Gly Ala Ile Val Val Lys
            195                 200                 205

Asp Asp Thr Ala Glu Leu Trp Glu Ala Leu Ser Asp Lys Asn Thr Lys
            210                 215                 220

Val Val Ala Gln Ile Ala Pro Ala Val Arg Val Gly Leu Asn Glu Glu
225                 230                 235                 240

Leu Gly Glu Glu Asn Gly Glu Asn Glu Met Gly Lys Ile Val Ala Ala
                245                 250                 255

Leu Arg Arg Met Gly Phe Asp Glu Val Phe Asp Thr Ser Thr Ala Ala
            260                 265                 270

Asp Leu Thr Val Leu Glu Glu Thr Ala Glu Phe Thr Ser Arg Leu Glu
            275                 280                 285

Lys Asn Glu Ser Leu Pro Leu Phe Thr Ser Cys Cys Ser Ala Trp Val
            290                 295                 300

Asn Tyr Val Glu Asn Thr His Pro Glu Leu Met Lys Tyr Val Ser Thr
305                 310                 315                 320

Cys Lys Ser Pro Met Glu Met Phe Ala Ser Val Leu Lys Glu Tyr Tyr
                325                 330                 335

Lys Asn Ser Asp Lys Lys Ile Val Val Ala Val Met Pro Cys Thr
            340                 345                 350

Ala Lys Lys Tyr Glu Ala Lys Arg Glu Glu Phe Ser Lys Asn Gly Val
            355                 360                 365

Pro Asp Val Asp Tyr Val Ile Thr Thr Gln Glu Leu Ile Ser Met Ile
            370                 375                 380

Arg Gln Ala Gly Ile Val Phe Pro Glu Leu Glu Pro Glu Ala Val Asp
385                 390                 395                 400

Met Pro Phe Asp Leu Ser Ser Gly Ala Gly Val Ile Phe Gly Val Thr
                405                 410                 415

Gly Gly Val Thr Glu Ala Val Ile Arg Lys Val Leu Ala Asp Lys Ser
                420                 425                 430

Asn Ala Ala Leu Arg Ala Ile Val Phe Asn Gly Val Arg Gly Met Glu
            435                 440                 445

Gly Thr Lys Glu Ala Ser Ile Thr Val Gly Asp Arg Glu Ile Lys Ile
            450                 455                 460

Ala Ile Val Ser Gly Leu Arg Asn Ala Glu Asn Leu Ile Gln Lys Ile
465                 470                 475                 480
```

```
Gln Ser Gly Glu Ser Lys Tyr Asp Phe Val Glu Val Met Ala Cys Pro
            485                 490                 495

Gly Gly Cys Ile Ser Gly Gly Gln Pro Phe Glu Lys Leu Glu Gly
        500                 505                 510

Lys Leu Lys Arg Ser Ala Gly Ile Tyr Gln Ser Asp Lys Met Ser Thr
            515                 520                 525

Ile Lys Arg Thr Ala Asp Asn Pro Leu Met Lys Ser Leu Tyr Ser Gly
            530                 535                 540

Leu Leu Lys Gly Lys Asn His Glu Leu Leu His Val Asn Arg Lys
545                 550                 555

<210> SEQ ID NO 20
<211> LENGTH: 1680
<212> TYPE: DNA
<213> ORGANISM: Clostridium autoethanogenum
<220> FEATURE:
<221> NAME/KEY: misc_feature
<223> OTHER INFORMATION: CAETHG_1576, hydrogenase, Fe-only (EC:1.12.7.2)

<400> SEQUENCE: 20
atgagtggac aatttatgat tatagataat attcctgtag agataaatgg tgaaaaaaat      60
attcttgaac taattagaaa agctggcatt gatttaccta cattttgcta tcattcggag     120
ctttcagttt atggtgcatg ccgtatgtgc atggttgaag ataaacgcgg ccgtatgcaa     180
gctgcatgtt ctactcctcc tcaagctggt atagaaatat atacaaatac tccaagactt     240
agaaaataca gaaaaaacat tcttgagttg ttactcgcaa atcattgcag agattgtaca     300
acttgtgaaa aaaatgagca ttgcaaacta caagatttag caaagcgttt taaaataaag     360
aaagtaagat ttaaaaatac ttctataaat aaaaaaattg ataattcatc agtatgcatt     420
gtaagaaata ggagtaaatg tatcttatgc ggtgactgtg taagagtgtg taagaagta      480
caaaatgttg gagctattga ttttgttaaa agaggttcta atatgactgt aactactgca     540
tttgatgaac ctatagcaaa ttcgaattgt gttggatgtg gtcaatgtgc ggcagtatgc     600
cctactggtg ctattgtagt aaaggatgat acagctgaat atgggaagc acttagtgat      660
aagaatacaa aggttgtagc tcaaattgcg cccgctgtaa gagttggtct taatgaggaa     720
ttaggtgagg aaaacggcga aacgaaatgg gtaaaatag tagctgcact tagaagaatg      780
ggatttgatg aagttttga tacttcaacg gcagcagatc ttacagtttt ggaagaaaca     840
gcagaattta cttcaagact tgaaaaaaat gaaagtttac cattgtttac atcctgttgt    900
tctgcatggg taaattatgt agagaataca catccagagt taatgaaata tgtttctact    960
tgcaaatcac ctatggaaat gtttgcttct gtacttaagg agtactataa aaatagtgat   1020
aaaaaaattg tagttgtagc agttatgcct tgtacagcta aaaaatatga agcaaaacga   1080
gaagaatttt caaaaaatgg tgtacctgat gtagattatg taataactac acaggagctt   1140
ataagtatga taagacaagc aggaattgta tttcctgaat tagagcctga agcagttgat   1200
atgccatttg atcttagcag tggagctgga gttatatttg gagtaacagg tggtgttaca   1260
gaggctgtta tacgtaaagt tttagctgat aaatcaaatg ctgcattacg tgcaattgtg   1320
tttaatggtg ttagggggcat ggaaggtact aaagaagcta gcattactgt tggtgatcgt   1380
gaaataaaaa tagcaatagt aagcggtctt agaaatgcag aaaatcttat acagaaaata   1440
caatctggtg aatcaaaata tgatttcgtt gaagttatgg catgtccagg tggatgcatt   1500
tctggtggtg gacaaccatt tgaaaaactt gaaggaaagc taaacgtag tgctggaata    1560
tatcaatcag ataaaatgag cactataaaa cgtacagctg acaatccgct tatgaaatca   1620
```
ctgtattcag gattgttaaa aggtaaaaac cacgaactat tacatgtaaa ccgcaaatag 1680

<210> SEQ ID NO 21
<211> LENGTH: 624
<212> TYPE: PRT
<213> ORGANISM: Clostridium autoethanogenum
<220> FEATURE:
<221> NAME/KEY: MISC_FEATURE
<223> OTHER INFORMATION: CAETHG_1577, NADH dehydrogenase (quinone) (EC:1.6.99.5)

<400> SEQUENCE: 21

Met Phe Ser Ser Arg Asn Asp Leu Ile Asn Ala Arg Lys Ile Tyr Lys
1               5                   10                  15

Asn Ser Leu Glu Met Gln Ser Lys Lys Ile Leu Ile Cys Gly Gly Thr
            20                  25                  30

Gly Cys Val Ala Gly Gly Ser Leu Lys Ile Tyr Asp Glu Phe Leu Arg
        35                  40                  45

Leu Met Lys Glu Lys Gly Ile Asn Cys Thr Val Glu Leu Glu Lys Glu
    50                  55                  60

Ser His Asp Lys Ser Val Gly Leu Lys Lys Ser Gly Cys His Gly Phe
65                  70                  75                  80

Cys Glu Met Gly Pro Leu Val Arg Val Glu Pro Phe Gly Tyr Leu Tyr
                85                  90                  95

Ile Gln Val Lys Pro Asp Asp Cys Leu Glu Ile Leu Asp Lys Thr Ile
            100                 105                 110

Leu Asn Asp Glu Cys Val Glu Arg Leu Ala Tyr Lys Lys Asp Gly Gln
        115                 120                 125

Ile Tyr Arg Lys Gln Gln Glu Ile Pro Phe Tyr Lys Lys Gln Thr Arg
    130                 135                 140

Val Ala Leu Glu His Cys Gly His Ile Asp Ala Thr Ser Ile Lys Glu
145                 150                 155                 160

Cys Ile Ala Leu Gly Gly Tyr Ser Ser Phe Glu Lys Ala Leu Phe Asp
                165                 170                 175

Met Asp Ser Asp Glu Val Ile Lys Gln Ile Asp Glu Ser Asn Leu Arg
            180                 185                 190

Gly Arg Gly Gly Gly Phe Pro Thr Gly Arg Lys Trp Thr Gln Val
        195                 200                 205

Lys Arg Gln Lys Thr Asp Met Lys Tyr Ile Val Cys Asn Gly Asp Glu
    210                 215                 220

Gly Asp Pro Gly Ala Phe Met Asp Arg Ser Val Met Glu Gly Asp Pro
225                 230                 235                 240

His Arg Val Leu Glu Gly Met Met Ile Ala Gly Val Ala Cys Gly Ala
                245                 250                 255

Gln Glu Gly Tyr Ile Tyr Val Arg Ala Glu Tyr Pro Leu Ala Val Glu
            260                 265                 270

Arg Leu Ser Asn Ala Ile Ala Gln Ala Lys Glu Tyr Gly Leu Leu Gly
        275                 280                 285

Lys Asn Ile Leu Gly Thr Gly Phe Asn Phe Asp Ile Lys Ile Asn Lys
    290                 295                 300

Gly Ala Gly Ala Phe Val Cys Gly Glu Gly Ser Ala Leu Thr Ala Ser
305                 310                 315                 320

Ile Glu Gly Lys Arg Gly Met Pro Arg Val Lys Pro Pro Arg Thr Val
                325                 330                 335

Glu His Gly Leu Phe Gly Lys Pro Thr Val Leu Asn Asn Val Glu Thr

```
              340                 345                 350
Phe Ala Asn Val Pro Val Ile Ile Ala Lys Gly Ala Asp Trp Tyr Arg
                355                 360                 365
Asn Ile Gly Pro Glu Asn Ser Pro Gly Thr Lys Ala Phe Ala Leu Thr
            370                 375                 380
Gly Asn Ile Glu Asn Thr Gly Leu Ile Glu Val Pro Met Gly Thr Thr
385                 390                 395                 400
Leu Arg Glu Val Ile Phe Asp Ile Gly Gly Ile Arg Asn Gly Lys
                405                 410                 415
Lys Phe Lys Ala Val Gln Ile Gly Gly Pro Ser Gly Gly Cys Leu Thr
            420                 425                 430
Ser Lys Asp Leu Asp Leu Pro Leu Asp Phe Asp Ser Leu Lys Lys Val
        435                 440                 445
Gly Ala Met Ile Gly Ser Gly Leu Val Val Met Asp Glu Asp Thr
    450                 455                 460
Cys Met Val Asp Thr Ala Lys Phe Phe Met Asn Phe Thr Arg Asn Glu
465                 470                 475                 480
Ser Cys Gly Lys Cys Val Pro Cys Arg Glu Gly Thr Lys Arg Met Leu
                485                 490                 495
Glu Ile Leu Glu Gly Ile Val Glu Gly Lys Gly Lys Ile Glu Asp Ile
            500                 505                 510
Asp Met Leu Leu Glu Leu Ala Asp Thr Ile Ser Ser Thr Ala Leu Cys
        515                 520                 525
Gly Leu Gly Lys Ser Ala Pro Ser Pro Val Val Ser Thr Ile Lys Asn
    530                 535                 540
Phe Arg Asp Glu Tyr Glu Thr His Ile Val Asp Lys Lys Cys Pro Ser
545                 550                 555                 560
Lys Thr Cys Thr Lys Leu Arg Thr Ile Tyr Ile Asp Lys Thr Ile Cys
                565                 570                 575
Lys Gly Cys Ser Lys Cys Ser Arg Ala Cys Pro Val Gly Ala Ile Ser
            580                 585                 590
Gly Thr Ile Lys Lys Pro Phe Thr Ile Asp Gln Asn Lys Cys Ile Lys
        595                 600                 605
Cys Gly Thr Cys Val Asp Thr Cys Ala Phe Lys Ala Val Lys Glu Asp
    610                 615                 620

<210> SEQ ID NO 22
<211> LENGTH: 1875
<212> TYPE: DNA
<213> ORGANISM: Clostridium autoethanogenum
<220> FEATURE:
<221> NAME/KEY: misc_feature
<223> OTHER INFORMATION: CAETHG_1577, NADH dehydrogenase (quinone)
      (EC:1.6.99.5)

<400> SEQUENCE: 22
atgtttagta gtagaaatga tttgattaat gctagaaaaa tttataaaaa tagccttgaa      60
atgcaaagta agaaaattct catatgtggt ggtactggat gtgttgcagg tggttcatta     120
aaaatttatg atgaattttt aagattgatg aaagaaaaag gaataaattg tacagtagaa     180
cttgaaaaag agtcgcatga taaatcagtt ggacttaaga aaagtggatg ccatggattt     240
tgtgagatgg gacctcttgt aagagttgaa cctttcggat acttgtatat acaagtaaaa     300
ccggatgact gtttagaaat tttagataaa actatactta atgatgaatg tgttgaacga     360
cttgcatata aaaagatgg acaaatatat aggaagcagc aggaaattcc tttttataaa     420
```

```
aaacaaacaa gagttgccct tgagcactgt ggtcacattg atgcaacttc aataaaagaa    480
tgtattgcct taggaggata ttcctcattt gaaaaagcat tatttgacat ggattcggat    540
gaagttatta agcaaataga tgaatcaaat ttaagaggac gtggaggcgg tggatttcct    600
actggccgta atggactcca gtaaaacgt caaaagacag atatgaaata tattgtatgt     660
aatggtgacg aaggggatcc aggtgcattc atggatagaa gcgtaatgga aggagatcct    720
catagagtac ttgaaggaat gatgattgca ggtgttgctt gtggtgcaca agagggatat    780
atttatgttc gtgcagaata tcctcttgct gtagagagac tttctaatgc aattgcacaa    840
gcaaaagaat acggactttt gggtaaaaat attcttggaa caggttttaa ctttgatatt    900
aaaattaata aggagcagg tgcttttgtc tgtggtgaag aagtgccct acagcttct      960 attgaaggaa aaagaggtat gccaagagta aaacctccaa gaactgttga acatggactc   1020
tttggtaagc caacagtact taataacgtt gaaacttttg caaatgtacc tgtaattatt   1080
gctaaaggag cagactggta tagaaacatt ggacctgaaa acagtcctgg tacaaaagcc   1140
tttgctttaa caggaaatat tgaaaataca ggattaattg aagtaccaat gggtacaacc   1200
ctaagagaag taatatttga tattggtgga ggaataagaa acggtaaaaa atttaaggct   1260
gtacaaatag gagggccatc tggcggatgt cttacaagta aagatcttga tttgccactg   1320
gattttgatt cacttaaaaa agtaggagcc atgataggtt ctggcggact tgtagttatg   1380
gatgaagata catgtatggt tgatactgca aaattttca tgaactttac acgaaatgaa    1440
tcctgtggaa aatgtgttcc ttgccgtgaa ggaactaaga gaatgcttga aatccttgag   1500
ggcatagttg aaggcaaagg taaaatgaa gacatagata tgttattaga gctagcagat    1560
actatatctt caacagcact atgcggactt gggaaatcgg ctccatcacc agttgttagt   1620
actattaaga atttccgtga tgaatatgaa actcacatag ttgataaaaa atgcccatca   1680
aaaacatgta ctaagcttag aacaatatat atagataaga caatttgtaa aggatgctca   1740
aaatgttcaa gagcttgtcc tgtcggagca atttcaggaa caatcaagaa gccatttaca   1800
attgatcaaa ataaatgtat aaaatgtgga acctgtgttg atacttgtgc atttaaagct   1860
gtaaaggagg attaa                                                    1875
```

<210> SEQ ID NO 23
<211> LENGTH: 158
<212> TYPE: PRT
<213> ORGANISM: Clostridium autoethanogenum
<220> FEATURE:
<221> NAME/KEY: MISC_FEATURE
<223> OTHER INFORMATION: CAETHG_1578, NADH dehydrogenase (ubiquinone) 24
      kDa subunit <400> SEQUENCE: 23

Met Asn Lys Ser Phe Asp Tyr Ser Lys Leu Asp Thr Ile Leu Lys Asn
1               5                   10                  15

His Glu Phe Lys Ser Ser Asn Ile Ile Ala Ile Leu Gln Asp Ile Gln
            20                  25                  30

Gly Ile Tyr Arg Tyr Leu Pro Lys Glu Ile Phe Pro Tyr Leu Ser Lys
        35                  40                  45

Asn Leu Gly Val Ser Lys Ala Lys Ile Tyr Gly Ile Ala Thr Phe Tyr
    50                  55                  60

Glu Asn Phe Ser Leu Glu Pro Lys Gly Lys Tyr Val Ile Lys Val Cys
65                  70                  75                  80

Asn Gly Thr Ala Cys His Val Arg Gly Ser Ile Pro Ile Leu Asn Ile
                85                  90                  95

Leu Arg Lys Glu Leu Lys Leu Ser Asp Thr Lys Thr Thr Asp Asp
            100                 105                 110

Leu Met Phe Ser Leu Glu Thr Val Ser Cys Leu Gly Ala Cys Gly Leu
        115                 120                 125

Ala Pro Ala Ile Thr Ile Asn Asp Lys Val His Gly Ser Met Thr Pro
130                 135                 140

Asp Lys Ala Met Glu Leu Leu Asn Ser Leu Lys Glu Glu Lys
145                 150                 155

<210> SEQ ID NO 24
<211> LENGTH: 477
<212> TYPE: DNA
<213> ORGANISM: Clostridium autoethanogenum
<220> FEATURE:
<221> NAME/KEY: misc_feature
<223> OTHER INFORMATION: CAETHG_1578, NADH dehydrogenase (ubiquinone) 24
      kDa subunit

<400> SEQUENCE: 24
atgaataagt catttgatta cagtaagtta gatactatat tgaaaaatca tgaatttaaa     60
tctagcaata ttattgcaat attgcaggac atccaaggaa atacaggta tttacctaag    120 gagatatttc cgtatctttc aaaaaatctt ggagttagca aagcgaagat atatggtata   180
gcaacctttt atgaaaattt ttctttagaa cctaaaggta aatacgtaat aaaagtatgt   240
aatggtactg cttgccatgt aagaggatct ataccatat tgaatatact aagaaaggaa   300
ttaaagcttt cagatactaa aactacaact gatgatttaa tgttttcttt ggaaacggtt   360
tcttgtcttg gcgcttgcgg actagcccct gctatcacaa ttaatgacaa ggtacatggt   420
tctatgactc ctgataaagc aatggaactt ttaaactcac ttaaggagga aaaatag      477

<210> SEQ ID NO 25
<211> LENGTH: 578
<212> TYPE: PRT
<213> ORGANISM: Clostridium autoethanogenum
<220> FEATURE:
<221> NAME/KEY: MISC_FEATURE
<223> OTHER INFORMATION: CAETHG_3569, hydrogenase, Fe-only
      (EC:1.12.7.2), WP_023163243

<400> SEQUENCE: 25

Met Val Asn Leu Thr Ile Asn Asp Ile Lys Val Ser Val Pro Glu Gly
1               5                   10                  15

Thr Thr Ile Leu Asn Ala Ala Lys Lys Val Asn Ile Asn Ile Pro Thr
            20                  25                  30

Leu Cys Tyr Leu Asp Leu His Asp Ile Lys Met Val Asn Arg Thr Ser
        35                  40                  45

Ser Cys Arg Val Cys Leu Val Glu Ile Glu Gly Arg Arg Asn Leu Ala
    50                  55                  60

Pro Ser Cys Ser Thr Glu Ala Phe Glu Gly Met Ile Val Arg Thr Asn
65                  70                  75                  80

Ser Ala Arg Ala Ile Lys Ala Arg Thr Met Val Glu Leu Leu Leu
                85                  90                  95

Ser Asp His Pro Thr Asp Cys Leu Val Cys Lys Asn Thr Gln Cys
            100                 105                 110

Gln Leu Gln Leu Ile Ala Ala Glu Leu Gly Ile Arg Lys Ile Arg Tyr
        115                 120                 125

Lys Gly Ala Met Ser Asn Tyr Lys Lys Asp Ser Ser Ser Gly Ala Leu
    130                 135                 140

```
Tyr Arg Asn Leu Asp Lys Cys Ile Met Cys Arg Arg Cys Glu Thr Met
145                 150                 155                 160

Cys Asn Glu Val Gln Thr Cys Gln Val Tyr Ser Ala Val Asp Arg Gly
            165                 170                 175

Phe Glu Thr Val Val Ser Pro Ala Phe Gly Arg Pro Met Val Asp Thr
            180                 185                 190

Gln Cys Thr Phe Cys Gly Gln Cys Val Ser Val Cys Pro Thr Ala Ala
            195                 200                 205

Leu Thr Gln Val Ser Asn Val Ala Lys Val Trp Glu Val Leu Thr Asp
210                 215                 220

Pro Asp Lys Tyr Val Val Gln Thr Ala Pro Ala Ile Arg Val Thr
225                 230                 235                 240

Leu Gly Glu Lys Phe Gly Met Glu Pro Gly Thr Ile Val Thr Gly Lys
            245                 250                 255

Met Val Ala Ala Leu Arg Arg Leu Gly Phe Asp Lys Val Cys Asp Thr
            260                 265                 270

Asp Phe Ala Ala Asp Val Thr Ile Leu Glu Glu Ala His Glu Phe Ile
            275                 280                 285

Asp Arg Leu Gln Asn Gly Gly Arg Leu Pro Ile Leu Thr Ser Cys Cys
            290                 295                 300

Pro Ser Trp Val Lys Phe Ile Glu His Gln Phe Pro Asp Leu Leu Asp
305                 310                 315                 320

Ile Pro Ser Thr Cys Lys Ser Pro His Ile Met Phe Gly Thr Leu Ala
                325                 330                 335

Lys Thr Tyr Met Ala Glu Lys Leu Asn Ile Asp Pro Ser Lys Ile Val
            340                 345                 350

Val Val Ser Val Met Pro Cys Ile Ala Lys Lys Tyr Glu Ile Ser Arg
            355                 360                 365

Lys Glu Leu Gln Tyr Glu Gly His Lys Asn Val Asp Leu Val Val Thr
            370                 375                 380

Thr Arg Glu Leu Ala Asp Met Ile Met Glu Ala Gly Ile Asp Phe Asn
385                 390                 395                 400

Lys Leu Pro Asp Glu Asp Phe Asp Asn Pro Leu Gly Glu Ser Thr Gly
                405                 410                 415

Ala Ser Val Ile Phe Gly Thr Thr Gly Gly Val Ile Glu Ala Ala Leu
            420                 425                 430

Arg Thr Ala Tyr Glu Trp Ile Thr Gly Glu Thr Leu Lys Glu Val Glu
            435                 440                 445

Phe His Ser Val Arg Gly Leu Asp Gly Leu Lys Glu Ala Ser Ile Asn
450                 455                 460

Ile Gly Gly Lys Lys Ile Asn Ile Gly Val Ala His Gly Leu Gly Asn
465                 470                 475                 480

Ala Arg Lys Leu Leu Glu Glu Ile Glu Ser Gly Glu Ser Lys Tyr His
                485                 490                 495

Ala Ile Glu Ile Met Ala Cys Pro Gly Gly Cys Ile Asp Gly Gly Gly
            500                 505                 510

Gln Pro Tyr His Phe Gly Asp Leu Asp Ile Val Lys Lys Arg Met Glu
            515                 520                 525

Ala Leu Tyr Arg Glu Asp Arg Asn Lys Pro Leu Arg Lys Ser His Glu
            530                 535                 540

Asn Pro Glu Val Gln Ala Leu Tyr Lys Glu Phe Ile Gly Asp Val Gly
545                 550                 555                 560
```

Gly Lys Lys Ala His Asp Leu Leu His Thr His Tyr Ile Lys Arg Gln
            565                 570                 575

Lys Leu

<210> SEQ ID NO 26
<211> LENGTH: 1737
<212> TYPE: DNA
<213> ORGANISM: Clostridium autoethanogenum
<220> FEATURE:
<221> NAME/KEY: misc_feature
<223> OTHER INFORMATION: CAETHG_3569, hydrogenase, Fe-only (EC:1.12.7.2)

<400> SEQUENCE: 26

```
atggtaaatt taactataaa cgatataaag gtttctgtcc cagaaggcac tacaatttta      60
aacgctgcaa aaaagtaaa cataaatata cctactctct gctatcttga tcttcacgat     120
ataaaaatgg taaatagaac ttcctcctgc agagtttgtc ttgttgaaat tgaaggaaga     180
cgaaatcttg caccttcatg ttctacagaa gctttcgagg gtatgatagt tagaacaaac     240
agtgccagag ctataaaagc aaggcgtacc atggtagaac ttttattatc agatcatcct     300
accgactgcc ttgtatgtga aaagaatact caatgccaac ttcaattaat tgctgctgaa     360
ttaggtataa ggaaaataag atataaaggt gctatgtcta attataagaa ggattcctcc     420
agcggtgctc tatatagaaa tctggataag tgcataatgt gcagacgatg cgaaaccatg     480
tgcaatgaag ttcaaacctg tcaggtttac tctgcagtag atagaggctt cgaaactgta     540
gtatcccctg catttggtcg tcctatggtt gacacgcaat gcacattttg cggtcaatgt     600
gtatcagtat gtccaaccgc tgcattaact caagttagta atgtagctaa ggtatgggaa     660
gtactaactg atcctgataa atatgtagta gttcaaactg ccctgctat aagagttact     720
ttaggtgaaa aattcggtat ggaacctgga actattgtaa ctggcaaaat ggttgcagcc     780
ttaagaagat tgggttttga taggtatgt gatacagact ttgcagcaga tgtaactatt     840
ttagaagaag ctcatgaatt tatagataga cttcaaaatg gtggaagact tccaatactc     900
acaagctgct gtcccagctg ggttaaattt atagaacatc aatttcctga tcttttagat     960
ataccttcaa cttgtaaatc tccacacata atgtttggta cttagctaa acatatatg    1020
gcagaaaaat taaatattga tccatctaaa attgtagtag tttcagttat gccctgtatt    1080
gcaaaaaat atgaaataag cagaaaagag cttcaatatg aaggtcataa aaatgttgat    1140
cttgtggtta ccacaagaga gcttgcagat atgataatgg aagcaggaat agattttaac    1200
aaacttcctg atgaagattt tgataatcca cttggagaat ccacaggtgc ctctgtaata    1260
tttggaacta ccggcggcgt aattgaagca gctcttagaa ctgcttatga atggattact    1320
ggagagactt taaagaagt agaatttcat agtgtaagag gtcttgacgg acttaaagaa    1380
gccagtataa atattggtgg taaaaaaata acatcggtg tagcacacgg tcttggcaac    1440
gcaagaaaac ttcttgagga aatagaatct ggtgaatcaa aatatcatgc tatagaaata    1500
atggcctgtc ctggaggatg tattgacgga ggaggtcagc catatcactt tggagattta    1560
gatatcgtaa agaaaagaat ggaagcttta tatagagaag atagaaacaa acctctcaga    1620
aaatctcatg aaaatcctga agttcaagct ctatataaag aattattgg tgatgtaggt    1680
ggaaaaaaag ctcatgatct ccttcacacc cattatataa aaggcaaaa attataa        1737
```

<210> SEQ ID NO 27
<211> LENGTH: 626
<212> TYPE: PRT
<213> ORGANISM: Clostridium autoethanogenum
<220> FEATURE:
<221> NAME/KEY: MISC_FEATURE
<223> OTHER INFORMATION: CAETHG_3570, NADH dehydrogenase (quinone)
      (EC:1.6.99.5)

<400> SEQUENCE: 27

```
Met Asp Lys Ile Lys Ser Phe Glu Asp Leu Lys Thr Leu Arg Glu Lys
 1               5                  10                  15

Tyr Lys Ala Lys Ile Ala Asn Arg Thr Tyr Asp Asn Ala Asp Lys Asn
             20                  25                  30

Ile Lys Lys Thr Leu Leu Val Cys Gly Gly Thr Gly Cys Arg Ala Ser
         35                  40                  45

Arg Ser Leu Asp Ile Val Asn Ile Leu Glu Thr Glu Ile Lys Asn Ala
     50                  55                  60

Gly Leu Glu Asn Thr Val Asp Val Ile Ser Thr Gly Cys Phe Gly Phe
 65                  70                  75                  80

Cys Glu Lys Gly Pro Ile Val Lys Val Val Pro Asp Asn Val Phe Tyr
                 85                  90                  95

Val Glu Val Asn Thr Glu Arg Ala Lys Leu Ile Val Tyr Glu His Met
            100                 105                 110

Ala Lys Asp Thr Val Val Glu Glu Ala Leu Tyr Lys Asp Pro Ile Thr
        115                 120                 125

Asn Glu Lys Ile Ser Asn Gln Thr Asp Ile Pro Phe Tyr Lys Asn Gln
130                 135                 140

Lys Arg Ile Ala Leu Arg Asn Cys Gly Leu Leu Asn Pro Glu Asp Ile
145                 150                 155                 160

Thr Glu Tyr Ile Ala Leu Asn Gly Tyr Glu Ala Leu Gly Lys Val Leu
                165                 170                 175

Thr Gln Met Thr Pro Asp Ser Val Ile Asp Glu Ile Lys Lys Ser Gly
            180                 185                 190

Leu Arg Gly Arg Gly Gly Gly Phe Pro Thr Gly Val Lys Trp Glu
        195                 200                 205

Met Thr Lys Lys Ser Glu Ser Asp Thr Lys Phe Met Ile Cys Asn Ala
210                 215                 220

Asp Glu Gly Asp Pro Gly Ala Phe Met Asp Arg Ser Ile Leu Glu Gly
225                 230                 235                 240

Asp Pro Asn Ser Val Leu Glu Ala Met Ala Ile Ala Gly Tyr Cys Ile
                245                 250                 255

Gly Ala Asn Lys Gly Tyr Ile Tyr Ile Arg Ala Glu Tyr Pro Leu Ala
            260                 265                 270

Ile Asn Arg Leu Lys Ile Ala Leu Lys Gln Ala Tyr Asp Leu Gly Leu
        275                 280                 285

Leu Gly Asp Asn Ile Leu Gly Thr Asp Phe Ser Phe His Ile Asp Leu
290                 295                 300

Lys Tyr Gly Ala Gly Ala Phe Ile Cys Gly Glu Glu Thr Ala Leu Ile
305                 310                 315                 320

Asn Ser Ile Glu Gly Gly Arg Gly Glu Pro Thr Val Lys Pro Pro Phe
                325                 330                 335

Pro Ser Gln Ile Gly Leu Trp Lys Lys Pro Thr Asn Ile Asn Asn Val
            340                 345                 350

Glu Thr Leu Ala Asn Ile Pro Pro Ile Ile Leu Lys Gly Ser Lys Trp
        355                 360                 365

Phe Ser Ser Ile Gly Thr Glu Lys Ser Lys Gly Thr Lys Val Phe Ala
370                 375                 380
```

-continued

```
Leu Ala Gly Lys Ile Asn Asn Val Gly Leu Val Glu Val Pro Met Gly
385                 390                 395                 400

Ile Thr Leu Arg Glu Ile Ile Tyr Asn Leu Gly Gly Gly Ile Arg Gly
            405                 410                 415

Gly Lys Lys Leu Lys Ala Val Gln Thr Gly Gly Pro Ser Gly Gly Cys
        420                 425                 430

Ile Pro Ala Asp His Leu Asp Thr Ala Ile Asp Tyr Glu Ser Leu Thr
    435                 440                 445

Glu Ile Gly Ser Met Met Gly Ser Gly Gly Met Ile Val Met Asp Glu
450                 455                 460

Asp Asn Cys Met Val Asn Ile Ala Lys Phe Tyr Leu Gln Phe Ser Val
465                 470                 475                 480

Asp Glu Ser Cys Gly Lys Cys Thr Ala Cys Arg Ile Gly Asn Lys Arg
            485                 490                 495

Leu Leu Glu Ile Leu Glu Asp Ile Thr Lys Gly Lys Gly Thr Met Glu
        500                 505                 510

His Leu Glu Gly Leu Lys Asp Leu Ser Tyr Val Ile Lys Asp Ser Ala
    515                 520                 525

Leu Cys Gly Leu Gly Gln Thr Ser Pro Asn Pro Ile Ile Ser Thr Met
530                 535                 540

Lys Phe Phe Trp Asp Glu Tyr Val Ala His Val Lys Asp Lys Arg Cys
545                 550                 555                 560

Pro Ala Gly Val Cys Thr Ala Leu Leu Lys Tyr Asn Ile Asn Ser Glu
            565                 570                 575

Lys Cys Ile Gly Cys Thr Ala Cys Thr Lys Val Cys Pro Lys Gly Ala
        580                 585                 590

Ile Ser Gly Glu Ile Lys Lys Ser His Val Ile Asp Lys Ser Lys Cys
    595                 600                 605

Ile Asn Cys Gly Ala Cys Ser Ser Ile Cys Lys Phe Ser Ala Ile Thr
610                 615                 620

Lys Glu
625

<210> SEQ ID NO 28
<211> LENGTH: 1881
<212> TYPE: DNA
<213> ORGANISM: Clostridium autoethanogenum
<220> FEATURE:
<221> NAME/KEY: misc_feature
<223> OTHER INFORMATION: CAETHG_3570, NADH dehydrogenase (quinone)
      (EC:1.6.99.5)

<400> SEQUENCE: 28
atggataaga taaatccttt tgaagattta aaaactttaa gagaaaagta taaagctaag      60
atagcaaacc gtacttatga taatgcagat aaaaatataa aaaaaacttt acttgtatgc     120
ggtggaacag gatgtcgtgc ttcaagaagc ttagatatag tcaacatact tgaaactgaa     180
attaaaaacg caggtctaga aaatacagtt gatgtcattt ctacaggatg ttttgggttt     240
tgtgagaaag gacctatcgt taaagttgta ccagataatg ttttttatgt tgaagttaat     300
accgaaagag caaagctaat tgtgtatgaa catatggcca agatacagt agttgaggaa      360 gctttatata agacccctat tactaatgag aaaatatcca accaaacgga tattccattc     420
tataaaaatc aaaaaagaat tgctcttaga aattgcggtc ttttaaaccc tgaagatatt     480
acagaataca tagcactgaa tggctacgaa gctttaggca agttttaac acaaatgaca      540 cctgacagcg taattgatga aattaaaaaa agtggcttaa gaggcagagg tggcggtggc     600
```

```
tttcctactg gcgtaaaatg ggaaatgaca aaaaaatctg aatctgatac aaagtttatg      660
atctgcaatg ctgatgaggg tgatcccggt gcctttatgg atagaagcat acttgaggga      720
gatccaaatt ctgtacttga agctatggct attgcaggtt actgcatagg tgcaaataag      780
ggttatattt atatcagagc tgaatatcct cttgcaataa acagattaaa aattgcttta      840
aagcaagctt acgatttagg tttattgggt gataatattt taggtactga ttttcctttt      900
cacatagatt taaatatgg tgccggagct ttcatctgtg gtgaggaaac tgcactcata      960
aattccatag aaggcggacg tggagagcct accgtaaaac ctccttttcc ttcccaaata     1020
ggtctctgga aaaaccaac taatataaat aatgtagaaa ctctggcaaa catcccccct     1080
attatattaa aaggctctaa gtggtttagt tctataggaa ctgaaaagag taaaggaacc     1140
aaagtttttg ccttagcagg caagatcaat aatgttggcc ttgttgaggt acctatgggt     1200
ataaccttgc gggaaataat atataattta ggcggaggta ttcgcggtgg taaaaaactt     1260
aaggctgttc aaactggcgg tccttctggc gggtgcattc ctgcagatca tttagatact     1320
gccattgatt acgaaagtct tactgaaata ggctccatga tgggttctgg tggaatgata     1380
gttatggatg aagataattg tatggtgaat atagccaaat tctatctcca atttagtgta     1440
gatgaatcct gtggaaagtg cactgcctgc agaatcggaa ataaaagact tttagaaatt     1500
ttagaggata tcactaaagg aaaaggtacc atggaacatc ttgaaggatt aaaagattta     1560
tcctatgtaa taaaggattc agccctatgt ggtcttggtc aaacatcacc taatccaatt     1620
ataagtacaa tgaaattttt ctgggatgaa tatgtagccc acgtaaaaga taaacgctgt     1680
cctgctggag tttgcactgc acttttaaaa tacaatataa attctgaaaa atgtattggc     1740
tgcacagcct gtacaaaggt atgccctaaa ggagctattt ccggagaaat aaaaaagtca     1800
catgtaatag ataagtcaaa atgtataaat tgtggtgcat gtagtagtat ttgtaagttt     1860
tctgctatta cgaaagaata a                                                1881
```

<210> SEQ ID NO 29
<211> LENGTH: 160
<212> TYPE: PRT
<213> ORGANISM: Clostridium autoethanogenum
<220> FEATURE:
<221> NAME/KEY: MISC_FEATURE
<223> OTHER INFORMATION: CAETHG_3571, NADH dehydrogenase (ubiquinone) 24
      kDa subunit

<400> SEQUENCE: 29

Met Asp Val Cys Lys Leu Asp Asn Glu Lys Leu Lys Glu Leu Ser Ser
1               5                   10                  15

Tyr Ile Asp Ser Leu Glu Glu Lys Glu Gly Ser Leu Ile Ser Val Leu
                20                  25                  30

His Arg Ala Gln Asp Ile Phe Gly Tyr Leu Pro Glu Glu Leu Gln Thr
            35                  40                  45

Phe Ile Ala Asn Lys Leu Asp Ile Ser Ala Ala Lys Val Phe Gly Val
        50                  55                  60

Val Thr Phe Tyr Ser Tyr Phe Thr Met Lys Pro Lys Gly Lys His Val
65                  70                  75                  80

Ile Ser Ile Cys Met Gly Thr Ala Cys Phe Val Lys Gly Ala Glu Asn
                85                  90                  95

Ile Leu Glu Glu Phe Arg Asn Gln Leu Lys Val Lys Asp Gly Phe Thr
            100                 105                 110

Thr Glu Asp Gly Leu Phe Thr Ile Asp Ile Leu Arg Cys Val Gly Ala

```
                    115                 120                 125
Cys Gly Leu Ala Pro Val Val Val Asp Gly Thr Val His Gly Lys
            130                 135                 140

Val Lys Val Glu Asp Val Lys Gly Ile Leu Ser Gln Tyr Thr Leu Lys
145                 150                 155                 160

<210> SEQ ID NO 30
<211> LENGTH: 483
<212> TYPE: DNA
<213> ORGANISM: Clostridium autoethanogenum
<220> FEATURE:
<221> NAME/KEY: misc_feature
<223> OTHER INFORMATION: CAETHG_3571, NADH dehydrogenase (ubiquinone) 24
      kDa subunit

<400> SEQUENCE: 30
atggatgtat gcaaattaga taacgaaaaa ctaaagaaac tatcttccta tatagatagt      60
ttggaagaaa agaaggttc acttataagt gtacttcaca gagctcagga tatatttgga     120
taccttcctg aagaattaca aacatttatt gcaaataaac ttgacattag tgcagcaaaa     180
gtatttggcg tagttacttt ctattcatac tttacaatga agcccaaagg taaacatgta     240
ataagcatat gcatgggtac agcttgtttt gttaagggtg cagaaaacat tttagaagaa     300
tttagaaatc agcttaaagt aaaagatgga tttaccacag aagacggatt gttcactata     360 gatatttaa gatgtgttgg agcttgcggc cttgcaccag tagttgtagt tgatggaaca     420
gtccatggga agtaaaggt cgaagatgtt aaaggaatat aagtcaata taccttaaaa     480 taa                                                                 483

<210> SEQ ID NO 31
<211> LENGTH: 448
<212> TYPE: PRT
<213> ORGANISM: Clostridium autoethanogenum
<220> FEATURE:
<221> NAME/KEY: MISC_FEATURE
<223> OTHER INFORMATION: CAETHG_0110, hydrogenase large subunit domain
      protein, WP_013238683.1

<400> SEQUENCE: 31

Met Arg Asp Asp Tyr Arg Asn Leu Phe Lys Phe Ile Ile Lys Ala Tyr
1               5                   10                  15

Tyr Ser Gly Asn Phe Glu Glu Val Met Ser Phe Leu Leu Glu Ser
            20                  25                  30

Lys Met Asp Lys Gln Glu Leu Cys Lys Ile Ile Ser Thr Leu Cys Gly
        35                  40                  45

Thr Asn Ile Asp Tyr Ser Ser Asn Phe Ile Glu Asn Leu Lys Lys Ala
    50                  55                  60

Ile Lys Ser Tyr Lys Gln Gly Lys Val Val Asn Lys Val Arg Asp
65                  70                  75                  80

Cys Ser Met Glu Cys Val Asp Glu Lys Gly Glu Ile Leu Cys Gln Lys
                85                  90                  95

Thr Cys Pro Phe Asp Ala Ile Phe Ile Asp Asn Lys Lys Asn Cys Ala
            100                 105                 110

Tyr Ile Asp Lys Glu Lys Cys Thr Asp Cys Gly Phe Cys Val Asp Val
        115                 120                 125

Cys Pro Thr Gly Gly Ile Met Asp Lys Val Gln Phe Ile Pro Leu Ala
    130                 135                 140

Asp Ile Leu Lys Ser Lys Ser Pro Val Val Ala Ile Val Ala Pro Ala
145                 150                 155                 160
```

```
Ile Ile Gly Gln Phe Gly Glu Asp Val Thr Met Asp Gln Leu Arg Thr
                165                 170                 175
Ala Phe Lys Lys Leu Gly Phe Thr Asp Met Ile Glu Val Ala Phe Phe
            180                 185                 190
Ala Asp Met Leu Thr Leu Lys Glu Ser Ile Glu Phe Asp Asn His Val
        195                 200                 205
Lys Asp Glu Lys Asp Phe Met Ile Thr Ser Cys Cys Cys Pro Met Trp
    210                 215                 220
Val Ala Met Val Lys Lys Val Tyr Ser Asn Leu Val Lys His Val Ser
225                 230                 235                 240
Pro Ser Val Ser Pro Met Val Ala Gly Arg Val Leu Lys Lys Leu
                245                 250                 255
Asn Pro Tyr Cys Lys Val Val Phe Ile Gly Pro Cys Ile Ala Lys Lys
            260                 265                 270
Ser Glu Ala Lys Glu Glu Asp Ile Lys Gly Ala Ile Asp Phe Val Leu
        275                 280                 285
Thr Phe Glu Glu Leu Arg Asp Ile Phe Asp Ala Phe His Ile Val Pro
    290                 295                 300
Ser Lys Leu Glu Gly Asp Phe Ser Ser Lys Tyr Ala Ser Arg Gly Gly
305                 310                 315                 320
Arg Leu Tyr Ala Arg Thr Gly Val Ser Ile Ala Val Ser Glu Ala
                325                 330                 335
Val Glu Arg Ile Phe Pro Glu Lys His Lys Leu Phe Ser Ala Ile Gln
            340                 345                 350
Ala Asn Gly Ile Arg Glu Cys Arg Glu Met Leu Thr Lys Val Gln Asn
        355                 360                 365
Gly Glu Ile Lys Ala Asn Phe Ile Glu Gly Met Gly Cys Ile Gly Gly
    370                 375                 380
Cys Val Gly Gly Pro Lys Ala Ile Val Leu Lys Asp Glu Gly Arg Asp
385                 390                 395                 400
Arg Val Asn Lys Phe Ala Gln Asp Ser Glu Ile Lys Val Ala Val Asp
                405                 410                 415
Ser Glu Cys Met His Gly Val Leu His Ala Leu Asp Ile His Ser Ile
            420                 425                 430
Asp Asp Phe Lys Asp Glu Lys Lys Ile Glu Leu Leu Glu Arg Glu Phe
        435                 440                 445

<210> SEQ ID NO 32
<211> LENGTH: 1347
<212> TYPE: DNA
<213> ORGANISM: Clostridium autoethanogenum
<220> FEATURE:
<221> NAME/KEY: misc_feature
<223> OTHER INFORMATION: CAETHG_0110, hydrogenase large subunit domain
      protein

<400> SEQUENCE: 32
ttgagagatg attataggaa tctatttaaa ttcataataa aggcatatta tagtggaaat      60
tttgaagaag aagtgatgtc attttttatta gagtctaaaa tggataaaca ggaattgtgt    120
aagattatat ctacgttgtg cggcactaat atagattata gttccaattt tatagaaaat    180
ttgaaaaaag caataaagtc ttataaacaa gaaggtaaag tagtcaataa agttagagac    240
tgttccatgg aatgtgtgga tgaaaaaggt gagatacttt gtcaaaaaac atgtcctttt    300
gatgcaattt ttatagacaa taagaaaaat tgtgcttaca tagataaaga aaatgtacc    360
```

```
gattgtggtt tttgtgtaga tgtttgtcct actgggggaa taatggataa agttcagttc    420
attcctcttg ctgatatttt aaaaagcaaa tctccagttg tggctatagt ggctcctgcc    480
ataataggac agtttggcga agatgttact atggatcaac ttaggactgc ttttaaaaaa    540
ctgggattta ctgatatgat tgaagtggca ttttttgcag atatgcttac tttaaaggag    600
tctattgaat ttgacaatca tgtaaaagat gaaaaagatt ttatgataac ctcctgctgc    660
tgccctatgt gggtagctat ggtaaaaaag gtatacagta atttggttaa acacgtatcc    720
ccctctgtat ctccaatggt tgcaggagga agagtactta aaaagttaaa cccttactgc    780
aaggtagtgt ttataggacc atgtattgct aaaaaatctg aggcaaagga agaagacata    840
aaaggagcaa tagatttcgt acttactttt gaagaattaa gagatatatt tgatgctttt    900
catatagttc catctaaact tgaaggagat ttttcctcta aatatgcgtc taggggtgga    960
agattatatg ctcgtacagg gggagtttct attgcagtaa gcgaagctgt ggaaagaatt   1020
ttccctgaaa agcataaact attttagtgca attcaggcaa atggcattag agaatgtaga   1080
gaaatgctta ccaaggtgca aaatggagaa ataaaagcta tttttattga aggaatgggc   1140
tgcattggcg gatgtgtagg tggtcccaaa gcaattgtac ttaaggatga aggtagggat   1200
cgagtaaata aatttgcaca agattctgaa ataaagttg ctgtagatag tgaatgcatg    1260
catggagtat tacatgcttt ggatatacat tctatagatg attttaagga tgagaaaaaa   1320
atagaactgt tagaacgaga atttttaa                                      1347
```

<210> SEQ ID NO 33
<211> LENGTH: 457
<212> TYPE: PRT
<213> ORGANISM: Clostridium autoethanogenum
<220> FEATURE:
<221> NAME/KEY: MISC_FEATURE
<223> OTHER INFORMATION: CAETHG_3841, hydrogenase, Fe-only
      (EC:1.12.7.2), WP_035787664

<400> SEQUENCE: 33

```
Met Thr Val Lys Ser Glu Gly Ile Val Lys Ile Asp Lys Glu Leu Cys
1               5                   10                  15

Thr Gly Cys Arg Arg Cys Ala Asp Ile Cys Pro Val Asp Ala Ile Glu
            20                  25                  30

Gly Glu Lys Gly Gln Pro Gln Thr Ile Asn Thr Glu Arg Cys Val Leu
        35                  40                  45

Cys Gly Gln Cys Val Gln Ile Cys Ser Ala Tyr Ala Ser Ala Phe Asp
    50                  55                  60

Glu Asp Ile Thr Pro His Lys Glu Lys Ile Lys Glu Arg Asn Met Leu
65                  70                  75                  80

Pro Ser Val Lys Glu Pro Leu Phe Ala Ser Tyr Tyr Arg Gly Asp Ala
                85                  90                  95

Pro Ala Val Lys Glu Ala Leu Ala Asn Ser Lys Leu Phe Thr Met Val
            100                 105                 110

Gln Cys Ala Pro Ala Val Arg Val Ala Ile Ala Glu Glu Phe Gly Met
        115                 120                 125

Pro Leu Gly Ser Leu Thr Pro Gly Lys Met Ala Ala Leu Arg Glu
    130                 135                 140

Leu Gly Phe Asp Arg Ile Tyr Asp Thr Asn Phe Ala Ala Asp Leu Thr
145                 150                 155                 160

Ile Met Glu Glu Gly Ser Glu Leu Ile Lys Arg Val Thr Glu Gly Gly
                165                 170                 175
```

```
Val Leu Pro Met Phe Thr Ser Cys Cys Pro Ala Trp Val Lys Phe Ile
            180                 185                 190

Glu Gln Asp Tyr Pro Glu Leu Ile Pro His Leu Ser Ser Cys Lys Ser
        195                 200                 205

Pro Gln Gln Met Glu Gly Ala Leu Leu Lys Thr Tyr Gly Ala Gln Val
        210                 215                 220

Asp Gly Val Asp Ala Gly Lys Ile Tyr Ser Val Ser Val Met Pro Cys
225                 230                 235                 240

Ile Cys Lys Lys Phe Glu Cys Glu Arg Pro Glu Met Lys Asp Ser Gly
                245                 250                 255

Tyr Gln Asp Val Asp Ala Val Ile Thr Thr Arg Glu Leu Ala Gln Leu
            260                 265                 270

Ile Lys Asp Asp Gly Ile Asp Phe Asn Gly Leu Pro Glu Lys Glu Phe
        275                 280                 285

Asp Lys Pro Leu Gly Thr Tyr Ser Gly Ala Gly Thr Ile Phe Cys Ala
        290                 295                 300

Thr Gly Gly Val Met Glu Ala Ala Leu Arg Thr Ala Tyr Lys Leu Ile
305                 310                 315                 320

Thr Lys Glu Glu Ile Pro Asp Val Asp Leu Lys Phe Ile Arg Gly Gly
                325                 330                 335

Glu Gly Ala Arg Ser Ser Glu Ile Lys Val Gly Asp Leu Thr Leu Lys
            340                 345                 350

Val Ala Val Ala Gly Leu Lys Asn Val Val Pro Val Leu Glu Ala
        355                 360                 365

Ile Lys Thr Gly Lys Ala Asp Phe His Phe Ile Glu Val Met Thr Cys
    370                 375                 380

Pro Val Gly Cys Val Ser Gly Gly Gln Pro Lys Val Leu Ile Pro
385                 390                 395                 400

Asp Glu Lys Ala Asp Ser Tyr Thr Asn Arg Thr Cys Ser Thr Tyr Val
                405                 410                 415

His Asp Glu Asn Met Glu Tyr Arg Lys Ser His Asp Asn Pro Glu Ile
            420                 425                 430

Gln Lys Ile Tyr Lys Glu Phe Leu Val Glu Asp Asn Ile His His Leu
        435                 440                 445

Leu His Thr Thr Tyr Thr Pro Arg Arg
    450                 455
```

<210> SEQ ID NO 34
<211> LENGTH: 1374
<212> TYPE: DNA
<213> ORGANISM: Clostridium autoethanogenum
<220> FEATURE:
<221> NAME/KEY: misc_feature
<223> OTHER INFORMATION: CAETHG_3841, hydrogenase, Fe-only (EC:1.12.7.2)

<400> SEQUENCE: 34

```
ttgacagtta aaagtgaagg tattgtcaaa attgataaag agttgtgtac aggatgtaga      60
cgatgtgcag atatttgtcc tgtagatgct atagaaggtg agaagggaca acctcaaaca     120
attaatactg aacgctgtgt tttgtgtggt cagtgtgtac aaatttgcag tgcttatgca     180
tctgcatttg atgaagatat tactcctcat aaggaaaaga taaagagcg taatatgctt      240 ccatctgtta agagcccttt atttgcatcc tactatagag gagatgctcc agcagtaaaa     300
gaggccttag caaattctaa acttttttact atggttcaat gcgcaccagc agtacgtgtg     360
gctattgccg aagaatttgg tatgccactt ggaagtttaa caccagggaa aatggcagct     420
```

```
gcgctaagag agttaggttt tgatcgaatt tatgatacta attttgctgc tgatctaact      480
attatggagg aaggcagtga acttattaaa agggttactg aaggtggagt actgccaatg      540
ttcacttcat gttgtcctgc ttgggtaaaa tttattgagc aggattatcc ggaacttatt      600
ccacatctgt cttcttgtaa atctccgcag caaatggaag gtgctctgct aaaacatat       660 ggtgcacagg ttgatggtgt agatgctggc aagatttata gtgtttcagt tatgccttgt      720
atttgcaaaa aatttgaatg tgaacgtcct gaaatgaaag acagtggata tcaggatgta      780
gatgctgtaa ttaccacacg ggaacttgca caattaatca aggatgatgg cattgatttt      840
aatggtttac ctgaaaaaga atttgacaag ccacttggaa cttattctgg tgcaggcact      900
attttctgtg ctactggtgg tgttatggaa gctgccctgc gtacggcata taaattgatt      960
actaaagaag agattccaga tgtcgatctc aaattcataa gaggaggcga aggcgcaaga     1020
agttcagaaa ttaaagtagg agatttaaca ctaaaagtag cagtagttgc tggtctgaaa     1080
aatgttgtac cagttttgga agcaattaaa actgggaaag cagatttcca tttcattgaa     1140
gtgatgacct gtccagttgg atgtgttagc gggggcggac aacctaaggt attgataacct     1200 gatgaaaaag ctgattcgta tactaatcgt acatgcagta cgtatgtaca tgatgaaaat     1260
atggaatata gaaaatcaca tgataatcct gaaatacaga aaatttataa agaattcttg     1320
gtagaagata atattcatca tttgcttcat actacgtata cgccaaggag gtaa          1374
```

<210> SEQ ID NO 35
<211> LENGTH: 446
<212> TYPE: PRT
<213> ORGANISM: Clostridium autoethanogenum
<220> FEATURE:
<221> NAME/KEY: MISC_FEATURE
<223> OTHER INFORMATION: CAETHG_0119, hydrogenase large subunit domain
      protein

<400> SEQUENCE: 35

```
Met Asn Lys Ser Pro Val Thr Val Leu Lys Glu Lys Cys Thr Gly Cys
1               5                   10                  15

Asn Lys Cys Ile Arg Thr Cys Pro Ile Leu Gly Ala Asn Val Thr Ala
            20                  25                  30

Thr Glu Asn Gly Val Ser Lys Val Tyr Ile Asp Glu Arg Cys Ile
        35                  40                  45

Gly Cys Gly Glu Cys Val Lys Val Cys Glu His Gly Ala Arg Asp Phe
    50                  55                  60

Asn Asp Ser Thr Gln Asp Phe Phe Lys Asp Leu Lys Lys Gly Lys Lys
65                  70                  75                  80

Ile Thr Val Ile Ala Ala Pro Ser Ile Ile Val Asn Ile Lys Asn Tyr
                85                  90                  95

Lys Lys Phe Phe Gly Tyr Leu Lys Ser Leu Gly Val Ser Ile Ile Tyr
            100                 105                 110

Asp Val Ser Phe Gly Ala Asp Ile Thr Thr Trp Ala Tyr Leu Lys Ala
        115                 120                 125

Met Lys Glu Lys Asn Ile Ser Ser Leu Ile Ser Gln Pro Cys Pro Ile
    130                 135                 140

Val Val Asn Tyr Ile Glu Lys Tyr Lys Pro Glu Leu Ile Glu Tyr Leu
145                 150                 155                 160

Ala Pro Ile His Ser Pro Met Met Cys Thr Ala Val Tyr Leu Lys Lys
                165                 170                 175

Tyr Lys His Ile Cys Glu Asp Ile Ala Phe Leu Ser Pro Cys Ile Gly
            180                 185                 190
```

-continued

```
Lys Leu Ile Glu Ile Asn Asp Lys Asn Thr Asp Gly Tyr Val Lys Tyr
        195                 200                 205

Asn Val Thr Tyr Lys Lys Ile Leu Asp Tyr Leu Arg Asp Asn Asn Val
    210                 215                 220

Asn Leu Asn Asn Tyr Asp Glu Val Glu Phe Asp Asn Val Pro Ala Ser
225                 230                 235                 240

Leu Gly Val Val Tyr Ser Leu Pro Gly Gly Leu Lys Ala Asn Val Lys
                245                 250                 255

Ala Arg Thr Glu Glu Leu His Val Leu Gln Ile Glu Gly His Lys Glu
            260                 265                 270

Ala Ile Glu Tyr Leu Asn Lys Tyr Ser Asp Arg Val Lys Ala Asn Lys
        275                 280                 285

Leu Ile Pro Ser Leu Leu Asp Ile Leu Asn Cys Lys Asn Gly Cys Asn
    290                 295                 300

Ile Gly Thr Ala Ser Leu Asp Asn Leu Thr Glu Tyr Asp Ile Gln Tyr
305                 310                 315                 320

Arg Phe His Asp Ile Lys Val Glu Lys Leu Arg Glu Lys Thr Gly Leu
                325                 330                 335

Phe Lys Lys Lys Ile Lys Ser Ile Asp Glu Tyr Phe Asp Lys Asn Leu
            340                 345                 350

Asn Leu Asn Asp Phe Val Arg Lys Tyr Thr Ala Gln Lys Val Lys Lys
        355                 360                 365

Ile Ile Glu Pro Thr Gln Lys Asp Tyr Asp Asn Ile Phe Asp Glu Met
    370                 375                 380

Met Lys Thr Thr Thr Leu Gly Lys Glu Phe Asn Cys Ser Ala Cys Gly
385                 390                 395                 400

Tyr Ser Thr Cys Lys Glu Met Val Lys Met Ile Phe Asn Gly Ile Asn
                405                 410                 415

Ser Lys Glu Asn Cys Ile Tyr Tyr Val Lys Lys Lys Ser Ile Trp Asn
            420                 425                 430

Ile Ala Asn Trp Lys Lys Lys Met Lys Arg Ser Lys Ser Leu
        435                 440                 445
```

```
<210> SEQ ID NO 36
<211> LENGTH: 1341
<212> TYPE: DNA
<213> ORGANISM: Clostridium autoethanogenum
<220> FEATURE:
<221> NAME/KEY: misc_feature
<223> OTHER INFORMATION: CAETHG_0119, hydrogenase large subunit domain
      protein

<400> SEQUENCE: 36
gtgaataaaa gtcctgtaac tgttttaaaa gaaaaatgta caggttgtaa taagtgtata     60
agaacttgtc ctattcttgg tgcaaatgtt acagcaactg aaaatggtgt aagtaaggtt    120
tacatagatg aggaaagatg tattggatgc ggtgaatgtg taaaggtttg cgaacatggg    180
gctagagact ttaacgatag tacacaagac ttttttaagg atttgaaaaa aggcaaaaaa    240
ataacagtaa tagctgcacc atctattata gttaatatta aaaattacaa gaaatttttt    300
ggatatctta aatctttggg agtatctata atttatgatg tttctttcgg tgcagatatt    360
actacctggg cttatctaaa agcaatgaag gagaaaaata tttcttcttt aatatcacag    420
ccctgtccta tcgtggttaa ttatattgaa aaatataagc ctgaattaat agaatattta    480
gcgcctatac acagtcctat gatgtgtact gctgtttatc tgaaaaaata taagcatata    540
```

```
tgtgaagata tagcttttct gtcaccttgt attggcaagc taattgaaat caatgataag    600
aatacagatg ggtatgtgaa atataatgta acgtacaaaa agattttaga ttatttgaga    660
gataataatg tgaatttgaa caattacgat gaagttgaat ttgataatgt tcctgcttct    720 ttggggggttg tttatagttt accaggtgga ttaaaagcaa atgtaaaagc tagaactgaa    780
gaactacatg ttcttcagat agaaggacac aaagaggcaa ttgagtactt gaataagtat    840
tctgatagag ttaaagctaa taacttata cctagtttac ttgatatttt aaattgcaaa    900
aatggatgta atataggtac agcttcctta gacaatttaa cggaatatga tattcaatat    960
aggtttcatg atataaaggt ggaaaagtta agagaaaaaa ctggcttgtt taagaaaaaa    1020
atcaaatcaa tagacgagta ctttgataaa aatcttaatt taaacgattt tgtaagaaag    1080
tatactgcac agaaggttaa aaaaataatt gaacctaccc aaaaagatta tgacaacata    1140
tttgatgaga tgatgaaaac tacaacattg ggaaaagaat tcaattgttc cgcttgtgga    1200
tacagcactt gcaaagaaat ggtaaagatg attttaacg gcataaattc taaggaaaat    1260
tgtatttatt atgtgaagaa aaaatcaata tggaatatag cgaactggaa gaaaaaaatg    1320
aagaggtcaa agagtctata a                                             1341
```

<210> SEQ ID NO 37
<211> LENGTH: 461
<212> TYPE: PRT
<213> ORGANISM: Clostridium autoethanogenum
<220> FEATURE:
<221> NAME/KEY: MISC_FEATURE
<223> OTHER INFORMATION: CAETHG_0861, Cytochrome-c3 hydrogenase
      (EC:1.12.2.1)

<400> SEQUENCE: 37

Met Lys Lys Ile Thr Ile Asp Pro Ile Thr Arg Ile Ser Gly Phe
1               5                   10                  15

Leu Glu Thr Lys Val Gln Val Glu Lys Asn Ile Ile Val Asp Ala Glu
            20                  25                  30

Thr Ser Gly Leu Leu Phe Arg Gly Phe Glu Lys Met Leu Lys Asn Arg
        35                  40                  45

Glu Pro Leu Asp Ala Val Tyr Phe Thr Glu Arg Ile Cys Gly Ile Cys
    50                  55                  60

Ser Thr Ala His Ala Val Ala Ala Ala Thr Ala Leu Glu Asp Ala Leu
65                  70                  75                  80

Lys Ile Lys Ile Ser Val Asn Asp Ser Tyr Met Arg Asn Leu Ile His
                85                  90                  95

Gly Phe Glu Phe Ile Gln Asn His Ile Arg His Phe Tyr Asn Leu Thr
            100                 105                 110

Ile Pro Ser Tyr Val Lys Met Pro Asp Ile Asn Pro Leu Ser Ser Asn
        115                 120                 125

Gln Tyr Glu Asp Tyr Arg Leu Pro Tyr Asn Leu Asn Lys Lys Ile Ser
    130                 135                 140

Glu Asp Tyr Ile Glu Ser Ile Lys Tyr Ser Arg Leu Ala His Glu Gly
145                 150                 155                 160

Leu Ala Ile Leu Gly Gly Lys Ala Pro His Asn His Gly Ile Phe Val
                165                 170                 175

Gly Gly Val Thr Ile Asn Ile Asp Pro Tyr Lys Leu Thr Lys Val Lys
            180                 185                 190

Ser Ile Ile Ser Gln Ile Asn Lys Phe Val Ser Ser Val Met Leu Glu
        195                 200                 205

```
Asp Met Asn Ile Ile Ser Lys Tyr Tyr Ala Asp Tyr Phe Lys Met Gly
    210                 215                 220
Gly Ala Tyr Gly Asn Phe Met Thr Tyr Gly Ile Phe Asp Lys Tyr Ala
225                 230                 235                 240
Asp Pro Glu Ile Ser Tyr Val Gly Pro Ser Val Leu Ile Asn Gly Arg
                245                 250                 255
Lys Tyr Asn Phe Asn Ser Asn Lys Ile Thr Glu Asn Ile Leu His Thr
            260                 265                 270
Trp Tyr Thr Ser Asp Asp Glu Thr Ile Asn Leu Ser Lys Glu Thr Gly
        275                 280                 285
Tyr Ser Phe Ile Lys Ser Pro Thr Tyr Asn Gly Tyr Ser Met Glu Val
    290                 295                 300
Gly Pro Leu Ala Arg Leu Ile Leu Ser Gly Glu Tyr Thr Gly Gly Ser
305                 310                 315                 320
Ser Cys Met Asp Arg Asn Val Ala Arg Val Leu Glu Thr Lys Lys Ile
                325                 330                 335
Leu Glu Ile Met Gln Gly Leu Ala Asp Arg Ile Lys Leu Ile Pro Ala
            340                 345                 350
Glu Gln Arg Ile Tyr Gln Ile Pro Asp Lys Ala Phe Gly Ala Gly Leu
        355                 360                 365
Ile Asp Thr Thr Arg Gly Ser Leu Gly His Trp Ile Ser Ile Glu Asp
    370                 375                 380
Lys Phe Ile Lys His Tyr Asn Ile Ile Thr Pro Thr Val Trp Asn Met
385                 390                 395                 400
Gly Pro Arg Asn Gln Ser Gly Ala Leu Gly Ile Gly Glu Lys Ser Leu
                405                 410                 415
Val Gly Thr Lys Ile Lys Asp Ile Lys Gln Pro Ile Glu Val Gly Arg
            420                 425                 430
Ile Met Arg Ser Phe Asp Pro Cys Val Ser Cys Ala Thr His Leu Val
        435                 440                 445
Ser Asp Lys Tyr Glu Pro Val Asp Val Gln Val Ile Val
    450                 455                 460

<210> SEQ ID NO 38
<211> LENGTH: 1386
<212> TYPE: DNA
<213> ORGANISM: Clostridium autoethanogenum
<220> FEATURE:
<221> NAME/KEY: misc_feature
<223> OTHER INFORMATION: CAETHG_0861, Cytochrome-c3 hydrogenase
      (EC:1.12.2.1)

<400> SEQUENCE: 38
atgaaaaaga aaattacaat tgatccaatt acgagaataa gcggttttt  ggaaactaaa      60 gtgcaagtag aaaaaaatat tatagtagat gctgaaacta gtggattgct ttttagagga     120
tttgaaaaaa tgttaaagaa cagagagccg ctggatgcag tatattttac agaaagaatt     180
tgtggaatat gttcaacagc tcatgccgtg gcggctgcta cagctcttga agatgctttg     240
aagataaaaa ttagtgtaaa tgattcgtat atgcgtaatt taatacatgg ttttgaattt     300
atacaaaatc atataagaca tttttataat ttgaccatac caagttatgt gaagatgccc     360
gatataaatc ctctttcttc aaatcaatat gaagattata gattgcctta taacctaaat     420
aaaaagataa gtgaagatta tattgaaagt attaaataca gcaggttagc ccatgaaggg     480
ttggctatcc ttggaggaaa agccccccat aatcatggaa tttttgttgg aggagttacc     540
ataaatatag atccatataa actcacaaaa gttaaatcta ttatttctca aattaataaa     600
```

```
tttgtaagta gtgttatgtt agaggacatg aacataattt caaaatacta tgctgattat    660
tttaaaatgg gaggagctta tggaaacttt atgacttatg aattttttga caagtatgct    720
gatcctgaga taagttatgt aggaccttct gtattaataa atggacgaaa gtataatttc    780
aatagtaata aaattacgga aaacatactc cacacctggt atacaagcga tgatgaaacg    840
ataaatttat ctaaagaaac aggttacagc tttataaaat cgccaaccta taatggatat    900
tctatggaag taggacctct agcaagattg atactttcag gtgagtatac tggtggaagt    960
tcatgtatgg acagaaatgt tgccagagta cttgaaacaa aaagattttt agaaattatg   1020
caaggacttg cagatagaat taagcttatt ccagcagaac aaagaatata tcaaatacca   1080
gataaagcat tggtgcagg attaattgac acaactagag gatccttggg acactggata   1140
agtatagaag ataaatttat aaagcattac aatattataa ctcctacagt gtggaatatg   1200
gggccaagaa atcaatcagg tgcgcttgga attggagaaa atctttagt tggaacgaaa   1260 ataaaagata taaagcagcc tatagaagtt gggagaatta tgagatcttt tgatccttgt   1320
gtttcctgtg caacgcatct tgtaagtgat aaatatgaac cagtggatgt acaggttata   1380
gtatga                                                              1386
```

<210> SEQ ID NO 39
<211> LENGTH: 250
<212> TYPE: PRT
<213> ORGANISM: Clostridium autoethanogenum
<220> FEATURE:
<221> NAME/KEY: MISC_FEATURE
<223> OTHER INFORMATION: CAETHG_0862, hydrogenase (NiFe) small subunit
      HydA (EC:1.12.99.6)

<400> SEQUENCE: 39

```
Met Asn Ala Arg Ser Lys Val Ile Cys Pro Leu Ile Val Asp Lys Glu
1               5                   10                  15

Arg Ser Ser Lys Ala Phe Thr Ser Glu Ala Ile Asp Leu Ile Glu Arg
            20                  25                  30

Arg Lys Thr Lys Lys Leu Asn Ala Ile Trp Leu Glu Val Thr Gly Cys
        35                  40                  45

Ser Gly Asn Ile Ile Ser Phe Leu Asn Ser Glu Asn Pro Gly Leu Asp
    50                  55                  60

Tyr Ile Leu Glu Lys Leu Ile Asn Leu Lys Tyr Asn Asn Thr Leu Met
65                  70                  75                  80

Thr Ser Glu Gly Glu Tyr Ala Phe Lys Gln Phe Leu Asp Thr Leu Asn
                85                  90                  95

Thr Glu Phe Ile Leu Leu Val Asp Gly Ala Val Ser Thr Ala Gln Asn
            100                 105                 110

Gly Phe Tyr Asn Ile Val Ala Asn Tyr Glu Gly Asn Pro Val Thr Ala
        115                 120                 125

Leu Glu Ala Val Lys Met Ala Gly Glu Lys Ala Lys His Val Leu Cys
    130                 135                 140

Val Gly Thr Cys Ala Ser Tyr Gly Gly Ile Ser Ala Ala Arg Pro Asn
145                 150                 155                 160

Pro Ser Glu Ser Lys Ser Val Lys Glu Ile Leu Asn Arg Glu Val Ile
                165                 170                 175

Arg Leu Pro Gly Cys Pro Cys His Pro Asp Trp Val Val Gly Thr Leu
            180                 185                 190

Ala His Leu Val Ala Phe Gly Lys Pro Gln Leu Asp Lys Glu Gly Arg
        195                 200                 205
```

Pro Leu Leu Phe Tyr Gly Ile Thr Ile His Asp Ser Cys Thr Arg Arg
    210                 215                 220

Gly Phe Phe Asp Asn Arg Ile Phe Ala Lys Lys Phe Gly Glu Asn Gly
225                 230                 235                 240

Cys Met Phe Lys Leu Gly Cys Arg Gly Leu
            245                 250

<210> SEQ ID NO 40
<211> LENGTH: 753
<212> TYPE: DNA
<213> ORGANISM: Clostridium autoethanogenum
<220> FEATURE:
<221> NAME/KEY: misc_feature
<223> OTHER INFORMATION: CAETHG_0862, hydrogenase (NiFe) small subunit
      HydA (EC:1.12.99.6)

<400> SEQUENCE: 40
atgaatgctc gaagcaaggt tatatgtcct ttaatcgtag ataaggaacg cagttcaaag      60
gcttttacta gtgaagctat agatttaatt gaaaggagaa agacgaaaaa attaaatgct    120
atatggcttg aagtaacagg atgttcagga aatatcattt ctttttttaaa tagtgaaaat    180 cctggactcg attatatttt ggaaaaactc attaatttaa aatacaacaa tactctaatg    240
acttcagaag gggagtatgc ctttaaacaa ttcttagata cattgaatac tgaatttata    300
ctattagtag atggagcagt atctactgcc agaacggtt tttataatat tgttgccaat     360
tatgaaggaa accctgttac tgcacttgaa gctgtaaaaa tggcaggaga aaaagcaaag    420
catgttctct gtgtaggaac ttgtgcatcc tatggtggaa tttctgccgc caggccaaac    480
ccttcagaaa gcaaaagtgt taaagaaata ctaaatcgtg aagtcataag acttccaggc    540
tgtccatgcc acccggattg ggtagttgga acttttagcac acttggttgc ttttggaaaa    600
ccacaattgg ataaagaagg aagacctctt ctttttttatg gaattaccat tcatgatagt    660
tgtacaagaa gaggattttt tgataacaga atttttgcaa aaaaatttgg agaaaatgga    720
tgcatgttta aacttggatg caggggcctg taa                                 753

<210> SEQ ID NO 41
<211> LENGTH: 154
<212> TYPE: PRT
<213> ORGANISM: Clostridium autoethanogenum
<220> FEATURE:
<221> NAME/KEY: MISC_FEATURE
<223> OTHER INFORMATION: CAETHG_0860, hydrogenase maturation protease
      (EC:3.4.23.-), WP_013239503.1

<400> SEQUENCE: 41

Met Lys Ala Lys Val Ile Ala Leu Gly Asn Ile Leu Met Glu Asp Asp
1               5                   10                  15

Gly Ile Gly Ile Arg Ile Leu Glu Asn Ile Lys Glu Glu Leu Thr His
            20                  25                  30

Asn Asn Val Glu Ser Ile Ser Gly Glu Thr Asp Val Glu Tyr Cys Ile
        35                  40                  45

Ser Gln Val Lys Asp Gly Asp Phe Ile Phe Ile Asp Ala Ser Tyr
    50                  55                  60

Asn Gly Lys Val Pro Gly Thr Ile Thr Val Ala Ser Leu Gln Asp Tyr
65                  70                  75                  80

Lys Cys Lys Lys Lys Tyr Tyr Thr Gln His Ser Tyr Ser Phe Ile Asp
                85                  90                  95

Leu Ile Gly Val Tyr Tyr Lys Ser Leu Thr Gly Phe Ile Ile Glu Ile

```
                    100                 105                 110
Glu Ala Ala Ser Ile Ser Phe Lys Leu Gly Leu Ser His Asn Leu Gln
                115                 120                 125

Asn Lys Leu Lys Ser Ile Ser Lys Asp Val Leu Lys Asn Ile Phe Leu
            130                 135                 140

Arg Leu Asn Asp Arg Ala Trp Glu Glu Lys
145                 150

<210> SEQ ID NO 42
<211> LENGTH: 465
<212> TYPE: DNA
<213> ORGANISM: Clostridium autoethanogenum
<220> FEATURE:
<221> NAME/KEY: misc_feature
<223> OTHER INFORMATION: CAETHG_0860, hydrogenase maturation protease
      (EC:3.4.23.-)

<400> SEQUENCE: 42
atgaaagcaa aagttattgc tctaggaaac atattgatgg aggatgatgg cattggaatt      60
agaatactgg aaaatataaa ggaggagctt acgcataaca atgttgaatc tataagtgga     120
gagacagatg tggaatattg catttcccaa gtaaaagatg gtgattttat atttataata     180
gatgcttctt ataatggaaa agttccaggt acgataacag ttgccagctt acaagattat     240
aagtgtaaaa agaaatatta tactcagcat agctatagtt tcatagattt gataggagtt     300
tattacaaat ccttaactgg atttattatt gaaattgaag cagctagtat aagctttaaa     360
ttgggactta gccataattt acagaataag cttaagtcta tttcaaaaga tgtattgaaa     420
aatatttttc tgagattgaa tgatagagca tgggaggaaa aatag                     465

<210> SEQ ID NO 43
<211> LENGTH: 334
<212> TYPE: PRT
<213> ORGANISM: Clostridium autoethanogenum
<220> FEATURE:
<221> NAME/KEY: MISC_FEATURE
<223> OTHER INFORMATION: CAETHG_0369, hydrogenase expression/formation
      protein HypE

<400> SEQUENCE: 43

Met Asp Lys Thr Val Thr Leu Ala His Gly Ala Gly Gly Arg Gln Thr
1               5                   10                  15

Ser Glu Leu Ile Asp Gln Val Phe Arg Ala His Phe Ser Asn Pro Asp
                20                  25                  30

Leu Thr Ala Asp Asp Ala Ala Val Leu Asn Ile Lys Gly Gly Lys Leu
            35                  40                  45

Ala Phe Thr Thr Asp Gly Phe Ile Val Ser Pro Ser Glu Phe Pro Gly
        50                  55                  60

Gly Asn Ile Gly Lys Leu Ser Ile Cys Gly Thr Val Asn Asp Leu Ser
65                  70                  75                  80

Cys Met Gly Ala Lys Pro Leu Tyr Leu Ser Cys Ala Phe Val Ile Glu
                85                  90                  95

Glu Gly Phe Pro Met Asp Lys Leu Glu Lys Ile Ala Ala Ala Met Glu
                100                 105                 110

Lys Thr Ala Lys Glu Ala Gly Val Lys Ile Ala Ala Gly Asp Thr Lys
            115                 120                 125

Val Ala Gly Lys Gly Gln Val Asp Gly Val Phe Ile Thr Thr Thr Gly
        130                 135                 140

Ile Gly Gln Ile Met Asp Asp Ala Asn Thr Ser Gly Phe Asn Ala Lys
```

Pro Gly Asp Ala Ile Ile Val Thr Gly Asp Ile Gly Arg His Gly Cys
145                 150                 155                 160

Thr Val Leu Leu Ala Arg Asp Glu Phe Gly Ile Glu Ala Asp Val Thr
                165                 170                 175

Ser Asp Cys Ala Pro Leu Trp Gly Thr Val Lys Ala Met Phe Asp Thr
            180                 185                 190

Ser Lys Asp Ile His Val Ile Arg Asp Ala Thr Arg Gly Val Gly
        195                 200                 205

Thr Val Leu Tyr Glu Ile Ala Glu Gln Ser Lys Val Gly Ile Arg Leu
    210                  215                 220

Asp Ser Lys Ser Ile Pro Val Ala Asp Gly Val Lys Gly Val Cys Gly
225                 230                 235                 240

Met Leu Gly Leu Glu Pro Leu Tyr Leu Ala Cys Glu Gly Arg Leu Val
            245                 250                 255

Val Phe Ala Pro Lys Glu Ile Ala Pro Lys Leu Val Asp Thr Leu His
        260                 265                 270

Lys Gly Lys Tyr Ser Lys Asp Ala Ala Ile Ile Gly Glu Val Thr Cys
    275                 280                 285

Asp Met Pro Gly Arg Val Ile Val Lys Thr Glu Ile Gly Ala Glu Thr
290                 295                 300

Leu Leu Pro Pro Pro Gly Gly Glu Leu Leu Pro Arg Ile Cys
305                 310                 315                 320

325                 330

<210> SEQ ID NO 44
<211> LENGTH: 1005
<212> TYPE: DNA
<213> ORGANISM: Clostridium autoethanogenum
<220> FEATURE:
<221> NAME/KEY: misc_feature
<223> OTHER INFORMATION: CAETHG_0369, hydrogenase expression/formation
      protein HypE

<400> SEQUENCE: 44
atggataaaa cagttacact agctcatgga gctggaggaa gacaaacatc agaattaata      60
gatcaggttt ttagagctca tttttcgaat cctgacctga cagcagatga tgctgcagta     120
ttgaacatta aaggaggaaa actagctttt acaacagatg gatttattgt ttctccatcg     180
gaatttccag gtggaaatat tggcaaatta agcatttgtg gtacagtaaa tgacttatcc     240
tgtatgggag cgaaacctct gtatttatct tgtgcttttg ttattgaaga gggcttccca     300
atggataaat tagagaaaat tgcagcagcc atggaaaaga ctgcaaagga agcaggggtt     360
aaaatagccg caggagatac aaaggttgct ggaaaagggc aagttgatgg agtatttata     420
acaacaacag gtataggaca gattatggat gatgctaata cctctggttt taatgcaaaa     480
ccaggcgatg cgattattgt aaccggtgat ataggcgac atggatgtac tgttttactg     540
gcacgagatg agtttggaat tgaagcagat gtaaccagtg attgtgcacc attatggggt     600
acagtaaaag ctatgtttga tacgtcaaaa gatattcatg taatcagaga tgctacacgt     660
ggaggtgtcg gtacggtatt tatgaaatt gccgagcaga gcaaagttgg aattagatta     720
gattcaaaga gtataccggt agcagatggt gtaaaaggtg tatgcggcat gctgggttg     780 gaaccactat atcttgcatg tgaaggaaga cttgtagttt ttgctccaaa agaaattgct     840
ccaaaacttg tggatacatt acataaaggt aaatattcaa aagatgcagc cattattggt     900
gaggtcactt gtgatatgcc tggacgtgtt attgtaaaaa cagaaatcgg tgctgaaaca     960
ttgctgccac ctccaggagg agaattgctt ccaagaatat gttaa         1005

<210> SEQ ID NO 45
<211> LENGTH: 352
<212> TYPE: PRT
<213> ORGANISM: Clostridium autoethanogenum
<220> FEATURE:
<221> NAME/KEY: MISC_FEATURE
<223> OTHER INFORMATION: CAETHG_0370, hydrogenase expression/formation protein HypD

<400> SEQUENCE: 45

```
Met Ala Glu Asn Ile Lys Lys Thr Ala Lys Glu Ile Ile Glu Ser Tyr
1               5                   10                  15

Asp Gly Pro Lys Ile Arg Ile Met Glu Val Cys Gly Thr His Thr His
            20                  25                  30

Glu Ile Phe Arg Leu Gly Ile Arg Asn Ile Ile Pro Glu Asn Ile Glu
        35                  40                  45

Leu Ile Ser Gly Pro Gly Cys Pro Val Cys Val Thr Pro Val Gly Phe
50                  55                  60

Ile Asp Glu Ala Ile Met Leu Ala Leu Asp His Asn Ala Thr Ile Cys
65                  70                  75                  80

Thr Phe Gly Asp Leu Val Arg Val Pro Gly Ser Glu Met Asn Leu Ala
                85                  90                  95

Gly Ala Arg Ser Lys Gly Ala Lys Val Gln Ile Val Tyr Ser Pro Ile
            100                 105                 110

Asp Ala Tyr Glu Tyr Ala Arg Asp His Leu Asp Glu Gln Val Val Phe
        115                 120                 125

Leu Ser Val Gly Phe Glu Thr Thr Thr Pro Ala Ser Cys Leu Ala Val
130                 135                 140

Lys Lys Ala Lys Gly Ala Glu Leu Lys Asn Phe Ala Leu Leu Thr Ala
145                 150                 155                 160

Asn Lys Thr Met Pro Gly Val Tyr Lys Thr Leu Lys Asn Ser Ala Asp
                165                 170                 175

Ala Phe Leu Tyr Pro Gly His Val His Ala Ile Thr Gly Thr Glu Leu
            180                 185                 190

Cys Glu Ser Leu Val Asn Glu Gly Val Ser Gly Val Ile Thr Gly Phe
        195                 200                 205

Thr Ala Asn Glu Ile Met Thr Ala Leu Ala Val Val Ile Thr Lys Leu
210                 215                 220

Gln Glu Gly Glu Ser Phe Phe Lys Asn Cys Tyr Pro Arg Val Val Thr
225                 230                 235                 240

Tyr Glu Gly Ser Lys Ala Ala Gln Thr Ile Val Ser Glu Val Met Glu
                245                 250                 255

Asp Cys Asp Ser Glu Trp Arg Gly Leu Gly Val Ile Lys Asn Ser Gly
            260                 265                 270

Leu Lys Leu Lys Glu Ala Tyr Lys Glu Phe Asp Ala Arg Asp Lys Phe
        275                 280                 285

His Leu Gly Lys Val Glu Gly Arg Ser Asn Pro Ala Cys Arg Cys Gly
290                 295                 300

Asp Val Leu Gln Gly Lys Cys Lys Pro Ser Asp Cys Lys Val Phe Gly
305                 310                 315                 320

Lys Gly Cys Thr Pro Leu His Pro Val Gly Ala Cys Met Val Ser Asn
                325                 330                 335

Glu Gly Ala Cys Ser Ala Tyr Tyr Gln Tyr Gly Gly Lys Ile Asn Gly
            340                 345                 350
```

```
<210> SEQ ID NO 46
<211> LENGTH: 1059
<212> TYPE: DNA
<213> ORGANISM: Clostridium autoethanogenum
<220> FEATURE:
<221> NAME/KEY: misc_feature
<223> OTHER INFORMATION: CAETHG_0370, hydrogenase expression/formation
      protein HypD

<400> SEQUENCE: 46
atggctgaga acataaaaaa aactgcaaag gagattattg aatcctatga tggaccaaag      60
atccgtatta tggaggtttg cggaacgcat acccatgaga tattcagact tggaatcaga     120
aatataatac cagaaaatat tgaactcata tcaggaccag atgtccggt tgtgttaca      180 ccagttggct ttattgatga agctattatg ctggcccttg accataatgc taccatatgt     240
acctttggag atttagtaag agtgcctggt tcagaaatga accttgctgg agccagatca     300
aaaggcgcca agttcaaat agtatattca cctattgatg cttatgagta tgctagagac     360
caccttgatg agcaggtagt attcttatca gtaggatttg agacaaccac acctgccagc     420
tgtctggctg taaaaaaggc aaaggtgca gaacttaaaa attttgcatt acttacggca     480
aacaaaacca tgccgggagt atacaaaaca ctaaaaaata gtgcagatgc atttttatat     540
cctggccatg tacatgctat tacaggtacg gagttatgtg agtctttagt taacgaaggc     600
gttagtggag taataacagg tttttactgca aatgaaatta tgacagcact tgctgtagta     660
atcacaaaat acaagaagg agaaagcttt tttaaaaact gttatccgag agttgtaaca     720
tatgaaggca gtaaagcggc tcagactatt gtatctgaag tcatggagga ctgcgattct     780
gagtggagag gtcttggtgt tatcaaaaat tcaggactta aattgaagga agcttataaa     840
gagtttgatg ccagagacaa atttcattta ggaaaagtag agggaagaag taatccggct     900
tgccgatgtg gtgatgtttt gcagggaaaa tgcaagccat cggattgcaa agtatttggc     960
aaagggtgta cgccactaca tcctgttgga gcatgtatgg tatctaatga aggagcatgt    1020
tcagcatatt atcagtatgg aggaaaaata aatggataa                           1059

<210> SEQ ID NO 47
<211> LENGTH: 68
<212> TYPE: PRT
<213> ORGANISM: Clostridium autoethanogenum
<220> FEATURE:
<221> NAME/KEY: MISC_FEATURE
<223> OTHER INFORMATION: CAETHG_0371, hydrogenase assembly chaperone
      hypC/hupF

<400> SEQUENCE: 47

Met Cys Val Gly Leu Pro Ala Arg Val Val Lys Val Lys Glu Gly Met
1               5                   10                  15

Ala Leu Ile Asp Ala Ser Gly Ala Lys Arg Lys Val Ser Ala Glu Leu
            20                  25                  30

Ile Asp Glu Leu Glu Pro Gly Asp Tyr Val Met Val His Ala Gly Ile
        35                  40                  45

Ala Ile Ser Lys Ile Thr Asn Asp Asp Gln Ser Glu Thr Asp Lys Ile
    50                  55                  60

Met Glu Glu Leu
65

<210> SEQ ID NO 48
<211> LENGTH: 207
```

```
<212> TYPE: DNA
<213> ORGANISM: Clostridium autoethanogenum
<220> FEATURE:
<221> NAME/KEY: misc_feature
<223> OTHER INFORMATION: CAETHG_0371, hydrogenase assembly chaperone
      hypC/hupF

<400> SEQUENCE: 48
atgtgtgtag gtttaccagc aagagttgta aaggttaaag aaggaatggc tctaattgat        60
gcttcaggag caaaaagaaa ggtatctgca gaattaatcg atgaattgga accaggcgat       120
tacgttatgg ttcatgcagg aatcgccatt tcaaaaatta caaacgatga tcagagtgaa       180
acagataaaa tcatggagga attataa                                           207

<210> SEQ ID NO 49
<211> LENGTH: 799
<212> TYPE: PRT
<213> ORGANISM: Clostridium autoethanogenum
<220> FEATURE:
<221> NAME/KEY: MISC_FEATURE
<223> OTHER INFORMATION: CAETHG_0372, (NiFe) hydrogenase maturation
      protein HypF

<400> SEQUENCE: 49
```

Met Lys Asp Tyr Lys Thr Leu Ser Ile Arg Val Tyr Gly Ile Val Gln
1               5                   10                  15

Gly Val Gly Phe Arg Pro Thr Val Ser Arg His Ala Asp Lys Asn His
            20                  25                  30

Ile Arg Gly Ser Val Cys Asn Lys Gly Pro Tyr Val Glu Ile Trp Ala
        35                  40                  45

Gln Gly Ser Glu Ser Glu Leu Glu Gly Phe Leu Tyr Asp Leu Glu His
    50                  55                  60

Asn Pro Pro Lys Arg Ser Ser Ile Leu Lys Ile Asp Val His Lys Glu
65                  70                  75                  80

Glu Glu Ser Glu Lys Phe Gln Asp Phe Glu Ile Ile Glu Ser Glu His
                85                  90                  95

Val Gln Gly Glu Ile Phe Val Ser Pro Asp Ile Ala Ile Cys Pro Glu
            100                 105                 110

Cys Lys Arg Glu Leu Phe Asp Lys Asn Asn Arg Arg Tyr Leu His Pro
        115                 120                 125

Phe Ile Asn Cys Thr Cys Cys Gly Pro Arg Leu Thr Ile Leu Asp Ser
    130                 135                 140

Met Pro Tyr Asp Arg Val Arg Thr Ser Met Gly Glu Phe Pro Met Cys
145                 150                 155                 160

Pro Glu Cys Glu Tyr Glu Tyr Thr His Ala Glu Thr Arg Arg Tyr Asp
                165                 170                 175

Ala Gln Pro Val Cys Cys Asn Glu Cys Gly Pro Glu Val Tyr Leu Ile
            180                 185                 190

Gly Arg Gly Glu Arg Gly Arg Thr Ala Ile Thr Tyr Thr Arg Gln Val
        195                 200                 205

Ile His Asp Gly Gly Ile Ala Ala Ile Lys Gly Ile Gly Gly Phe His
    210                 215                 220

Leu Cys Cys Asp Ala Thr Asn Gln Glu Ala Val Glu Arg Leu Arg Lys
225                 230                 235                 240

Leu Lys Thr Arg Pro Ala Lys Pro Phe Ala Val Met Met Arg Asp Met
                245                 250                 255

Glu Thr Val Glu Arg Glu Cys Glu Val Thr Lys Val Gln Lys Glu Val
            260                 265                 270

```
Leu Asp Gly His Gln Lys Pro Ile Ile Leu Lys Arg Lys Gln Ser
        275                 280                 285

Lys Met Val Cys Asp Ala Val Thr Pro Asp Asn Pro Lys Ile Gly Val
    290                 295                 300

Met Leu Pro Tyr Ala Pro Val Gln Leu Leu Ile Phe Thr Tyr Asp Asp
305                 310                 315                 320

Asp Ile Val Met Pro Asp Cys Leu Val Met Thr Ser Gly Asn Thr Ser
                325                 330                 335

Gly Ala Pro Ile Cys Arg Asp Asp Asn Asp Ala Ile Thr Glu Leu Ser
                340                 345                 350

Lys Met Cys Asp Val Ile Leu Ser His Asn Arg Met Ile Arg Ile Arg
            355                 360                 365

Ala Asp Asp Ser Val Met Asp Phe Phe Glu Glu Lys Pro Tyr Met Ile
    370                 375                 380

Arg Arg Ser Arg Gly Tyr Ala Pro Leu Pro Phe Met Val Ser Asn Gly
385                 390                 395                 400

Phe Lys Gly Glu Val Leu Ala Val Gly Gly Glu Leu Lys Asn Thr Phe
                405                 410                 415

Cys Ile Gly Lys Asn Asp Leu Phe Tyr Gln Ser Pro Tyr Val Gly Asp
                420                 425                 430

Met Glu Asp Leu Arg Thr Val Lys Ala Leu Lys Glu Ser Ile Thr Arg
    435                 440                 445

Leu Glu Thr Leu Leu Glu Thr Thr Pro Thr Ile Val Ala Cys Asp Met
450                 455                 460

His Pro Lys Tyr Asn Thr Thr Cys Ile Ala Gln Ile Gly Ile Pro
465                 470                 475                 480

Val Phe Gln Val Gln His His Tyr Ala His Ile Leu Ser Cys Met Ala
                485                 490                 495

Glu Asn Asp Tyr Ser Asp Pro Val Ile Gly Val Ser Phe Asp Gly Thr
                500                 505                 510

Gly Tyr Gly Thr Asp Ala Thr Ile Trp Gly Gly Glu Leu Leu Glu Val
            515                 520                 525

Thr Tyr Asp Gly Phe Glu Arg Leu Gly Ser Ile Lys Pro Phe Ile Gln
        530                 535                 540

Ile Gly Gly Asp Met Ser Ala Lys Glu Gly Trp Arg Ile Ala Val Ser
545                 550                 555                 560

Met Ile Tyr Ser Ile Tyr Lys Asp Lys Glu Lys Ala Ala Glu Val Val
                565                 570                 575

Arg Gln Leu Lys Leu Cys Asp Glu Lys Asn Cys Asp Val Gln Phe Met
                580                 585                 590

Met Ala Asp Asn Lys Ile Asn Ser Ile Thr Ser Thr Ala Gly Arg
    595                 600                 605

Leu Phe Asp Ala Val Ser Ala Ile Leu Asn Ile Arg Lys Gln Ser Ser
    610                 615                 620

Phe Glu Gly Glu Ala Ser Thr Thr Leu Glu Phe Ala Ala Glu Ala Tyr
625                 630                 635                 640

Glu Glu Lys His Ala Asp His Asn Ser Gly Ser Lys Ile Thr Asp Glu
                645                 650                 655

Asp Ser Ile Glu Leu Ser Asn Leu Val Tyr Glu Asn Ser Asn Gly Gln
                660                 665                 670

Leu Ile Phe Ala Thr Asp Val Leu Val Lys Lys Ile Ile Glu Glu Thr
                675                 680                 685
```

```
Leu Thr Gly Lys Asp Ala Ala Met Leu Ala Tyr Phe Phe His Glu Lys
            690                 695                 700
Leu Ser Asp Met Ile Ala Ala Gly Cys Ile Gln Ala Ser Arg Asn Thr
705                 710                 715                 720
Gly Ile Lys Thr Ile Ala Leu Ser Gly Gly Val Tyr Gln Asn Gln Leu
                725                 730                 735
Leu Leu Lys Met Ser Leu Asp Arg Leu Arg Lys Leu Gly Phe Lys Val
            740                 745                 750
Leu Ile His Ser Leu Leu Pro Pro Asn Asp Gly Ile Ala Leu Gly
        755                 760                 765
Gln Ala Val Ala Ala Met Glu His Ile Asn Lys Leu Lys Lys Gly Glu
    770                 775                 780
Glu Asn Asn Tyr Val Cys Arg Phe Thr Ser Lys Ser Cys Lys Gly
785                 790                 795

<210> SEQ ID NO 50
<211> LENGTH: 2400
<212> TYPE: DNA
<213> ORGANISM: Clostridium autoethanogenum
<220> FEATURE:
<221> NAME/KEY: misc_feature
<223> OTHER INFORMATION: CAETHG_0372, (NiFe) hydrogenase maturation
      protein HypF

<400> SEQUENCE: 50
atgaaagatt ataaaacttt atctattaga gtctatggta ttgtgcaggg agttggattt      60
agacctacag taagccggca tgcagataaa aatcatatac ggggaagtgt atgcaataaa    120
ggaccttatg tggaaatatg ggctcaaggt agtgaaagtg aattagaggg ttttttgtac    180
gatttagaac acaatcctcc aaagcgttca tcaatattaa aaattgatgt gcataaagag    240
gaagagtcag aaaaatttca ggactttgaa attattgaaa gtgaacatgt acaaggtgag    300 attttttgtat ctcctgatat tgccatctgt ccagagtgta aaagagaact ttttgataag    360
aataacagac gatatcttca tccctttata aactgtacgt gctgcggacc aagacttact    420
attttagatt ccatgcctta tgatcgtgta cgtaccagca tgggtgaatt tccaatgtgt    480
ccggagtgtg aatatgaata tactcatgca gaaactcgaa gatatgatgc gcagccggta    540
tgctgcaatg aatgcggccc ggaggtttac ttaattggaa gaggcgagcg gggcaggact    600
gcaattactt atacaagaca agtaatccat gatggaggga ttgcagctat aaagggaatt    660
ggaggtttcc atctttgctg tgatgccaca aatcaggaag ctgtagagag cttagaaaa    720 ttaaagacaa gacctgcaaa gccctttgca gttatgatgc gggacatgga aactgtagaa    780
cgtgaatgtg aagttacaaa agttcaaaaa gaagtactgg atggtcatca gaaaccaatt    840
atacttctga aagaaagca agcaaaatg tgtgtgatg ctgtgacacc tgataatcca    900
aagattggag ttatgcttcc ctatgctcct gttcaacttt tgatatttac atatgatgat    960
gatatagtta tgccggattg cctggttatg acaagtggta atacatcagg tgcaccaata   1020
tgtagagatg acaatgatgc aataacagaa ttatcaaaaa tgtgtgatgt tattttatca   1080
cataacagaa tgattcgtat tcgtgcagat gactcggtta tggatttctt tgaagaaaaa   1140
ccttatatga taaggcgttc cagaggatat gcgccgcttc cgtttatggt ttcaaacgga   1200
tttaaagggg aagtactggc agttggtggt gaactcaaga atactttttg tataggcaaa   1260
aatgatttgt tttatcagtc ccctatgtt ggtgacatgg aagatttgag acagtaaaa   1320 gcattgaaag agtctattac aagattggaa actctgcttg agacgacgcc aacaattgtg   1380
```

-continued

```
gcatgtgaca tgcatccaaa gtataatact acgtgcattg cacaggaaat tggaattccc   1440
gtatttcagg ttcaacatca ttatgcacat attttatctt gtatggctga aaatgattat   1500
tctgatccag ttataggcgt ttcatttgat ggaacaggat atggaacaga tgcaaccatc   1560
tggggtggag agctattaga agttacttat gatggatttg aaaggcttgg cagcataaaa   1620
ccttttattc agatcggtgg tgacatgtca gctaaagagg gctggagaat tgcggtatcc   1680
atgatttaca gtatatacaa agataaagaa aaagcagctg aagttgtaag acagcttaaa   1740
ttatgtgatg agaagaactg cgatgttcag tttatgatgg ctgacaacaa aataaacagc   1800
ataacatcta cgagtgcagg gcgtttgttt gatgctgtaa gtgctatctt gaatatcaga   1860
aaacaatcat cttttgaagg ggaagcttct actacccttg aatttgcagc agaggcttat   1920
gaagaaaaac atgcggacca taatagtggc agcaaaatta ctgatgagga tagtattgaa   1980
ctttcaaatc ttgtttatga gaattcaaat ggacagctaa ttttcgcaac agatgtttta   2040
gtaaagaaaa tcatagagga aactttaact gggaaagatg cagcgatgct tgcttacttc   2100
ttccatgaaa aattgtcaga tatgattgca gctggatgta caagcttc tagaaacact    2160
ggaatcaaaa ccatagcatt aagcggagga gtatatcaaa accagttatt attaaaaatg   2220
agcctagacc gtttgagaaa acttggattt aaagttttaa ttcatagttt gttgccgcca   2280
aatgatggtg aatagcact  aggtcaggca gtagcagcaa tggaacatat aaataaatta   2340
aaaaagggg aggagaataa ctatgtgtgt aggtttacca gcaagagttg taaggttaa    2400
```

<210> SEQ ID NO 51
<211> LENGTH: 344
<212> TYPE: DNA
<213> ORGANISM: Clostridium autoethanogenum
<220> FEATURE:
<221> NAME/KEY: misc_feature
<223> OTHER INFORMATION: CAETHG_1576, sequence of intron targeting
      region

<400> SEQUENCE: 51

```
aagcttataa ttatccttaa ttgtcgttgt agtgcgccca gatagggtgt taagtcaagt     60
agtttaaggt actactctgt aagataacac agaaaacagc caacctaacc gaaaagcgaa    120
agctgatacg ggaacagagc acggttggaa agcgatgagt tacctaaaga caatcgggta    180
cgactgagtc gcaatgttaa tcagatataa ggtataagtt gtgtttactg aacgcaagtt    240
tctaatttcg gttacaatcc gatagaggaa agtgtctgaa acctctagta caaagaaagg    300
taagttagct acaacgactt atctgttatc accacatttg taca                    344
```

<210> SEQ ID NO 52
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer Og119f

<400> SEQUENCE: 52
tgcttgtctt atcatactta taagc                                          25

<210> SEQ ID NO 53
<211> LENGTH: 25
<212> TYPE: DNA
<213> ORGANISM: Artificial sequence
<220> FEATURE:

<223> OTHER INFORMATION: Synthetic nucleotide
<220> FEATURE:
<221> NAME/KEY: misc_feature
<223> OTHER INFORMATION: reverse primer Og120f

<400> SEQUENCE: 53
tagagaatac acatccagag ttaat    25

<210> SEQ ID NO 54
<211> LENGTH: 344
<212> TYPE: DNA
<213> ORGANISM: Clostridium autoethanogenum
<220> FEATURE:
<221> NAME/KEY: misc_feature
<223> OTHER INFORMATION: CAETHG_0110, sequence of intron targeting
      region

<400> SEQUENCE: 54
aagcttataa ttatccttag aattctgtaa ggtgcgccca gatagggtgt taagtcaagt    60
agtttaaggt actactctgt aagataacac agaaaacagc caacctaacc gaaaagcgaa   120
agctgatacg ggaacagagc acggttggaa agcgatgagt tacctaaaga caatcgggta   180
cgactgagtc gcaatgttaa tcagatataa ggtataagtt gtgtttactg aacgcaagtt   240
tctaatttcg attaattctc gatagaggaa agtgtctgaa acctctagta caaagaaagg   300
taagttaatc ttacagactt atctgttatc accacatttg taca                    344

<210> SEQ ID NO 55
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer Og121f

<400> SEQUENCE: 55
aggcatatta tagtggaaat tttga    25

<210> SEQ ID NO 56
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer Og122r

<400> SEQUENCE: 56
tgtaagcaca attttctta ttgtc    25

<210> SEQ ID NO 57
<211> LENGTH: 344
<212> TYPE: DNA
<213> ORGANISM: Clostridium autoethanogenum
<220> FEATURE:
<221> NAME/KEY: misc_feature
<223> OTHER INFORMATION: CAETHG_0860, sequence of intron targeting
      region

<400> SEQUENCE: 57
aagcttataa ttatccttac caggcgtgga ggtgcgccca gatagggtgt taagtcaagt    60
agtttaaggt actactctgt aagataacac agaaaacagc caacctaacc gaaaagcgaa   120

```
agctgatacg ggaacagagc acggttggaa agcgatgagt tacctaaaga caatcgggta    180
cgactgagtc gcaatgttaa tcagatataa ggtataagtt gtgtttactg aacgcaagtt    240
tctaatttcg gttcctggtc gatagaggaa agtgtctgaa acctctagta caaagaaagg    300
taagttatac tccacgactt atctgttatc accacatttg taca                     344
```

<210> SEQ ID NO 58
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer Og117f
<400> SEQUENCE: 58

```
agtccttgca taatttctaa aatct                                           25
```

<210> SEQ ID NO 59
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer Og118r
<400> SEQUENCE: 59

```
taagtagtgt tatgttagag gacat                                           25
```

<210> SEQ ID NO 60
<211> LENGTH: 344
<212> TYPE: DNA
<213> ORGANISM: Clostridium autoethanogenum
<220> FEATURE:
<221> NAME/KEY: misc_feature
<223> OTHER INFORMATION: CAETHG_3569, sequence of intron targeting
      region <400> SEQUENCE: 60

```
aagcttataa ttatccttaa ttgacgttct agtgcgccca gatagggtgt taagtcaagt    60
agtttaaggt actactctgt aagataacac agaaaacagc caacctaacc gaaaagcgaa    120
agctgatacg ggaacagagc acggttggaa agcgatgagt tacctaaaga caatcgggta    180
cgactgagtc gcaatgttaa tcagatataa ggtataagtt gtgtttactg aacgcaagtt    240
tctaatttcg gtttcaatcc gatagaggaa agtgtctgaa acctctagta caaagaaagg    300
taagttatat agaacgactt atctgttatc accacatttg taca                     344
```

<210> SEQ ID NO 61
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer Og125f
<400> SEQUENCE: 61

```
taatccattc ataagcagtt ctaag                                           25
```

<210> SEQ ID NO 62

<210> SEQ ID NO 62
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer Og126r

<400> SEQUENCE: 62
ttactttagg tgaaaaattc ggtat                                     25

<210> SEQ ID NO 63
<211> LENGTH: 325
<212> TYPE: DNA
<213> ORGANISM: Clostridium autoethanogenum
<220> FEATURE:
<221> NAME/KEY: misc_feature
<223> OTHER INFORMATION: CAETHG_3841, sequence of intron targeting
      region

<400> SEQUENCE: 63
aagcttataa ttatccttag atgtccagat agtgcgccca gatagggtgt taagtcaagt    60
agtttaaggt actactctgt aagataacac agaaaacagc caacctaacc gaaaagcgaa   120
agctgatacg ggaacagagc acggttggaa agcgatgagt tacctaaaga caatcgggta   180
cgactgagtc gcaatgttaa tcagatataa ggtataagtt gtgtttactg aacgcaagtt   240
tctaatttcg attacatctc gatagaggaa agtgtctgaa acctctagta caaagaaagg   300
taagttaaat atctggactt atctg                                        325

<210> SEQ ID NO 64
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer Og123f

<400> SEQUENCE: 64
taaatgtgat ttgtgtattg atcag                                     25

<210> SEQ ID NO 65
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer Og124r

<400> SEQUENCE: 65
ctctttaaca gatggaagca tatta                                     25

<210> SEQ ID NO 66
<211> LENGTH: 309
<212> TYPE: DNA
<213> ORGANISM: Clostridium autoethanogenum
<220> FEATURE:
<221> NAME/KEY: misc_feature
<223> OTHER INFORMATION: CAETHG_2797, sequence of intron targeting
      region

<400> SEQUENCE: 66

```
ttatccttac acaacgtctg cgtgcgccca gatagggtgt taagtcaagt agtttaaggt    60
actactctgt aagataacac agaaaacagc caacctaacc gaaaagcgaa agctgatacg   120
ggaacagagc acggttggaa agcgatgagt tacctaaaga caatcgggta cgactgagtc   180
gcaatgttaa tcagatataa ggtataagtt gtgtttactg aacgcaagtt tctaatttcg   240
gttttgtgtc gatagaggaa agtgtctgaa acctctagta caaagaaagg taagttaatg   300
cagacgact                                                            309

<210> SEQ ID NO 67
<211> LENGTH: 20
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer FS001for

<400> SEQUENCE: 67
tagccgatcc tgacaagtgc                                                 20

<210> SEQ ID NO 68
<211> LENGTH: 20
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer FS001rev

<400> SEQUENCE: 68
aagcaggttc tcctccctct                                                 20

<210> SEQ ID NO 69
<211> LENGTH: 309
<212> TYPE: DNA
<213> ORGANISM: Clostridium autoethanogenum
<220> FEATURE:
<221> NAME/KEY: misc_feature
<223> OTHER INFORMATION: CAETHG_2798, sequence of intron targeting
      region

<400> SEQUENCE: 69
ttatccttag gagtcttgcc agtgcgccca gatagggtgt taagtcaagt agtttaaggt    60
actactctgt aagataacac agaaaacagc caacctaacc gaaaagcgaa agctgatacg   120
ggaacagagc acggttggaa agcgatgagt tacctaaaga caatcgggta cgactgagtc   180
gcaatgttaa tcagatataa ggtataagtt gtgtttactg aacgcaagtt tctaatttcg   240
attactcctc gatagaggaa agtgtctgaa acctctagta caaagaaagg taagttaatt   300
ggcaagact                                                            309

<210> SEQ ID NO 70
<211> LENGTH: 26
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: forward primer FS003for

<400> SEQUENCE: 70
```

```
tggaacttta agtgaaggaa aaatgg                                         26

<210> SEQ ID NO 71
<211> LENGTH: 25
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: reverse primer FS003rev

<400> SEQUENCE: 71
tttcaaattc cttgcatgta catgg                                          25
```